US012653459B2

(12) United States Patent
Baum et al.

(10) Patent No.: US 12,653,459 B2
(45) Date of Patent: Jun. 16, 2026

(54) SYSTEMS, DEVICES, AND METHODS FOR BLOOD PRESSURE CONTROL

(71) Applicant: Massachusetts Institute of Technology, Cambridge, MA (US)

(72) Inventors: Taylor Baum, Cambridge, MA (US); Emery Brown, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 807 days.

(21) Appl. No.: 18/163,244

(22) Filed: Feb. 1, 2023

(65) Prior Publication Data

US 2023/0263466 A1     Aug. 24, 2023

Related U.S. Application Data

(60) Provisional application No. 63/313,180, filed on Feb. 23, 2022.

(51) Int. Cl.
A61B 5/00          (2006.01)
A61B 5/02          (2006.01)
(Continued)

(52) U.S. Cl.
CPC ........ A61B 5/4839 (2013.01); A61B 5/02007 (2013.01); A61B 5/021 (2013.01);
(Continued)

(58) Field of Classification Search
CPC .............. A61B 5/4836; A61B 5/02028; A61B 5/02116; A61B 5/02125; A61B 5/024;
(Continued)

(56) References Cited

U.S. PATENT DOCUMENTS 4,080,966 A * 3/1978 McNally .............. A61B 5/7239
                                                    128/DIG. 13
4,392,849 A     7/1983 Petre et al.
(Continued)

FOREIGN PATENT DOCUMENTS

CN      2038366 U      5/1989
EP      0408483 A1     1/1991
WO   2020240200 A1    12/2020

OTHER PUBLICATIONS

Aronow, "Management of hypertension in patients undergoing surgery." Annals of Translational Medicine 5.10 (2017), 3 pages.
(Continued)

*Primary Examiner* — Jason E Flick
(74) *Attorney, Agent, or Firm* — Smith Baluch LLP

(57)          ABSTRACT

A closed-loop system for blood pressure control that accounts for various mechanisms of the cardiovascular system. In some example cases, a pharmacokinetic-pharmacodynamic model of the cardiovascular system's response to cardiovascular system actuators, such as vasoactive drugs, is generated. Two example actuators are employed in the example framework: phenylephrine, to raise blood pressure, and nicardipine, to lower blood pressure. The pharmacodynamic components employs a two-element Windkessel model. A model predictive control framework is built based on the pharmacokinetic-pharmacodynamic model.

20 Claims, 25 Drawing Sheets

(51) Int. Cl.

| | | |
|---|---|---|
| *A61B 5/021* | (2006.01) | |
| *A61K 31/137* | (2006.01) | |
| *A61K 31/4422* | (2006.01) | |
| *A61M 5/142* | (2006.01) | |
| *A61M 5/168* | (2006.01) | |
| *A61M 5/172* | (2006.01) | |

(52) U.S. Cl.

CPC ........ *A61K 31/137* (2013.01); *A61K 31/4422* (2013.01); *A61M 5/16877* (2013.01); *A61M 5/1723* (2013.01)

(58) Field of Classification Search

CPC ... A61B 5/4839; A61B 5/02007; A61B 5/021; A61B 5/02108; A61B 8/04; A61M 5/16877; A61M 5/1723; A61M 2005/14208; A61M 5/142; A61M 2005/14292; A61M 2005/14296; A61M 2005/14288; A61M 2230/30; A61M 5/1407; A61M 2205/3331; A61M 60/531; A61M 60/515; G16H 20/17; G16H 20/10

See application file for complete search history.

(56) References Cited

U.S. PATENT DOCUMENTS

| | | | |
|---|---|---|---|
| 5,733,259 A | 3/1998 | Valcke et al. | |
| 2006/0025931 A1 | 2/2006 | Rosen et al. | |
| 2006/0074404 A1 | 4/2006 | Struble | |
| 2008/0194924 A1 | 8/2008 | Valk et al. | |
| 2011/0190692 A1 | 8/2011 | Manda | |
| 2013/0116615 A1 | 5/2013 | Baym et al. | |
| 2013/0226138 A1* | 8/2013 | Sia .................... | A61M 5/16827 604/66 |
| 2014/0046209 A1 | 2/2014 | Klap et al. | |
| 2015/0286797 A1 | 10/2015 | Ratto | |
| 2017/0147781 A1 | 5/2017 | Gondhalekar et al. | |
| 2017/0235917 A1 | 8/2017 | Bighamian et al. | |
| 2017/0266379 A1* | 9/2017 | Harrity ............... | A61M 5/1407 |
| 2018/0296759 A1 | 10/2018 | Dumont et al. | |
| 2020/0086022 A1 | 3/2020 | El Katerji et al. | |

OTHER PUBLICATIONS

Aronson et. al. "Intraoperative systolic blood pressure variability predicts 30-day mortality in aortocoronary bypass surgery patients." The Journal of the American Society of Anesthesiologists 113.2 (2010): 305-312.

Baum et al. "Theoretical Development of a Closed-Loop System for Blood Pressure Control." 2021 American Control Conference (ACC). IEEE, 2021, 6 pages.

Baum, "Steps Towards a Closed-Loop System for Blood Pressure Control," MIT Master's Thesis, Sep. 2021, 88 pages.

Bighamian et al. "Control-oriented physiological modeling of hemodynamic responses to blood vol. perturbation." Control Engineering Practice 73 (2018): 149-160.

Bighamian et al. "Is there opportunity for automated decision-support and closed-loop control in ICU patients receiving vasopressor infusion?." 2014 36th Annual International Conference of the IEEE Engineering in Medicine and Biology Society. IEEE, 2014 pp. 1949-1952.

Charlson et al. "Intraoperative blood pressure. What patterns identify patients at risk for postoperative complications?." Annals of Surgery 212.5 (1990): 567-580.

Cook et al., "Pharmacokinetics, pharmacodynamics, and minimum effective clinical dose of intravenous nicardipine." Clinical Pharmacology & Therapeutics 47.6 (1990): 706-718.

Curran et. al. "Intravenous nicardipine: Its Use in the Short-Term Treatment of Hypertension and Various Other Indications." Drugs 66.13 (2006): 1755-1782.

Frank, "Die grundform des arteriellen pulses." Zeitung fur Biologie 37 (Translation-Basic Shape of Arterial Pulse, Newspaper for Biology), (1899): 483-526, 44 pages.

Furutani et al., "Blood pressure control during surgical operations." IEEE Transactions on Biomedical Engineering 42.10 (1995): 999-1006.

Furutani et. al. "An automatic control system of the blood pressure of patients under surgical operation." International Journal of Control, Automation, and Systems 2.1 (2004): 39-54.

Hahn, Model-Based Fluid/Vasopressor Resuscitation Presentation. FDA Public Workshop on PCLC Devices Oct. 14, 2015. 18 pages.

Hahn, Modeling and Model-Based Control Design/Testing Presentation. FDA Public Workshop on PCLC Devices Oct. 13, 2015. 18 pages.

Hengstmann et al., "Pharmacokinetics of 3 H-phenylephrine in man." European Journal of Clinical Pharmacology 21.4 (1982): 335-341.

Hoadley, Model-Based Design of Medical Devices PCLC Workshop. MathWorks Oct. 13, 2015. 15 pages.

Howell et al., "Hypertension, hypertensive heart disease and perioperative cardiac risk." British Journal of Anaesthesia 92.4 (2004): 570-583.

Hug et al. "Hemodynamic effects of propofol: Data from over 25,000 patients." Anesthesia and Analgesia 77.4 Suppl (1993): S21-9, 9 pages.

Isaka et. al. "Control strategies for arterial blood pressure regulation." IEEE Transactions on Biomedical Engineering 40.4 (1993): 353-363, 11 pages.

Jinadasa et al. "Blood pressure coefficient of variation and its association with cardiac surgical outcomes." Anesthesia & Analgesia 127.4 (2018): 832-839.

Khodaei et al., "Physiological Closed-Loop Control (PCLC) Systems: Review of a Modern Frontier in Automation." arXiv preprint arXiv:1910.03768 (2019). 39 pages.

Kuck, "The three laws of autonomous and closed-loop systems in anesthesia. "Anesthesia and Analgesia, (2017): 377-380.

Manju et al., "Design of drug delivery system for blood pressure control." 2013 Annual International Conference on Emerging Research Areas and 2013 International Conference on Microelectronics, Communications and Renewable Energy. IEEE, 2013. 5 pages.

Mark, "Cardiovascular mechanics: quantitative physiology: Organ transport systems," 2004. MIT Course No. HST.542J / 2.792J / 20.371J / 6.022J. https://ocw.mit.edu/courses/health-sciences-and-technology/hst-542j-quantitative-physiology-organ-transport-systems-spring-2004, 1 page.

Marques et al., "Physician-directed versus computerized closed-loop control of blood pressure using phenylephrine in a swine model." Anesthesia & Analgesia 125.1 (2017): 110-116.

McInnis et al. "Automatic control of blood pressures with multiple drug inputs." Annals of Biomedical Engineering 13.3 (1985): 217-225.

Morris et al., "Crisis management during anaesthesia: hypotension." Quality & Safety in Health Care 14.3 (2005): e11-e11, 7 pages.

Parvinian et al., "Regulatory considerations for physiological closed-loop controlled medical devices used for automated critical care: food and drug administration workshop discussion topics." Anesthesia and Analgesia 126.6 (2018): 1916. 10 pages.

Physiological Closed-Loop Controlled Devices; Public Workshop; Request for Comments. 80 Fed. Reg. 49,248-49,250. Aug. 17, 2015. 3 pages.

Silva et al., "Multi-Model Adaptive Predictive Control System for Automated Regulation of Mean Blood Pressure." International Journal of Online & Biomedical Engineering 15.11 (2019): 69-87.

Simanski et al., "Automatic drug delivery in anesthesia: From the beginning until now." 2007 Mediterranean Conference on Control & Automation. IEEE, 2007. 7 pages.

Slate et. al. "Automatic control of blood pressure by drug infusion." IEE Proceedings A-Physical Science, Measurement and Instrumentation, Management and Education-Reviews 129.9 (1982): 639-645.

Sondhi et al. "Fractional-order PI controller with specific gain-phase margin for MABP control." IETE Journal of Research 61.2 (2015): 142-153.

(56) References Cited

OTHER PUBLICATIONS

Tafreshi et al., "Real-time closed-loop control of human heart rate and blood pressure." IEEE Transactions on Biomedical Engineering 62.5 (2015): 1434-1442.

Vanvalkinburgh et. al. "Inotropes and vasopressors," StatPearls, pp. 1-5, 2021 https://www.ncbi.nlm.nih.gov/books.

Walsh et al. "Relationship between intraoperative mean arterial pressure and clinical outcomes after noncardiac surgery: toward an empirical definition of hypotension." Anesthesiology 119.3 (2013): 507-515.

Wesselink et al. "Intraoperative hypotension and the risk of post-operative adverse outcomes: a systematic review." British Journal of Anaesthesia 121.4 (2018): 706-721.

* cited by examiner $t_{s,10}$ OF $P_{PATIENT}$ TO $P_{TARGET}$

ESTIMATION FRAMEWORK

BLOOD PRESSURE WAVEFORM

BLOOD
PRESSURE
[mmHg]

TIME [sec]

IMPULSE TRAIN OF INPUT BLOOD VOLUME

BLOOD VOLUME
INJECTED INTO
SYSTEM [L]

INPULSE
AREA:
$\Delta V_k$

TIME [sec]

ABSTRACT MODEL OF CARDIOVASCULAR STATE

HIDDEN
CARDIOVASCULAR
STATE

BLOOD
PRESSURE
WAVEFORM
OBSERVATIONS

SYSTEMS, DEVICES, AND METHODS FOR BLOOD PRESSURE CONTROL

CROSS-REFERENCE TO RELATED APPLICATIONS

This application claims priority to U.S. Provisional Application No. 63/313,180 titled "STEPS TOWARDS A CLOSED-LOOP SYSTEM FOR BLOOD PRESSURE CONTROL", filed Feb. 23, 2022, the entire disclosure of which is incorporated herein by reference.

BACKGROUND

Management of blood pressure in the operating room is currently done manually by anesthesiologists. Poor blood pressure management has been linked to poor post-operative outcomes. Previous attempts at solving this problem fall short in their lack of incorporation of mechanistic cardio-vascular models.

SUMMARY

In some aspects, a system for controlling blood pressure in a subject includes a sensor coupled to the subject and configured to measure a blood pressure waveform of the subject. The system further includes a pump coupled to the subject and configured to a) inject a first substance including a vasopressor into the subject, and b) a second substance including a vasodilator into the subject. The system further includes a processor communicatively coupled to the sensor and the pump and configured to receive an indication of a target blood pressure waveform of the subject. The processor is further configured to receive, from the sensor, an indication of the measured blood pressure waveform of the subject. The processor is further configured to calculate an estimated blood pressure waveform of the subject based on a circuit model of blood circulation in one or more blood vessels of the subject. It does so by setting an input blood flow parameter of the circuit model to be an impulse train, setting an arterial compliance parameter of the circuit model to be time invariant, setting a microcirculation resistance parameter of the circuit model to be time invariant during a heartbeat and time variant between each heartbeat, and calculating the estimated blood pressure waveform by solving the circuit model based on the input blood flow parameter, the arterial compliance parameter, the microcirculation resistance parameter, and the measured blood pressure waveform. The processor is further configured to calculate, based on the estimated blood pressure waveform and the target blood pressure waveform, one or more infusion rates for the first substance, for the second substance, or both. The processor is further configured to transmit an indication of the one or more calculated infusion rates to the pump, wherein the pump is further configured to modify an infusion rate of the first substance, of the second substance, or both, based on the one or more calculated infusion rates.

In some aspects, a method for controlling blood pressure in a subject includes measuring a blood pressure waveform of the subject and injecting a first substance including a vasopressor into the subject, and a second substance including a vasodilator into the subject. The method further includes receiving an indication of a target blood pressure waveform of the subject and calculating an estimated blood pressure waveform of the subject based on a circuit model of blood circulation in one or more blood vessels of the subject. The calculating includes setting an input blood flow parameter of the circuit model to be an impulse train, setting an arterial compliance parameter of the circuit model to be time invariant, setting a microcirculation resistance parameter of the circuit model to be time invariant during a heartbeat, and time variant between each heartbeat, and calculating the estimated blood pressure waveform by solving the circuit model based on the input blood flow parameter, the arterial compliance parameter, the microcirculation resistance parameter, and the measured blood pressure waveform. The method further includes calculating, based on the estimated blood pressure waveform and the target blood pressure waveform, one or more infusion rates for the first substance, for the second substance, or both. The method also includes modifying an infusion rate of the first substance, of the second substance, or both, based on the one or more calculated infusion rates.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 is a hybrid system-method illustration useful for closed loop control of blood pressure.

FIG. 2 shows a graphical representation of a general two-compartment PK model. A drug is infused into the first compartment with compartmental concentration, $c_1$, at some rate, u. This drug moves between the first compartment and second compartment with compartmental concentration, $c_2$, with rates $k_{12}$ and $k_{21}$. The drug is also being eliminated from the body with rate $k_{el}$. This elimination of the drug is being represented by Ø. These are mass flow rate constants.

FIG. 3 shows a Windkessel model circuit representation. Here, the Windkessel Model is represented as a circuit where the arterial compliance, $C_a$, is represented as a capacitor, the resistance of the microcirculation, $R_a$, is represented as a resistor, and the volumetric inflow into the blood vessels from the heart, Q(t), is represented as a current source.

FIG. 4 shows example simulation results for the following conditions: following initialization of the Windkessel Model, the system is simulated forward for the first 50 seconds. The controller is turned on and the blood pressure is modulated up 10 mmHg, returned to baseline, modulated down 10 mmHg, and returned back to baseline. The left y-axis pertains to the black simulated blood pressure waveform. The right y-axis corresponds to the step function infusion rates of PE and NI. The target was $P_m$, in this case, as specified by the green dotted lines. Through specifying a target $P_m$, by the model definition, a target $P_s$ and a target $P_d$ are also specified.

FIG. 5 shows an example visualization of a steady-state systolic pressure, $P_s$, diastolic pressure, $P_d$, and mean arterial pressure, $P_m$. It does not refer to a non-oscillating blood pressure waveform, but, instead, a stationarity in the oscillation of the output blood pressure waveform from the two-element Windkessel model, leading to a constant $P_s$, $P_d$, and $P_m$ given constant Windkessel parameters. In this example, the Windkessel model is simulated with the following constant parameters: $R_a$=1 [mmHg·sec·ml$^{-1}$], $C_a$=1.45 [ml·mmHg$^{-1}$], HR=60 [bpm], and $\Delta$V=86 [ml]

FIG. 6 shows an illustration of the implementation of this state estimation framework on swine data. In the top plot, the ground truth cardiac output in [L·min$^{-1}$] is shown and taken from an aortic flow waveforms from a swine compared with the estimated cardiac output calculated with the proposed Kalman filter. In the middle plot, the mean arterial pressure in [mmHg] is shown over time in [sec]. In the bottom plot, the heart rate in [beats·min$^{-1}$] is shown over time in [sec].

Figure 10A:
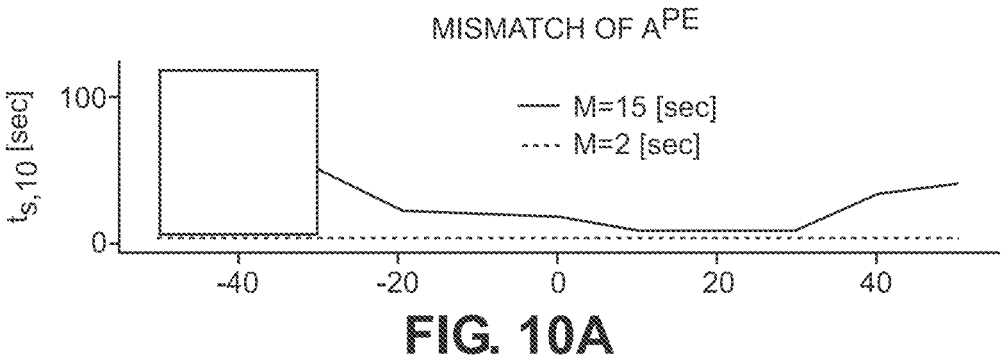

FIG. 10A shows the relationship between observed $t_{s,10}$ and mismatch of $A^{PE}$ depending on M from simulations to illustrate the impact of model mismatch on $t_{s,10}$ with varied switching constraints. The portions of the graph which are shaded in represent areas where $t_{s,10}$ is undefined because the mismatch from $\theta_{patient}$ to $\theta_{internal}$ led to a steady-state offset above 10 [mmHg]. The shaded regions show steady-state offset above 10 [mmHg] when M=2 [sec] and M=15 [sec].

Figure 10B:
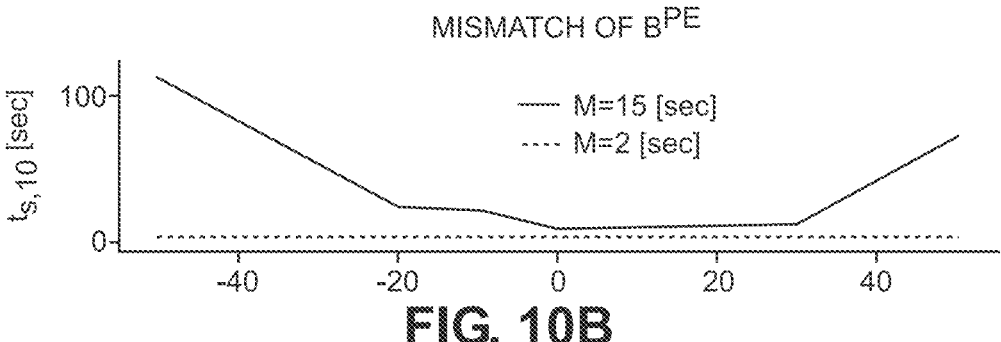

FIG. 10B shows the relationship between observed $t_{s,10}$ and mismatch of $B^{PE}$ depending on M from simulations for the model mismatch of FIG. 10A. The shaded regions are interpreted in the same manner as FIG. 10A.

Figure 10C:
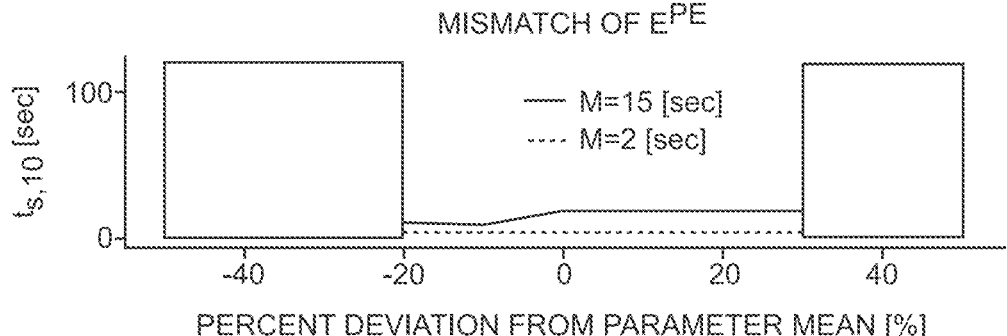

FIG. 10C shows the relationship between observed $t_{s,10}$ and mismatch of $E^{PE}$ depending on M from simulations for the model mismatch of FIG. 10A. The shaded regions are interpreted in the same manner as FIG. 10A.

Figure 11A:
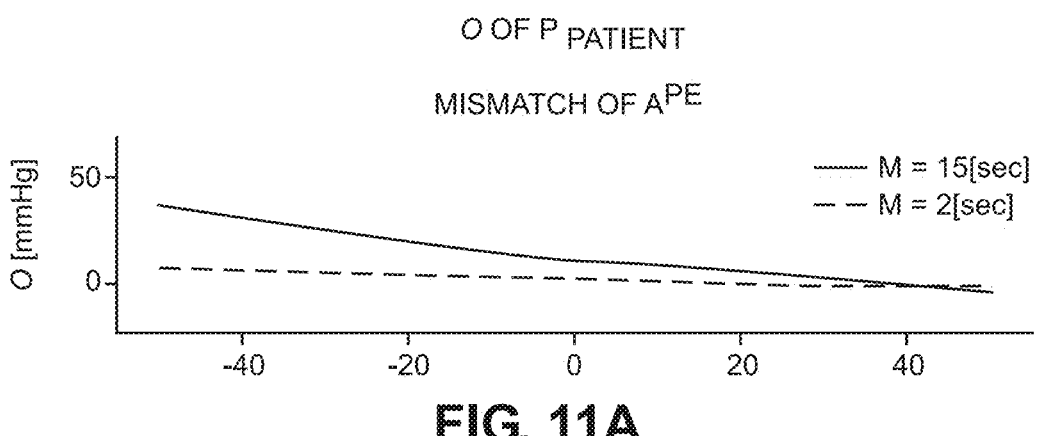

FIG. 11A shows the relationship between observed O and mismatch of $A^{PE}$ depending on M from simulations to illustrate the impact of model mismatch on O with varied switching constraints.

Figure 11B:
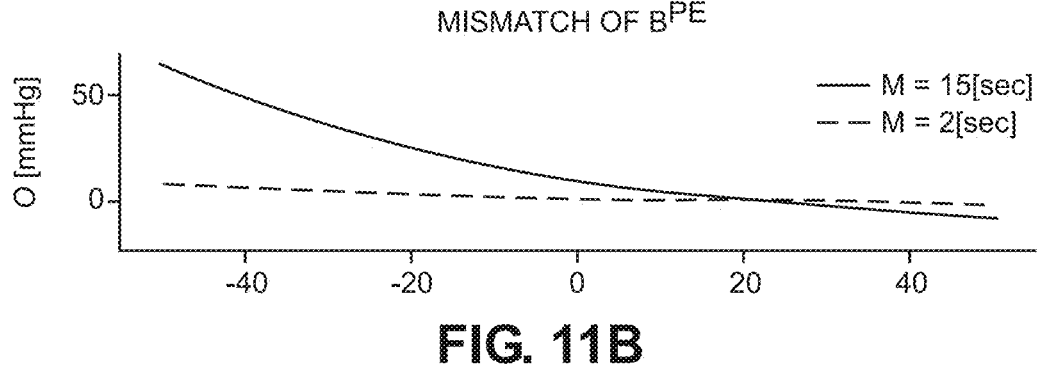

FIG. 11B shows the relationship between observed O and mismatch of BP E depending on M from simulations for the model mismatch of FIG. 11A.

Figure 11C:
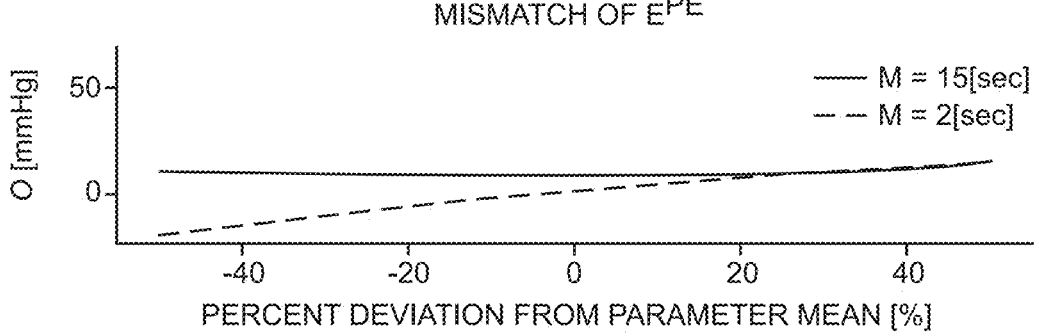

FIG. 11C shows the relationship between observed O and mismatch of EP E depending on M from simulations for the model mismatch of FIG. 11A.

Figure 12A:
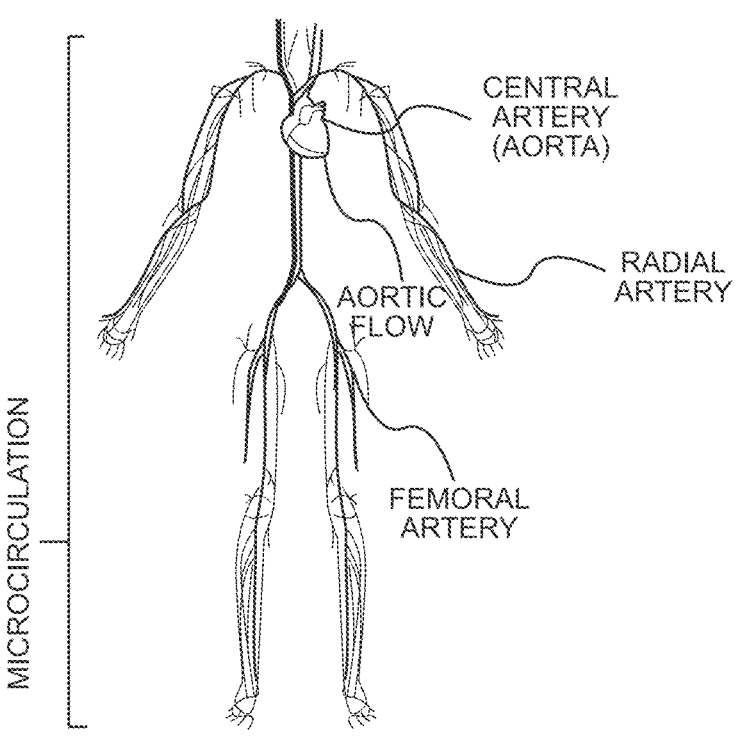

FIG. 12A shows a human circulatory system with locations of ABP recordings and AF recordings of the experimental data as described in Section 4.2.4, to illustrate the physiological model with human physiology. The experimental data set includes recordings for AF, and three locations of blood pressure data. The microcirculation, the small vessels located throughout the cardiovascular system, is indicated because it is the primary contribution towards R in the two-element Windkessel model.

Figure 12B:
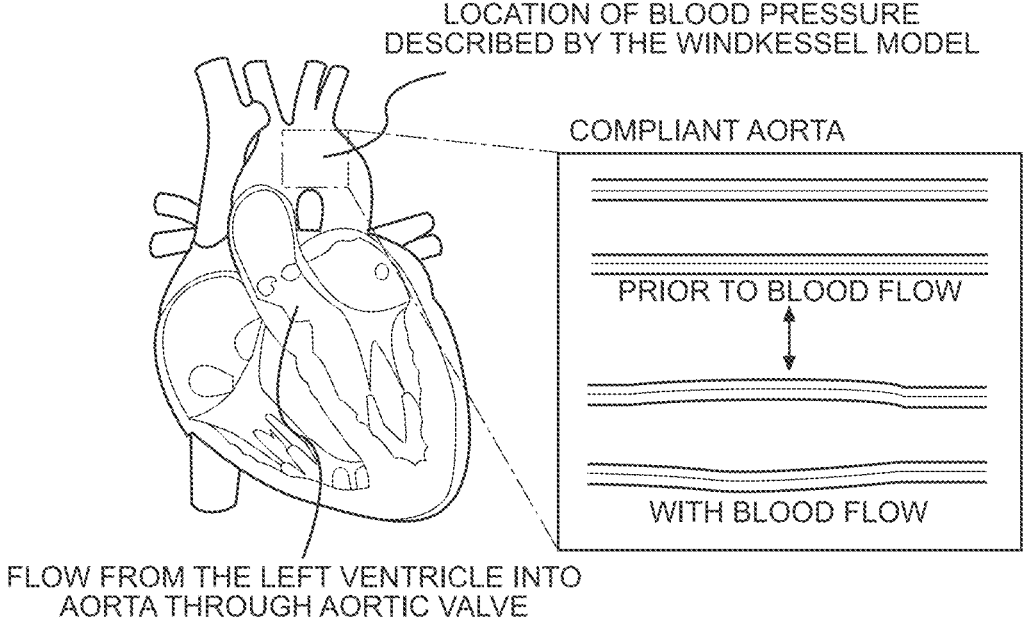

FIG. 12B shows the location of AF and ABP represented in the two-element Windkessel model. In this example, the aorta is a highly compliant (C) artery.

Figure 12C:
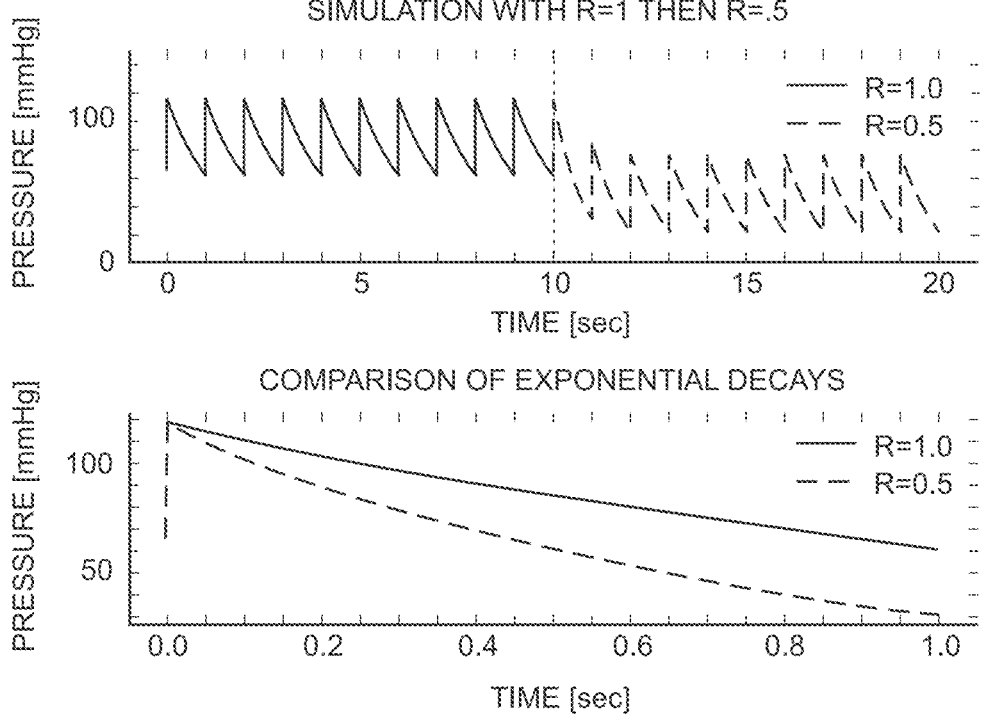

FIG. 12C shows, in the top plot, a simulation of the Windkessel Model forward in time with R=1 and C=1 from 0≤t<10 and then R=0.5 and C=1 from 10≤t<20. In the bottom plot, a comparison of the exponential decay of one beat for C=1 and R=1 or R=0.5.

Figure 12D:
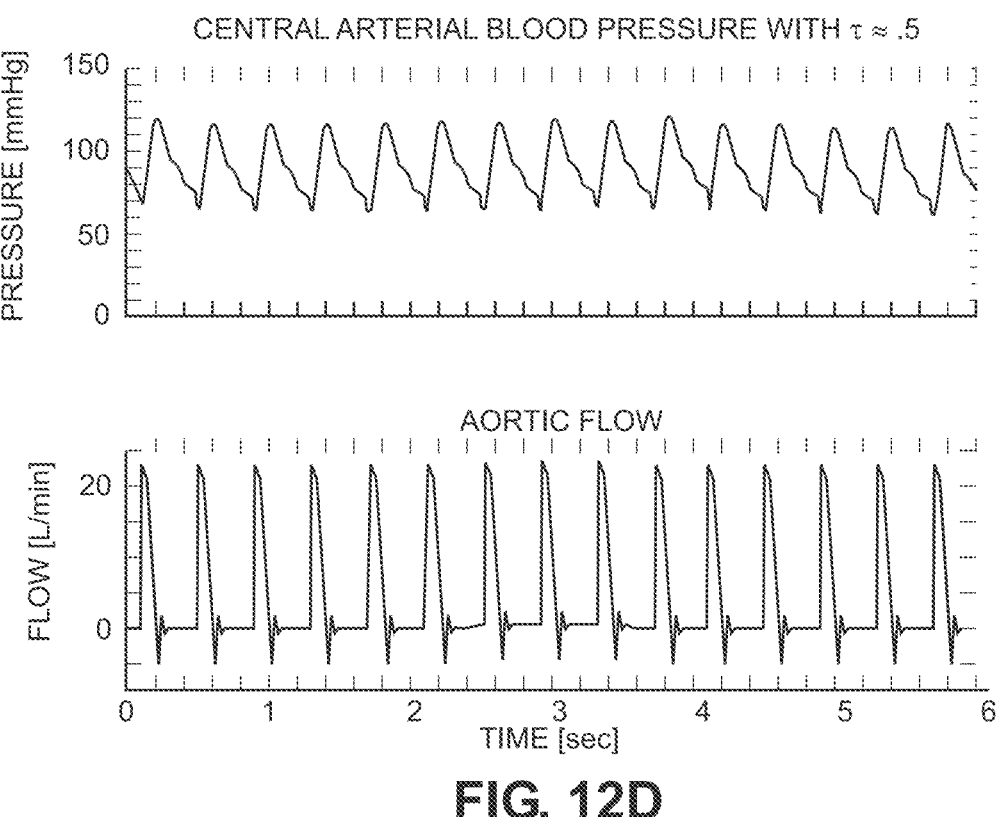

FIG. 12D shows in vivo swine central ABP, $p^{central}$, waveforms with differing estimated time constants of the two-element Windkessel model. Specifically, the top plot shows $p^{central}$, with τ≈1. The bottom plot shows the corresponding f(t) waveform when τ≈1.

Figure 12E:
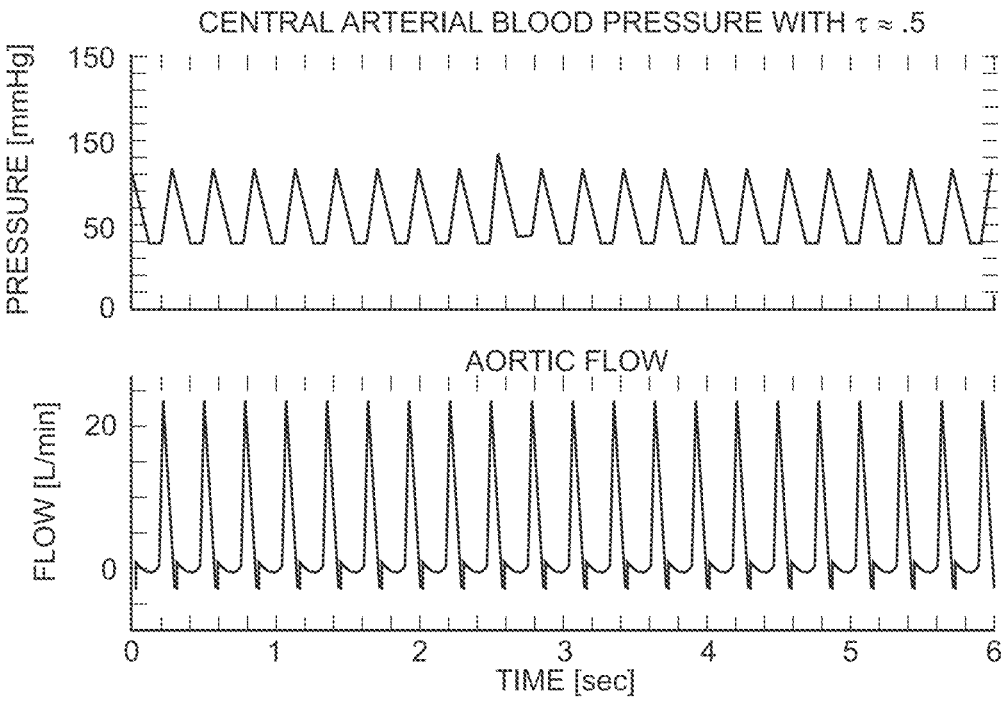

FIG. 12E shows, in the top plot, $p^{central}$ with τ≈0.5. The bottom plot shows the corresponding f(t) waveform when τ≈0.5.

Figure 13A:
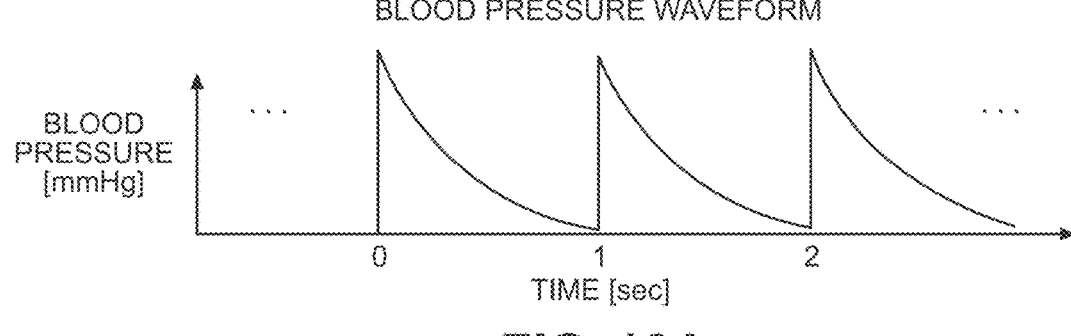

FIG. 13A shows a modelled p[n] from a two-element Windkessel Model, which forms part of the Kalman Estimation Framework. Specifically, a graphical model of τ is built in relation to p[n], and then a Kalman filter is built around this model to learn τ.

Figure 13B:
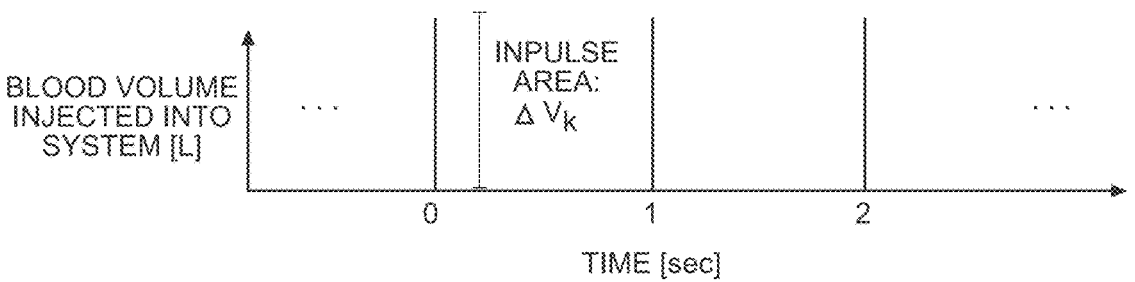

FIG. 13B shows a modelled f[n] as impulses of stroke volume, $\Delta V_k$, in the Kalman Estimation Framework of FIG. 13A.

Figure 13C:
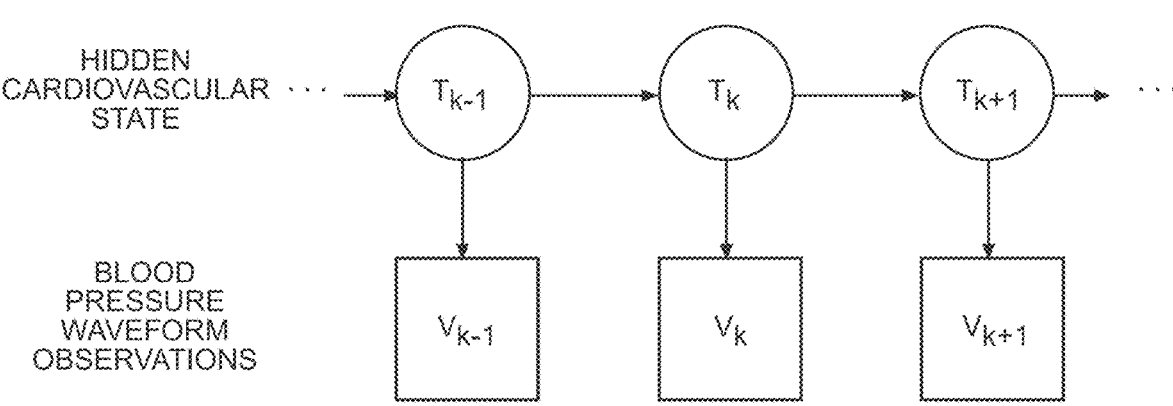

FIG. 13C shows a graphical model of $\tau_k$ related to ABP observations, $v_k$, in the Kalman Estimation Framework of FIG. 13A.

Figure 13D:
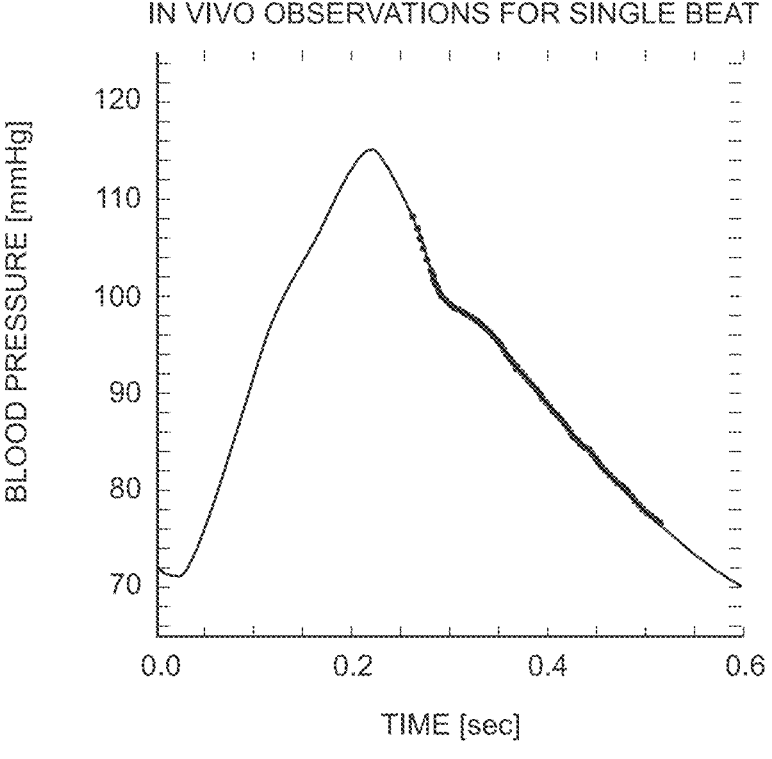

FIG. 13D shows example in vivo blood pressure observations.

Figure 13E:
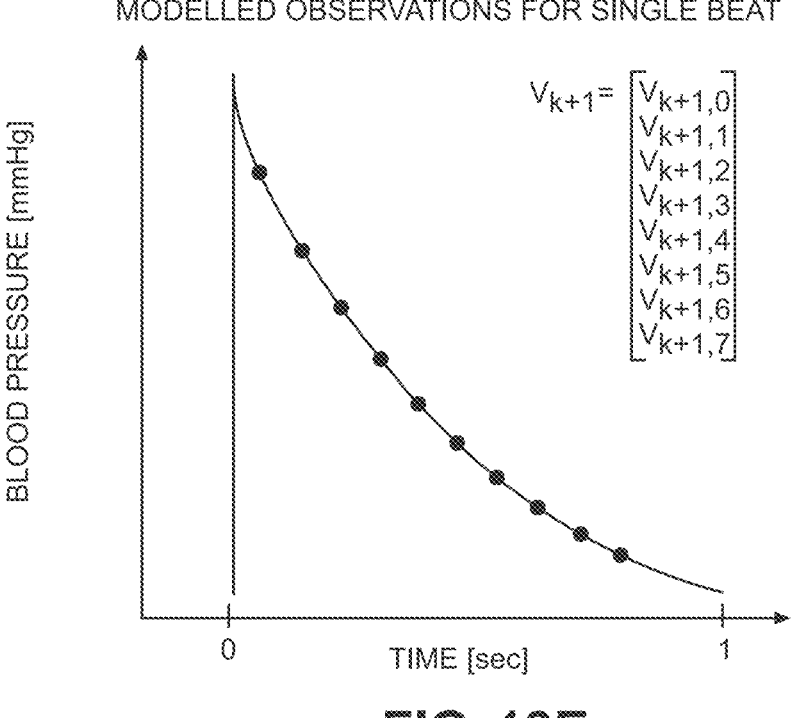

FIG. 13E shows modelled p[n] observations. A Kalman filter is constructed from Windkessel model assumptions to get an estimate of $\tau_k$ from the observations from each beat.

Figures 13F, 13G, 13H:
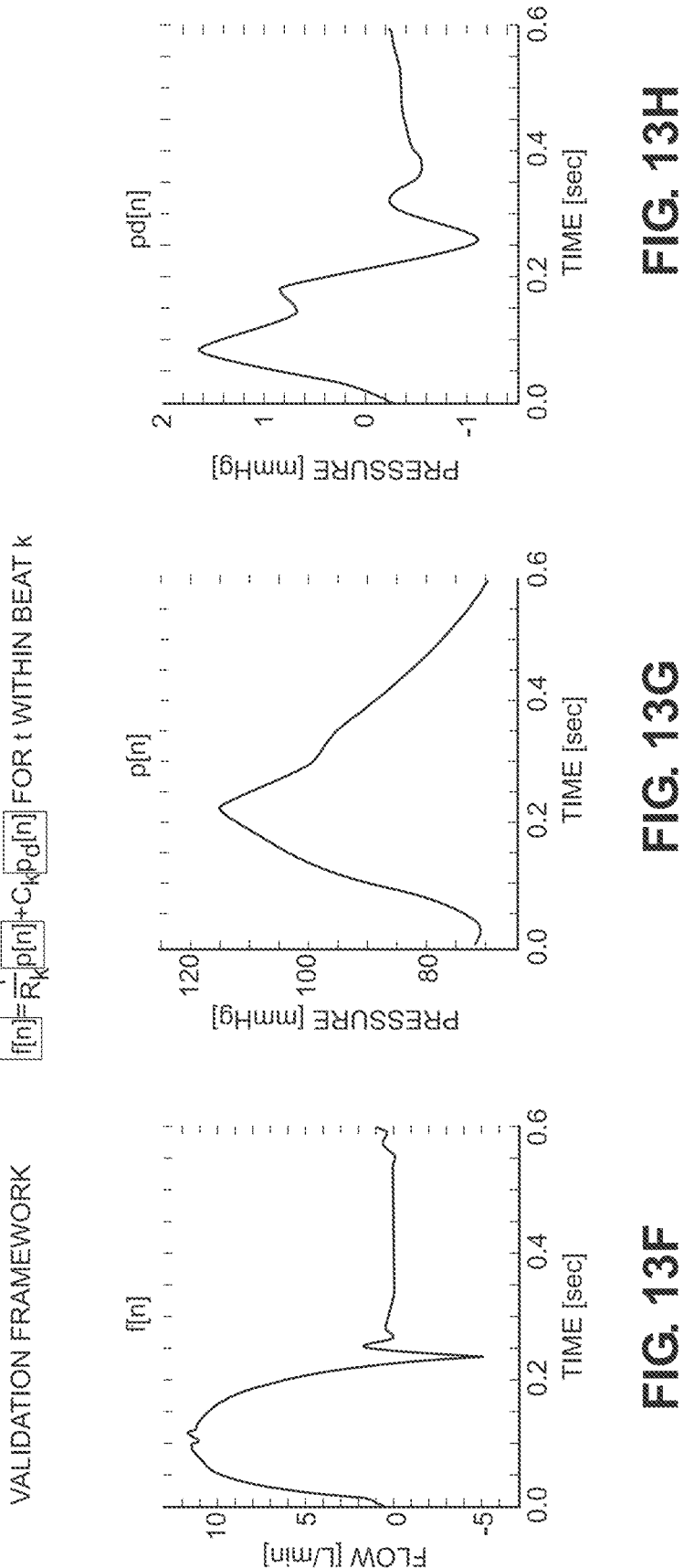

FIG. 13F shows an example in vivo AF waveform, f[n], from a swine, to illustrate the validation framework. Specifically, the dynamic equation from the two-element Windkessel model is used to generate validation estimates using f[n], p[n], and $p_d$[n].

FIG. 13G shows an example in vivo ABP waveform, p[n], from a swine for the validation framework of FIG. 13F.

FIG. 13H shows an example in vivo backwards difference vector of p[n], $p_d$[n] for the validation framework of FIG. 13F.

Figure 14A:
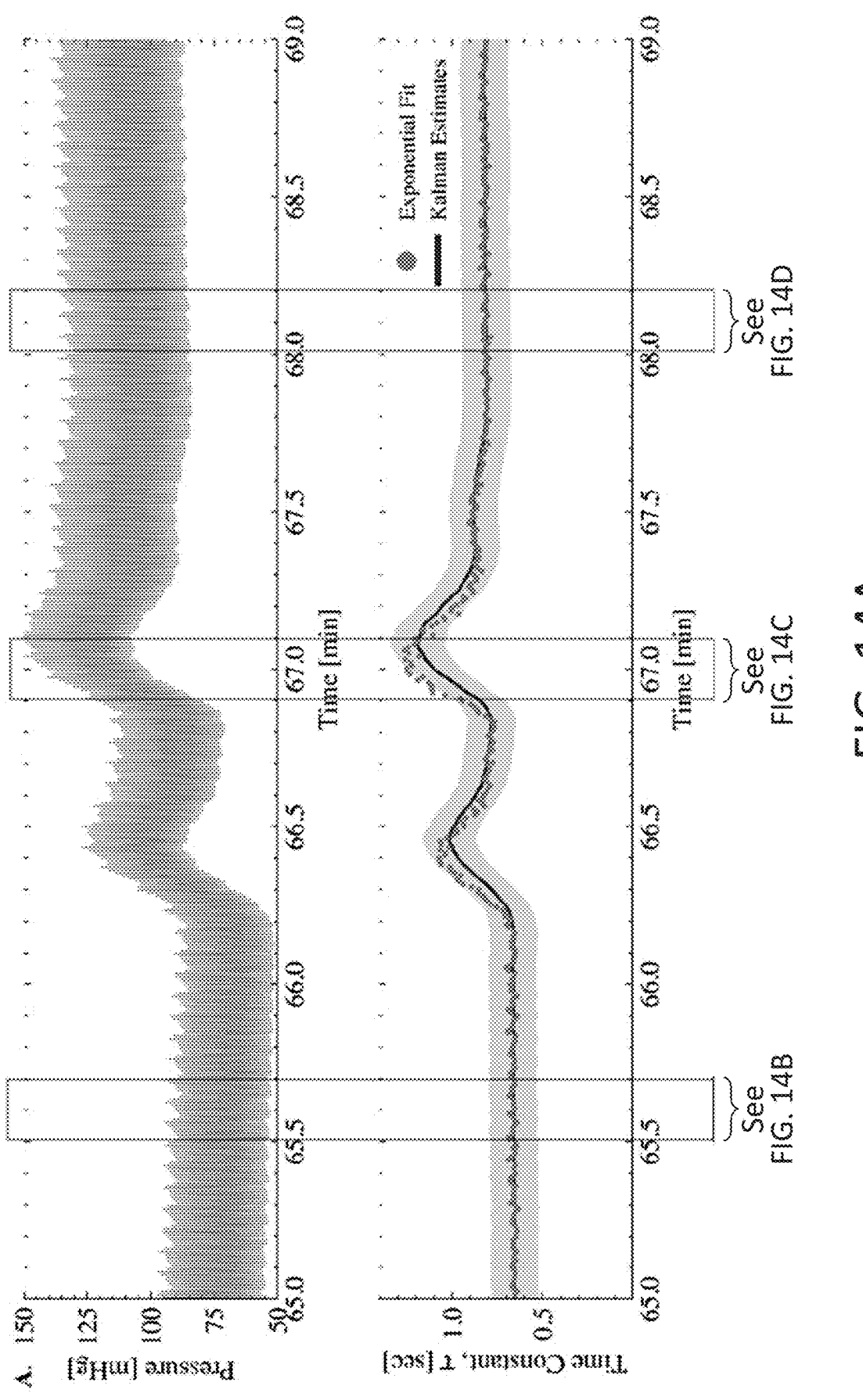

FIG. 14A shows, in the top plot, a segment of a central ABP waveform to illustrate the benefits of the Kalman Estimation Framework for Experiment 1. In the bottom plot, corresponding Kalman estimates along with exponential fit estimates lacking history dependence are shown.

Figures 14B, 14C, 14D:
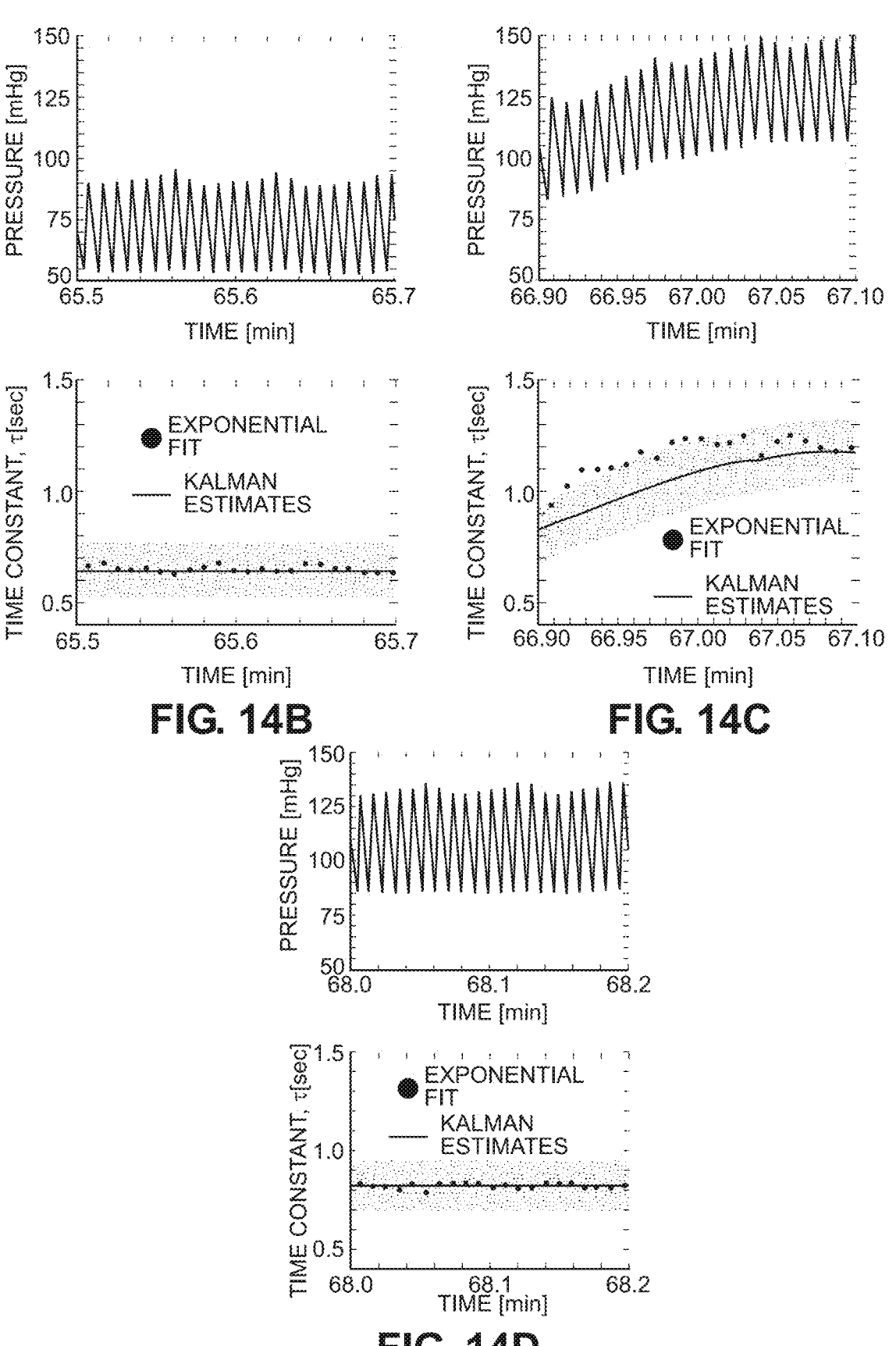

FIG. 14B shows the Kalman estimates' resistance to breathing artifacts with τ≈0.6. The top plot shows a magnified segment of the central ABP waveform and the bottom plot shows the corresponding Kalman estimates, along with exponential fit estimates lacking history dependence.

FIG. 14C shows the Kalman estimates' responsiveness to rapid changes in τ. The top plot shows a magnified segment of the central ABP waveform and the bottom plot shows the corresponding Kalman estimates, along with exponential fit estimates lacking history dependence.

FIG. 14D shows the Kalman estimates' resistance to breathing artifacts with τ≈0.8. The top plot shows a magnified segment of the central ABP waveform and the bottom plot shows the corresponding Kalman estimates, along with exponential fit estimates lacking history dependence.

Figures 15A, 15B, 15C, 15D:
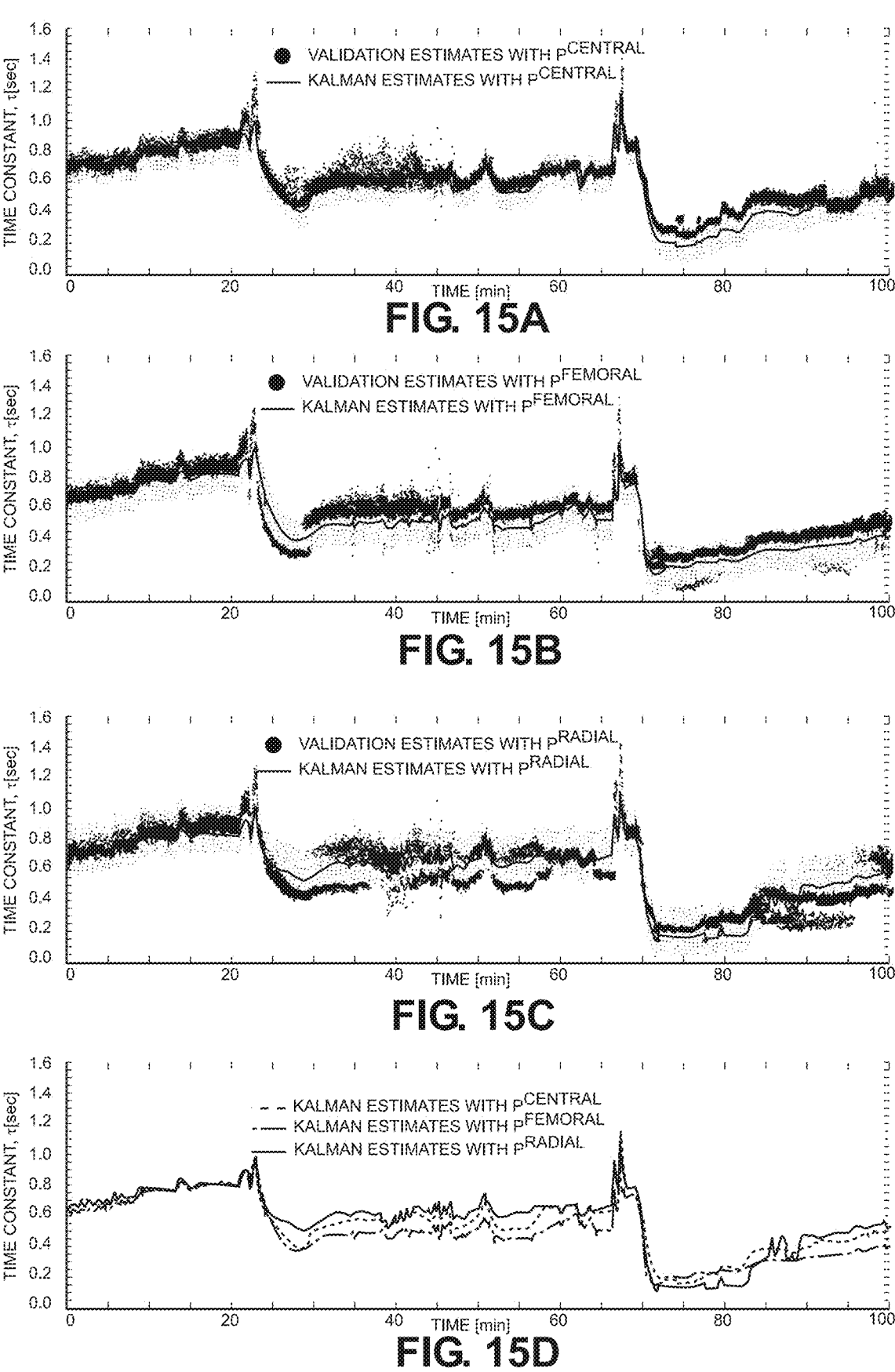

FIG. 15A shows, for Experiment 1, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 15B shows, for Experiment 1, a comparison of the beat-by-beat Kalman estimate of τ using the central ABP Waveform, $p^{femoral}$ versus the beat-by-beat validation estimate of τ using the central ABP waveform, $p^{femoral}$ and the AF Waveform, f.

FIG. 15C shows, for Experiment 1, a comparison of the beat-by-beat Kalman estimate of τ using the central ABP Waveform, $p^{radial}$ versus the beat-by-beat validation estimate of τ using the central ABP waveform, $p^{radial}$ and the AF Waveform, f.

FIG. 15D shows, for Experiment 1, a comparison of Kalman Estimates and Validation Estimates using Central, Radial, or Femoral ABP Waveforms. In this plot, the agreement of the Kalman estimates are shown for the best result using a central, radial, or femoral ABP waveform. The areas where the results are a lighter blue for the central Kalman estimate indicate the presence of a large dicrotic notch.

Figures 16A, 16B, 16C, 16D:
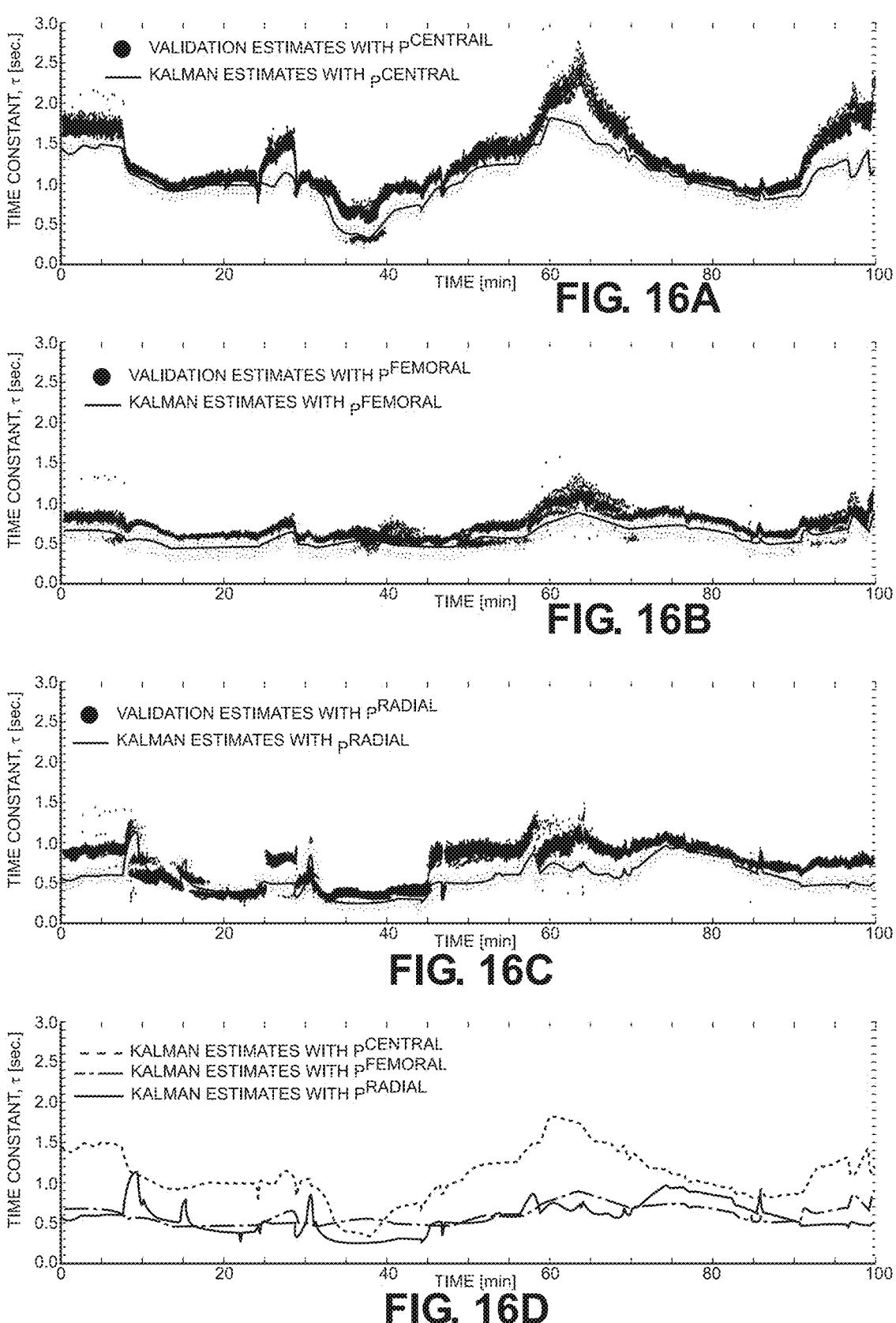

FIG. 16A shows, for Experiment 2, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 16B shows, for Experiment 2, a comparison of the beat-by-beat Kalman estimate of τ using the central ABP Waveform, $p^{femoral}$ versus the beat-by-beat validation estimate of τ using the central ABP waveform, $p^{femoral}$ and the AF Waveform, f.

FIG. 16C shows, for Experiment 2, a comparison of the beat-by-beat Kalman estimate of τ using the central ABP Waveform, $p^{radial}$ versus the beat-by-beat validation estimate of τ using the central ABP waveform, $p^{radial}$ and the AF Waveform, f.

FIG. 16D shows, for Experiment 2, a comparison of Kalman Estimates and Validation Estimates using Central, Radial, or Femoral ABP Waveforms. In this plot, the agreement of the Kalman estimates are shown for the best result using a central, radial, or femoral ABP waveform. The areas where the results are a lighter blue for the central Kalman estimate indicate the presence of a large dicrotic notch.

Figures 17A, 17B, 17C, 17D:
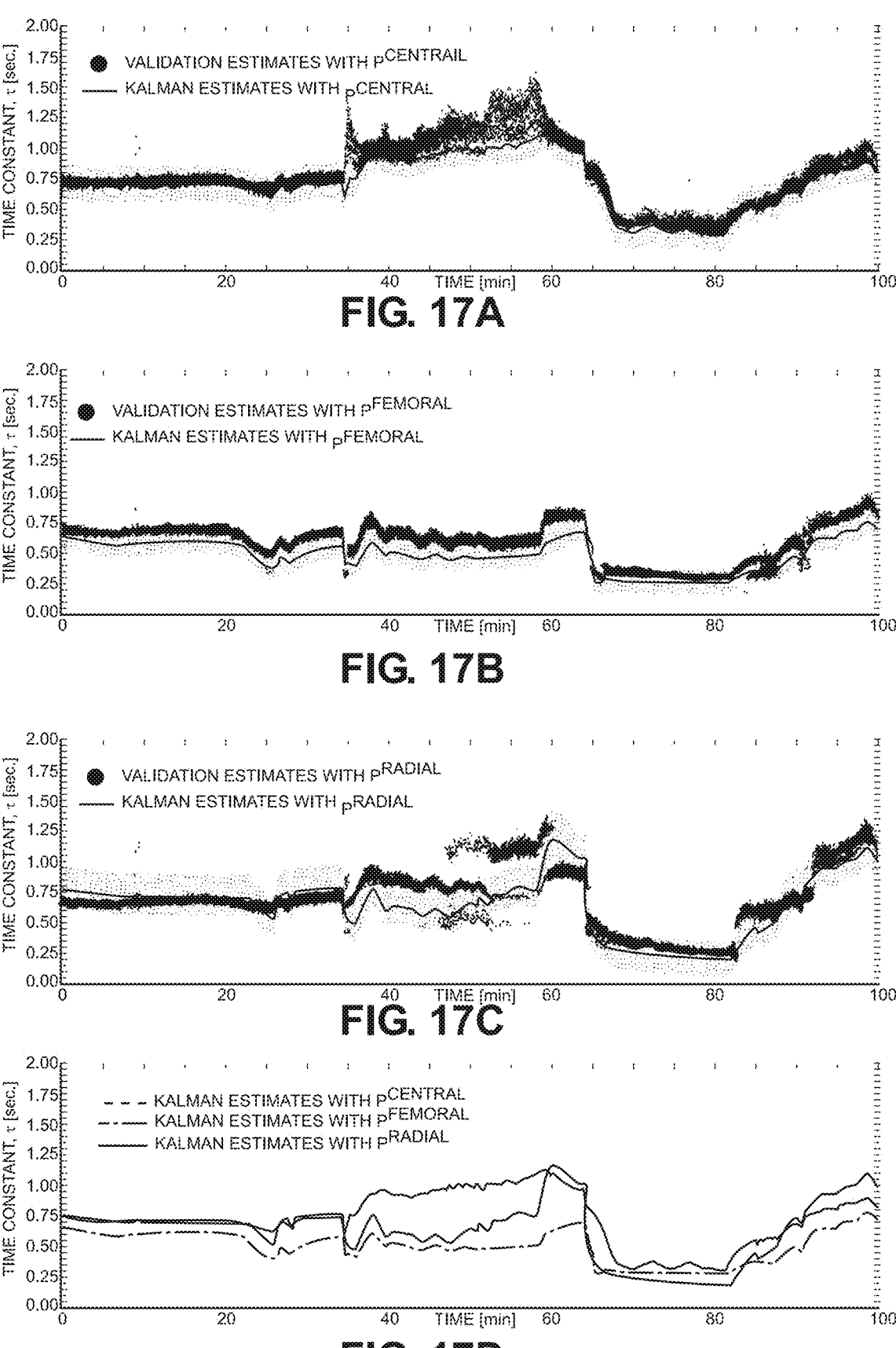

FIG. 17A shows, for Experiment 3, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 17B shows, for Experiment 3, a comparison of the beat-by-beat Kalman estimate of τ using the central ABP Waveform, $p^{femoral}$ versus the beat-by-beat validation estimate of τ using the central ABP waveform, $p^{femoral}$ and the AF Waveform, f.

FIG. 17C shows, for Experiment 3, a comparison of the beat-by-beat Kalman estimate of τ using the central ABP Waveform, $p^{radial}$ versus the beat-by-beat validation estimate of τ using the central ABP waveform, $p^{radial}$ and the AF Waveform, f.

FIG. 17D shows, for Experiment 3, a comparison of Kalman Estimates and Validation Estimates using Central, Radial, or Femoral ABP Waveforms. In this plot, the agreement of the Kalman estimates are shown for the best result using a central, radial, or femoral ABP waveform. The areas where the results are a lighter blue for the central Kalman estimate indicate the presence of a large dicrotic notch.

Figures 18A, 18B, 18C, 18D:
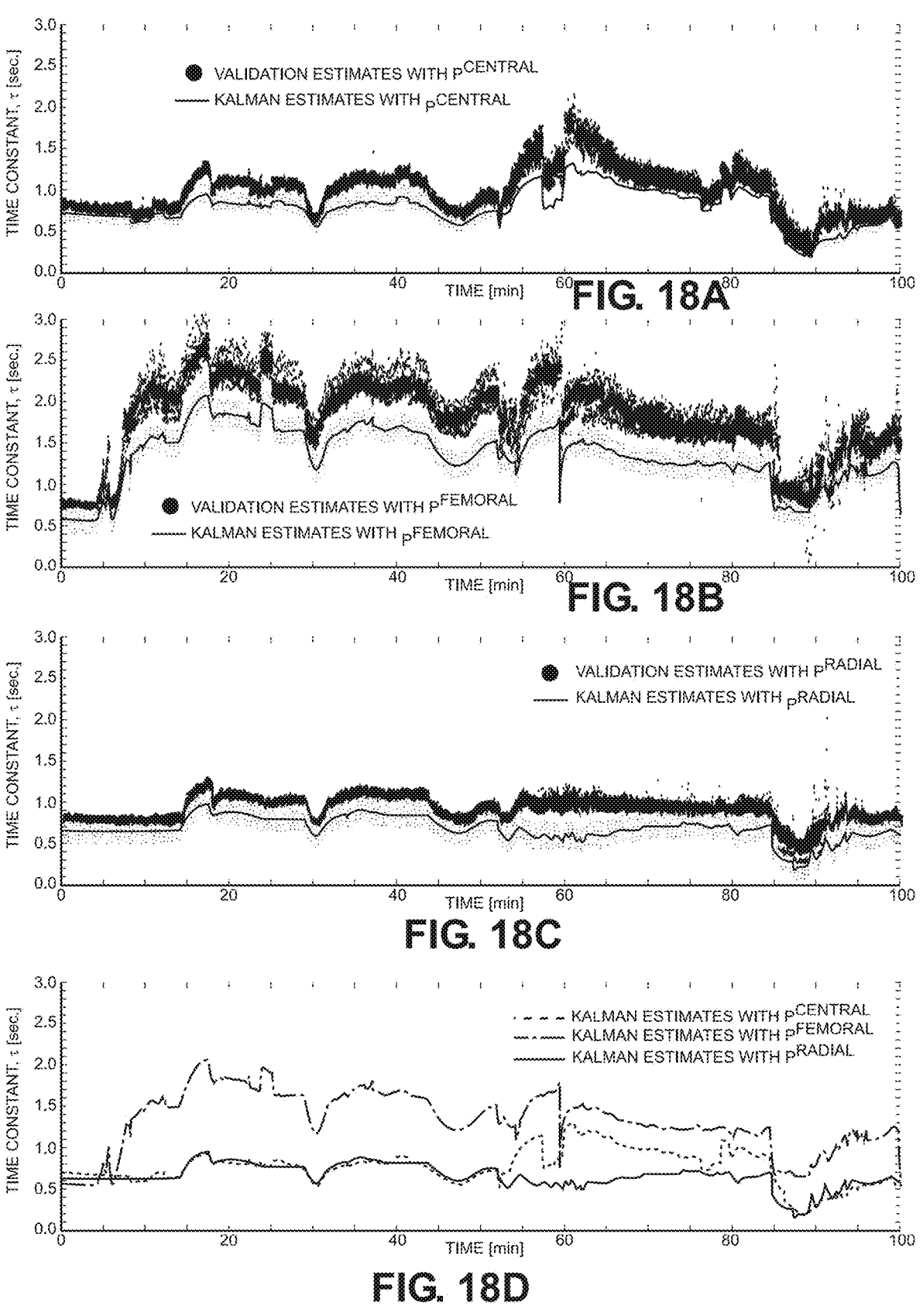

FIG. 18A shows, for Experiment 4, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 18B shows, for Experiment 4, a comparison of the beat-by-beat Kalman estimate of τ using the central ABP Waveform, $p^{femoral}$ versus the beat-by-beat validation estimate of τ using the central ABP waveform, $p^{femoral}$ and the AF Waveform, f.

FIG. 18C shows, for Experiment 4, a comparison of the beat-by-beat Kalman estimate of τ using the central ABP Waveform, $p^{radial}$ versus the beat-by-beat validation estimate of τ using the central ABP waveform, $p^{radial}$ and the AF Waveform, f.

FIG. 18D shows, for Experiment 4, a comparison of Kalman Estimates and Validation Estimates using Central, Radial, or Femoral ABP Waveforms. In this plot, the agreement of the Kalman estimates are shown for the best result using a central, radial, or femoral ABP waveform.

Figures 19A, 19B, 19C, 19D:
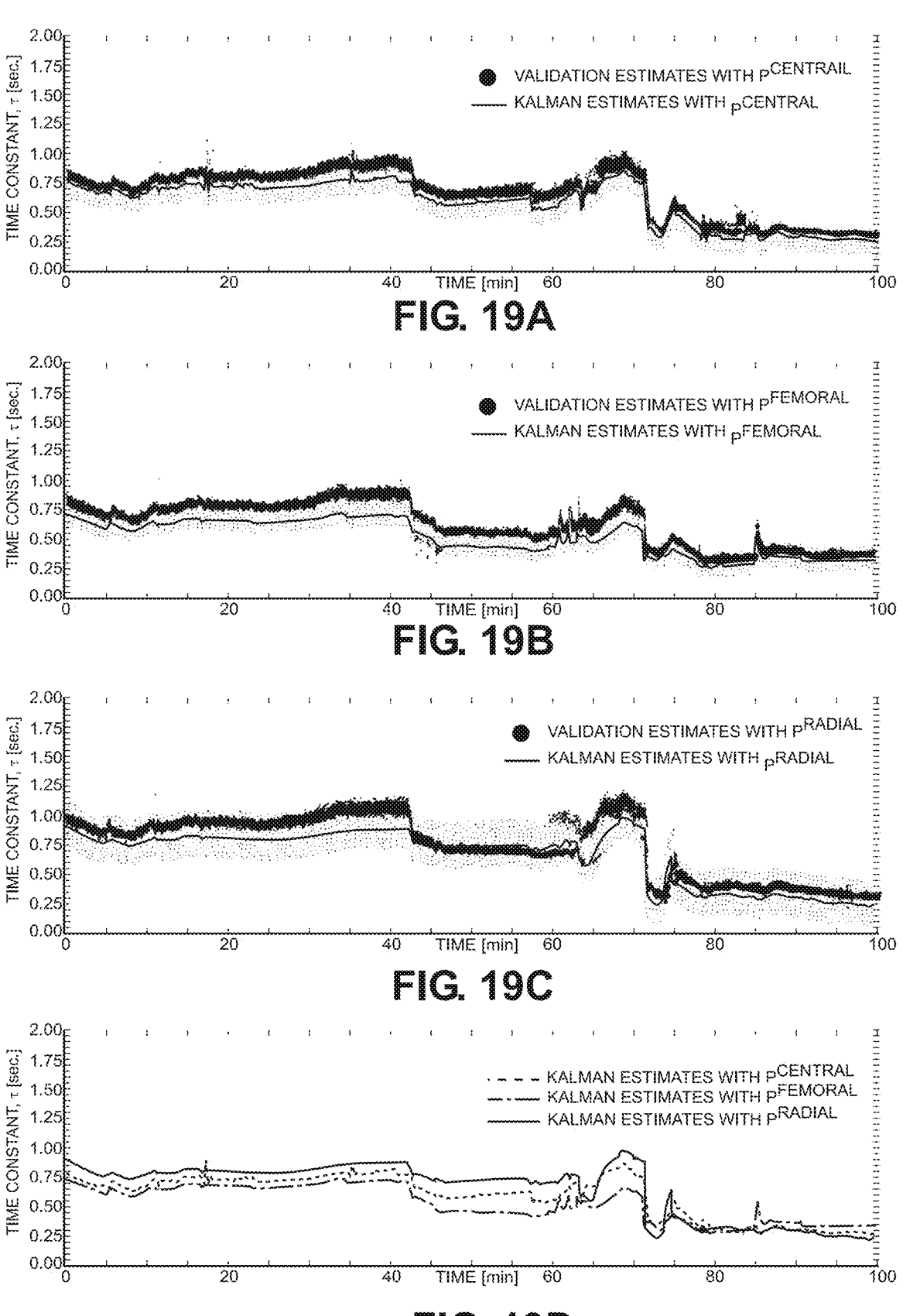

FIG. 19A shows, for Experiment 5, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 19B shows, for Experiment 5, a comparison of the beat-by-beat Kalman estimate of τ using the central ABP Waveform, $p^{femoral}$ versus the beat-by-beat validation estimate of τ using the central ABP waveform, $p^{femoral}$ and the AF Waveform, f.

FIG. 19C shows, for Experiment 5, a comparison of the beat-by-beat Kalman estimate of τ using the central ABP Waveform, $p^{radial}$ versus the beat-by-beat validation estimate of τ using the central ABP waveform $$\sigma^2_{[k|k-1]} = \sigma^2_{[k-1|k-1]} + \sigma^2_{\eta}, p^{radial}$$

and the AF Waveform, f.

FIG. 19D shows, for Experiment 5, a comparison of Kalman Estimates and Validation Estimates using Central, Radial, or Femoral ABP Waveforms. In this plot, the agreement of the Kalman estimates are shown for the best result using a central, radial, or femoral ABP waveform. The areas where the results are a lighter blue for the central Kalman estimate indicate the presence of a large dicrotic notch.

Figures 20A, 20B, 20C, 20D:
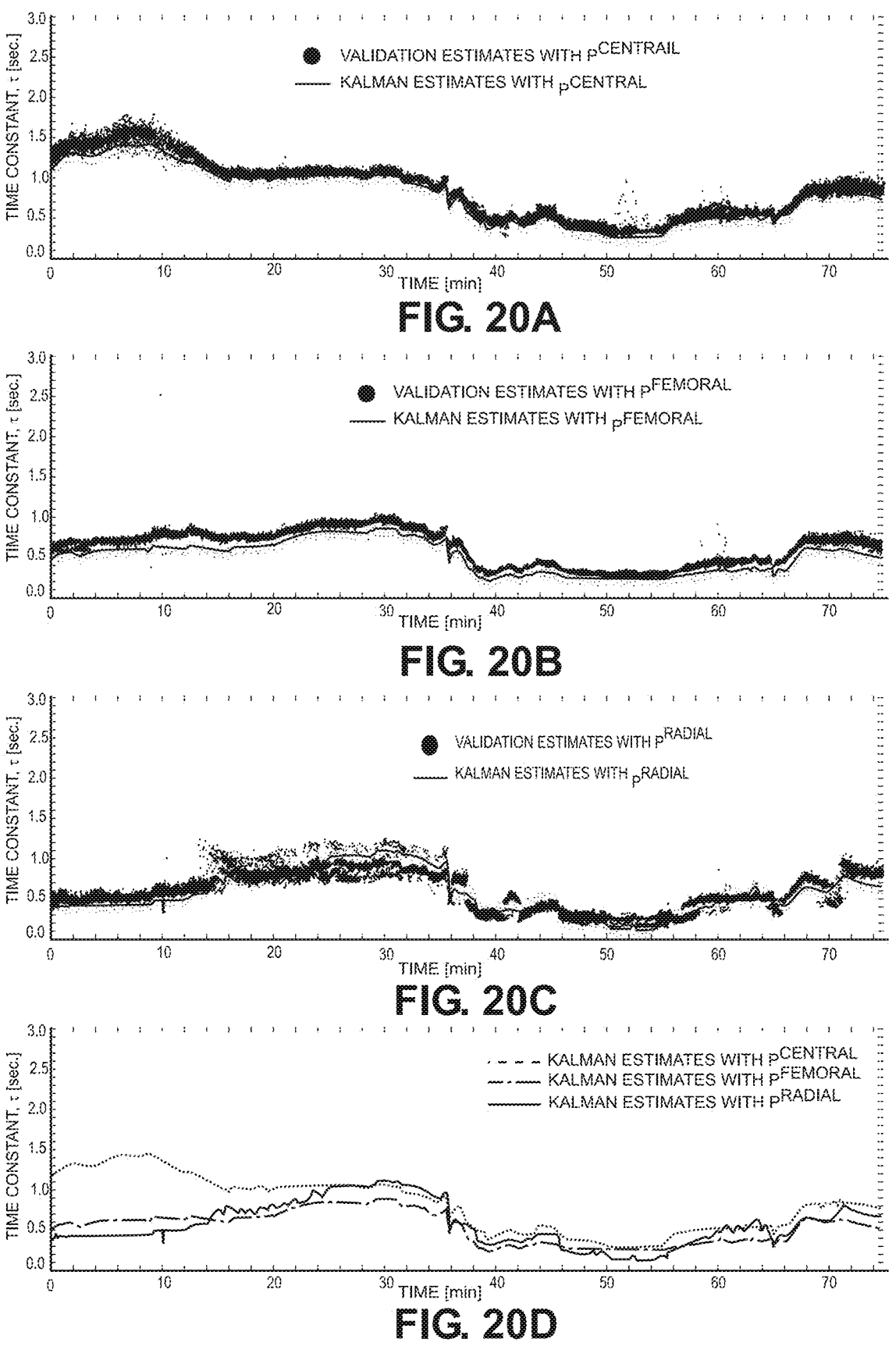

FIG. 20A shows, for Experiment 6, a comparison of the beat-by-beat Kalman estimate of τ using the central ABP Waveform, $p^{central}$ versus the beat-by-beat validation estimate of τ using the central ABP waveform, $p^{central}$ and the AF Waveform, f. The areas where the results are a lighter blue for the central Kalman estimate indicate the presence of a large dicrotic notch.

FIG. 20B shows, for Experiment 6, a comparison of the beat-by-beat Kalman estimate of $\tau$ using the central ABP Waveform, $p^{femoral}$ versus the beat-by-beat validation estimate of $\tau$ using the central ABP waveform, $p^{femoral}$ and the AF Waveform, f.

FIG. 20C shows, for Experiment 6, a comparison of the beat-by-beat Kalman estimate of $\tau$ using the central ABP Waveform, $p^{radial}$ versus the beat-by-beat validation estimate of $\tau$ using the central ABP waveform, $p^{radial}$ and the AF Waveform, f.

FIG. 20D shows, for Experiment 6, a comparison of Kalman Estimates and Validation Estimates using Central, Radial, or Femoral ABP Waveforms. In this plot, the agreement of the Kalman estimates are shown for the best result using a central, radial, or femoral ABP waveform. The areas where the results are a lighter blue for the central Kalman estimate indicate the presence of a large dicrotic notch.

DETAILED DESCRIPTION

All combinations of the foregoing concepts and additional concepts are discussed in greater detail below (provided such concepts are not mutually inconsistent) and are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

Figure 1:
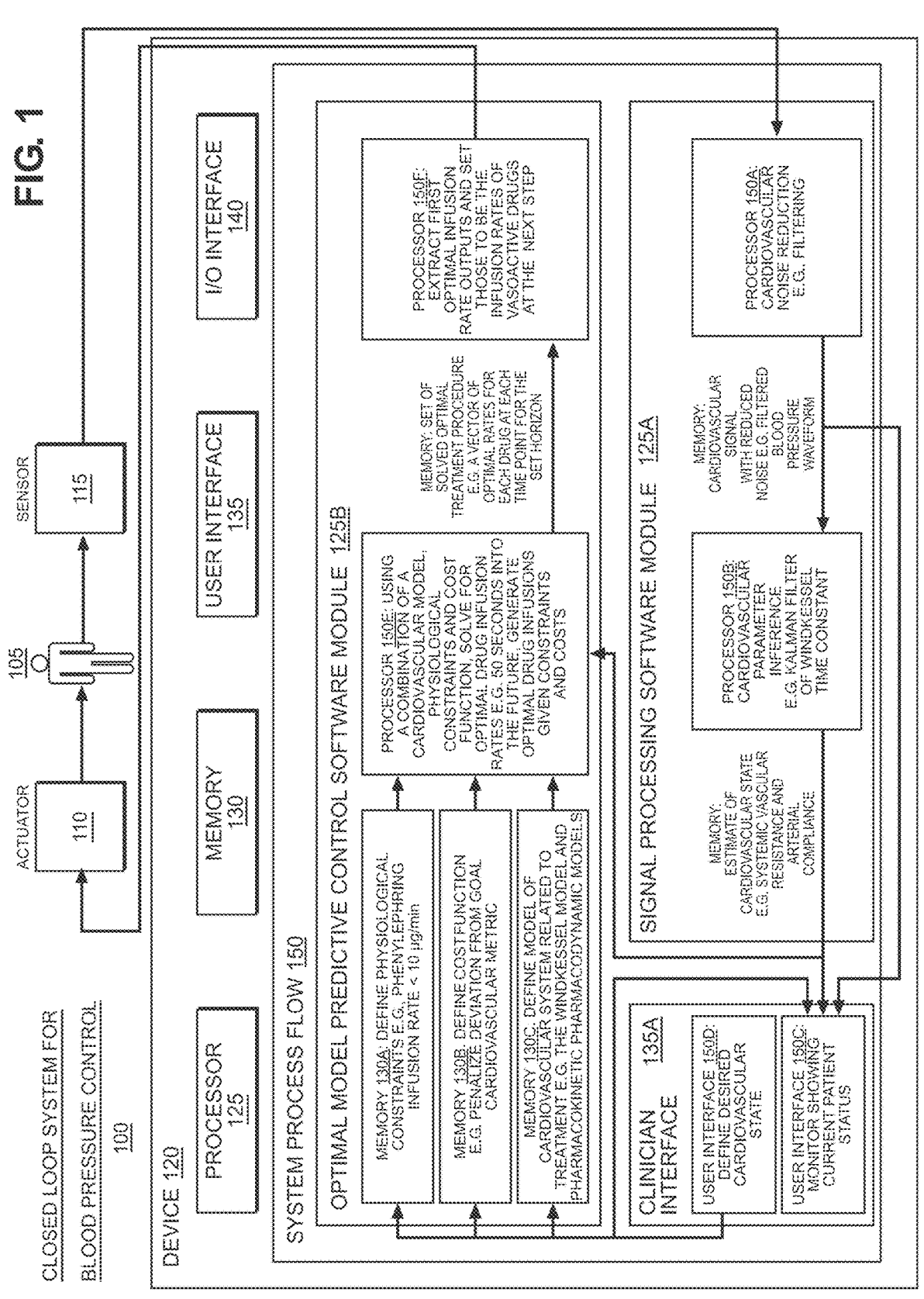

Aspects disclosed herein are generally directed to closed loop systems and methods for blood pressure control in a subject. FIG. 1 illustrates a hybrid system/method illustration 100 for blood pressure control in a user/subject 105. The user is coupled to an actuator or pump 110 that can be used to (e.g., intravenously) administer one or more substances for blood pressure control to the subject 105 such as, for example, a vasopressor for raising blood pressure via blood vessel constriction, a vasodilator for lowering blood pressure via blood vessel dilation, and/or the like. In some cases, the vasopressor can be one or more of epinephrine, norepinephrine, phenylephrine, ephedrine, droxidopa, isoproterenol, angiotensin II, and dobutamine. In some cases, the vasopressor is phenylephrine. In some cases, the vasodilator can be one or more of alprostadil, nitroglycerin, nicardipine, hydralazine, riociguat, vericiguat, nitroprusside, nesiritide, and minoxidil. In some cases, the vasodilator is nicardipine.

The user is also coupled to a blood pressure sensor 115 that can measure the blood pressure over time, e.g., as a blood pressure waveform, of the user. For example, the sensor 115 can be placed in an artery of the subject 105, such as via an arterial catheter. The pump 110 and the sensor 115 can be communicatively coupled to a device 120 which in turn can include a processor 125 and a memory/database 130. The processor 125 can be any suitable processing device configured to run and/or execute a set of instructions or code associated with the compute device(s). The processor can be, for example, a general purpose processor, a Field Programmable Gate Array (FPGA), an Application Specific Integrated Circuit (ASIC), a Digital Signal Processor (DSP), and/or the like. The memory/database 130 can encompass, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory/database can store instructions to cause the processor to execute processes and/or functions associated with the compute device(s).

As illustrated in FIG. 1, the device 120 also includes a user interface 135 such as, for example, a display screen of a personal computing device, such as a desktop computer, a laptop computer, a smartphone, or an electronic tablet. One such example of the interface 135 is a clinician interface 135a illustrated in FIG. 1, described in greater detail herein. The device 120 can also include an input/output interface 140 for receiving user input such as, for example, a mouse, a keypad, a touchscreen (e.g., also associated with the user interface 135), a stylus, a microphone, and/or the like.

As noted herein, the pump 110 and the sensor 115 can be communicatively coupled the processor 125. Example operation of the components of the system 100, i.e., of the pump 110, sensor 115, and the device 120 will be described herein with reference to method/process flow 150, also illustrated in FIG. 1. The various steps of the method 150 can be executed by the processor 125 based on computer-executable instructions stored in the memory/database 130, such as via, for example, one or more software modules executable by the processor. Generally, the processor 125 can receive, from the sensor 115, an indication of a measured blood pressure waveform of the subject 105. A signal processing module 125a of the processor 125 can process the blood pressure waveform at step 150a to remove noise via, for example, filtering using a low pass filter to remove high frequency noise. In some cases, the low pass filter can be a symmetric, finite impulse response (FIR) filter. In some cases, the low pass filter can be, for example, 1) a symmetric or anti-symmetric FIR filter or an Infinite Impulse Response (IIR) filter. In some cases, the low pass filter can be a separate analog circuit that is communicatively coupled to the processor 125 and be a combination of capacitors, inductors, and/or resistors. This reduced noise, filtered signal can then be stored to the memory 130 and also displayed via the user interface 135 at step 150c, such as to a clinician monitoring the subject 105, for example.

At step 150b, the module 125a can estimate, based on the filtered waveform, various cardiovascular parameters of the subject 105 such as, but not limited to, vascular or micro-circulation resistance, arterial compliance, stroke volume, and/or the like. These estimated parameters can be calculated by applying a Kalman filter to the blood pressure waveform measured/detected by the sensor 115. In some cases, the estimated parameters include a time constant parameter of the two-compartment Windkessel model (e.g., see examples 1-4 below), and this time constant parameter, estimated via the Kalman filter, in turn is used to estimate the other parameters of the two-compartment Windkessel model such as stroke volume, vascular resistance, and/or arterial compliance.

As illustrated in FIG. 1, at step 150c, the processor 125 can be configured to update the interface 135a to show blood pressure information for the user, such as the measured blood pressure waveform, the various parameters estimated at step 150b, and/or the like. At step 150d, which can be executed simultaneously/continuously with step 150c, the processor 125 can be configured to update the interface 135a based on input (e.g., via the I/O interface 140) from a clinician to reflect/illustrate a target blood pressure waveform or profile for the subject 105. In some cases, as illustrated in FIG. 1, the target blood pressure waveform can be retrieved from the memory 130. As an example, the target blood pressure waveform/profile can be specified in any suitable manner such as, for example, as having a mean arterial pressure of 100 mmHg, of having a vascular resistance of about 2 mmHg·min/l.

Figure 3:
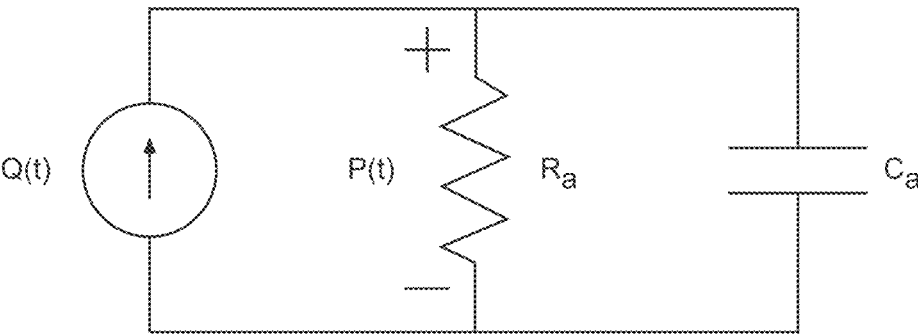

At step 150e, given an estimate of a cardiovascular state from the module 125a, the optimal model predictive control module 125b of the processor 125 is configured to generally calculate an estimated blood pressure waveform of the subject 105. This is done based on a circuit model of blood circulation in one or more blood vessels of the subject such as, for example, a circuit model of peripheral circulation as described in Example 1, where each major component of the peripheral circulation is represented by basic electrical components. In some cases, the circuit model is a two-element Windkessel Model that is illustrated in FIG. 3. The module 125b then calculates the estimated blood pressure waveform generally as follows. Firstly, an input blood flow parameter of the circuit model is set to be an impulse train. In some cases, each impulse of the impulse train can have an area has an area equivalent to the stroke volume that was estimated previously. Secondly, an arterial compliance parameter of the circuit model can be set to be time invariant (see Example 1). Generally, this parameter can be a representative, aggregate estimate of distention of arterial walls in the total peripheral circulation in response to an increase in pressure, with a significant contribution being from the larger arteries. Thirdly, a microcirculation resistance parameter of the circuit model can be set to be time invariant during a heartbeat, and to be time variant between each heartbeat (see Examples 1-4). Generally, this parameter can be a representative estimate of arterial resistance, arising primarily from microcirculation elements such as arterioles, capillaries, and venules. The estimated blood pressure waveform can then be calculated by solving the circuit model based on the input blood flow parameter, the arterial compliance parameter, the microcirculation resistance parameter, and the measured blood pressure waveform.

As also illustrated for step 150e, in some cases and in addition to the circuit model (sometimes also referred to as a first model), the optimal model predictive control module 125b of the processor 125 is configured to generate a model of metabolization for each of the one or more substances, i.e., a model of how the subject's body metabolizes that substance. For example, when the substances include a vasopressor and a vasodilator, the module 125b can generate/define a second model as a combination of a first two-compartment pharmacokinetic model for the first substance and a second two-compartment pharmacokinetic model for the second substance. The module 125b can further define a state space model based on the first model and the second model (e.g., see Example 3).

As also illustrated for step 150e, a suitable combination of parameters stored in the memory 130 can be employed to derive infusion rates for the patient 105. For example, FIG. 1 illustrates such parameters as relevant physiological constraints 130a, a cost function 130b, and/or a parameterized model 130c relating the cardiovascular system to drug input learned from sources other than patient 105. Processor 150e can be configured to employ this stored information to define conditions of optimality. Generally, physiological constraints stored in memory 130a can specify limits on model parameters, limits on treatment methods, and/or the like. Such possible constraints can include, but are not limited to, a maximum infusion rate for one or more of the substances, a constraint that a negative infusion rate is not permitted, a maximum frequency and/or rate of change of an infusion rate for one or more of the substances, and/or the like. Generally, the cost function 30b can describe the mathematical form of the desired behavior of optimized selection of treatment of patient 105. Such possible cost functions include, but are not limited to, a penalty on deviation from a stored desired cardiovascular state from input to User Interface 150d, penalty on the amount of treatment recommended and/or the like. Generally, when a specific form of a model of blood pressure dynamics or substance metabolism is defined as described herein, specific values parameterizing these models not specifically learned from patient 105 can be stored at 130c. For example, rate parameters of a specified model of metabolism previously learned from patient populations can be stored into memory 130.

At step 150e, the module 125b can be further configured to calculate, based on the estimated cardiovascular state (from step 150b), and the target cardiovascular state (from the user interface at step 150d), infusion rates for the one or more substances such as, for example, the first substance, the second substance, or for both. In some cases, the infusion rate(s) can be calculated based on the state space model. In some cases, the module 125b can be further configured to calculate the infusion rate(s) based on a model predictive control (MPC) framework and one or more constraints applied to the MPC framework. Generally, the MPC framework is an iterative closed loop method of process control while satisfying a set of constraints (see Example 1) previously stored in memory or input by user interface 150d. For example, the MPC framework can be configured to follow a set of convex constraints with a quadratic cost function and solved with convex optimization solvers.

At step 150f, the module 125b can be further configured to calculate, given the recommended optimal treatment procedure, the desired signal to send to the actuator 110 which in turn interfaces with the patient 105. Generally, this step will select the most recent recommended treatment. For example, a substance infusion rate for the most proximal time step could be selected to send to an infusion pump as an example actuator 110.

The processor 125 can be further configured to transmit an indication of the infusion rate(s) to the pump 110. The pump 125 can then modify an infusion rate of the first substance, of the second substance, or both, based on the one or more calculated infusion rates received from the processor 125.

Inventive aspects are further detailed below with respect to Examples 1-4. Generally, Example 1 describes an example closed-loop system for blood pressure control using phenylephrine and nicardipine. Example 2 describes an example approach to estimating the parameters of the circuit model as explained herein with respect to FIG. 1. Example 3 describes another example closed-loop system for blood pressure control with additional detail on the MPC framework described for step 150f. Example 4 describes an example approach to calculating the time constant parameter described for step 150b.

1. Example 1

This example is directed generally to a closed-loop system for blood pressure control with, for example, phenylephrine and nicardipine.

First, a model of the system where control is desired is presented. This model addresses the dynamics of how drug inputs, or the control input, impacts the cardiovascular system and the control of output blood pressure metrics. Specifically, a pharmacokinetic-pharmacodynamic (PK-PD) model is presented describing how blood pressure responds to vasoactive drugs, emphasizing the incorporation of mechanistic physiological models. Phenylephrine (PE) and nicardipine (NI) are chosen as the actuators and a PK model of said drugs is used for the state-space equation. From the two-element Windkessel model, explicit expressions for systolic pressure, diastolic pressure, and mean arterial pressure are derived, which are used for output equations. These modeling choices lead to interpretability of the drug-induced blood pressure dynamics in prospective experiments in terms of physiological mechanisms underlying the phenomena.

Second, a control framework is implemented with this system model. This model addresses the problem of building a controller that constrains the behavior of the cardiovascular system to a desired space. With feedback of the output blood pressure metrics in the form of an error between desired blood pressure metrics and observed blood pressure metrics, the controller will produce control inputs—drug infusion rates—which will push the plant to that desired space of behavior. A simulation experiment is presented to assess control feasibility with the presented system model. The simulation results indicate feasibility of the model-based control design in future experimental studies.

Previous work has sought to develop physiological closed-loop control systems to regulate blood pressure. Various approaches have implemented PID control, adaptive control, model predictive control (MPC), or fuzzy control, using non-mechanistic models of cardiac function and vascular physiology. Herein, non-mechanistic models refer to models which do not incorporate structure grounded explicitly in the understanding of real physiological processes. Many projects pursuing blood pressure control used a dynamic model of mean arterial pressure. This dynamic model represents the mean arterial pressure as the sum of a baseline pressure and changes to that baseline pressure from a drug, where the additive change in pressure term was characterized with a linear transfer function for sodium nitroprusside. Similarly, other studies used a system identification technique that assumes the relationship between drug infusion and effect is first-order plus a time delay. By not incorporating mechanistic descriptions of the cardiovascular system, these approaches lack interpretability, which creates a significant gap. As such, previous approaches have not been widely adopted, and no FDA approved PCLC system for blood pressure control appears to exist.

In this example, a PCLC system is presented that bridges this modeling gap by incorporating a mechanistic model of blood pressure dynamics and how these dynamics respond to vasoactive drugs. A drug PK model is incorporated, which describes how the body metabolizes a drug. A PD model is also incorporated based on the two-element Windkessel Model, which describes how a drug affects relevant physiological parameters. This example is distinguished over previous studies, in part, by focusing on building a control system with a model rather than solely estimating parameters of the model. Moreover, this framework is further distinguished by incorporating the Windkessel Model applied to a PCLC system for blood pressure management. Additionally, a vasopressor and vasodilator are incorporated, which means positive and negative control efforts are available.

1.1 System Model

This example seeks to control blood pressure using PE and NI. A model of the biological system in which control is desired is first developed. A mechanistic physiological model of the cardiovascular system is used—specifically the two-element Windkessel Model—in the development of the PD component.

The PK models of both of the actuators, PE and NI, are combined into a single state-space equation defined explicitly in Eq. 1.6. It is of the form, $$\dot{c} = Ac + Bu \qquad (1.1)$$

where u is a vector of drug inputs, PE and NI, and c is a vector of the compartmental concentrations of PE and NI in the body. The kinetic parameters for metabolism of PE and NI are in matrix A. PD modeling is incorporated through an output equation defined explicitly in Eq. 1.10. It is of the form, $$p = g(c). \qquad (1.2)$$

where p is a vector of relevant blood pressure metrics to be controlled.

1.1.1 Pharmacokinetics

To define the state-space equation, two-compartment PK models are considered for PE and NI, respectively, where the drug input is modeled as an intravenous infusion. In multi-compartmental PK models, each compartment represents groups of tissues within the body that have similar temporal profiles of drug distribution. It is assumed the tissues within a compartment have the same drug concentration. In two-compartment modeling, there is a central compartment and a peripheral compartment. The central compartment contains all tissues that have rapid or instantaneous drug uptake, including blood plasma. The peripheral compartment contains tissues, including fat and bone, which uptake the drug at a slower rate than the central compartment.

Figure 2:
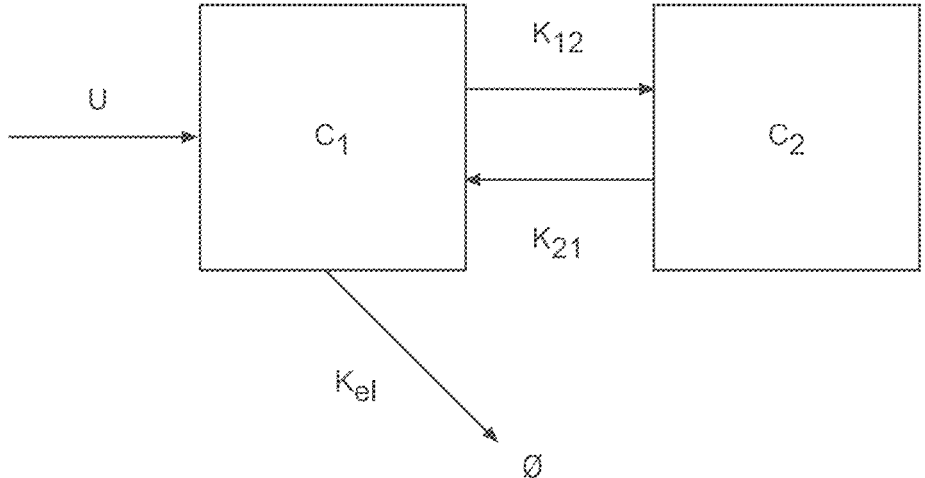

To define the state-space equation, the two-compartment PK model is first defined with intravenous infusion for both PE and NI. A general two-compartment PK model with intravenous infusion is shown in Eq. 1.3, $$\begin{bmatrix} \dot{c}_1 \\ \dot{c}_2 \end{bmatrix} = \begin{bmatrix} -k_{el} - k_{12} & k_{12} \\ k_{21} & -k_{21} \end{bmatrix} \cdot \begin{bmatrix} c_1 \\ c_2 \end{bmatrix} + \begin{bmatrix} \frac{1}{V_1} \\ 0 \end{bmatrix} \cdot u \qquad (1.3)$$

where $c_1$ in [mcg·L$^{-1}$] is the drug concentration in the central compartment, $c_2$ in [mcg·L$^{-1}$] is the drug concentration in the peripheral compartment, $k_{el}$ in [min$^{-1}$] is the elimination rate constant, $k_{12}$ in [min$^{-1}$] is the rate constant of distribution from the central compartment to the peripheral compartment, $k_{21}$ in [min$^{-1}$] is the rate constant of distribution from the peripheral compartment to the central compartment, $V_1$ in [L] is the volume of distribution of the central or first compartment, and u in [mcg·min$^{-1}$] represents the input infusion rate of a drug into the system. The constants defined in this model correspond to mass flow rate constants, which are traditionally estimated from empirical PK studies. As such, the formulation of Eq. 1.3 represents the dynamics of drug concentrations in the body in terms of mass flow rate constants. See Section 1.6.1 for the derivation of the translation from mass compartmental differential equations to concentration compartmental differential equations. This model is time-invariant. A graphical representation of this model of mass flow is shown in FIG. 2. In the ensuing discussion, the matrix representation (Eq. 1.1) of Eq. 1.3 is used for each of the drugs, PE and NI, to develop the PK-PD model incorporating the effects of both drugs.

The models can be assembled through use of drug-specific rate parameters. The PK parameters for the two-compartment model of PE are calculated from previous work. The calculated PK parameters are:

$$k_{12}^{PE} = .0922 \pm .0143 [\text{min}^{-1}], \; k_{21}^{PE} = .0139 \pm .0036 [\text{min}^{-1}],$$
$$k_{el}^{PE} = .0513 \pm .0078 [\text{min}^{-1}], \text{ and } V_1^{PE} = 41.2 \pm 14.6 [L].$$

$$V_1^{PE}$$

is the volume of distribution of the central compartment for PE. The mean values of these parameters are used in this example.

The PK parameters for the two-compartment model of NI are derived from previous work. The volume in the central compartment, given in $0.32\pm0.19$ in $[\text{L}\cdot\text{kg}^{-1}]$, is converted to $$V_1^{NI} = 27.3319$$

in [L] by multiplying by 85.41 in [kg], the average weight of the patient cohort. The following values are also derived:

$$k_{12}^{NI} \approx .0183 [\text{min}^{-1}], \; k_{21}^{NI} \approx .0019 [\text{min}^{-1}], \text{ and } k_{el}^{NI} \approx .0222 [\text{min}^{-1}].$$

See Section 1.6.4 for this derivation. It should be appreciated again these empirical values are mass flow rate constants.

In the following, the two PK models are assembled into a single state-space equation. Superscripts are used to indicate which variable corresponds to which drug. Further, c is explicitly defined to be, $$c = \left[ c_1^{PE}, c_2^{PE}, c_1^{NI}, c_2^{NI} \right]^T \tag{1.4}$$

and u to be, $$u = \left[ u^{PE}, u^{NI} \right]^T \tag{1.5}$$

With this notation, the drug-specific parameters, and 0 defined as a matrix of zeros (of appropriate size), the following can be defined, $$\dot{c} = \begin{bmatrix} A^{PE} & 0 \\ 0 & A^{NI} \end{bmatrix} c + \begin{bmatrix} B^{PE} & 0 \\ 0 & B^{NI} \end{bmatrix} u \tag{1.6}$$

where A is block-diagonal to reflect the assumption of non-interaction of PE and NI drug pharmacokinetics. See Section 1.6.2 for a more explicit definition of the PK component. Eq. 1.6 provides a complete state-space model in a compact form incorporating the two-compartment PK model for intravenous infusion of PE and the two-compartment PK model for intravenous infusion of NI.

1.1.2 Pharmacodynamics

This section presents a representation of the PD term. This may be achieved with the Windkessel model, which is a simple biophysical model of blood pressure dynamics in large arteries like the aorta, i.e., the main artery of the body. The Windkessel model represents these dynamics through the interplay of a compliant system of major vessels and a terminal vascular resistance from the microcirculation (arterioles, capillaries, and venules) while considering the venous system's resistive contributions as negligible. The original two-element Windkessel Model is used, as shown in FIG. 3.

From this circuit model, the differential equation found in Eq. 1.7 can be derived. The solution to this differential equation is a model of the blood pressure waveform.

$$\dot{P} + \frac{1}{R_a C_a} P = \frac{Q}{C_a} \tag{1.7}$$

where Q(t) in $[\text{ml}\cdot\text{sec}^{-1}]$ represents the volumetric inflow into the blood vessels from the heart. P(t) in [mmHg] represents the blood pressure in the aorta. $C_a$ in $[\text{ml}\cdot\text{mmHg}^{-1}]$ is the compliance of the body's major arteries. Compliance is defined as the ratio of change in volume to change in pressure. $R_a$ in $[\text{mmHg}\cdot\text{sec}\cdot\text{ml}^{-1}]$ is the terminal vascular resistance to blood flow from the microcirculation.

The input flow from the heart to the two-element model is represented as an impulse train. Each impulse has an area equivalent to the stroke volume represented as $\Delta V$ in [ml]. The stroke volume is the amount of blood volume pumped by the heart per beat. With this assumption of Q(t) as an impulse train, closed-form solutions can be found for the following: steady-state peak systolic pressure, $P_s$, mean arterial pressure, $P_m$, and minimal diastolic pressure, $P_d$. Steady-state, in this case, refers to the values of $P_s$, $P_d$, and $P_m$ that the system ultimately converges to given that $R_a$, $C_a$, and Q(t) remain of the same form. It should be appreciated steady state does not occur when $\dot{P}=0$, but when the oscillations reach a steady-state. This can be seen in FIG. 4 in between 10-50 [sec]. The derivation of these expressions can be found in Section 1.6.3. This derivation assumes $R_a$ is not time-varying.

From this derivation, the closed-form expressions for $P_s$, $P_d$, and $P_m$ are shown in Eq. 1.8, as follows, $$p = \begin{bmatrix} P_s \\ P_d \\ P_m \end{bmatrix} = \begin{bmatrix} \dfrac{\Delta V}{C_a} \dfrac{1}{1 - e^{-T/R_a C_a}} \\ P_s e^{-T/R_a C_a} \\ \dfrac{\Delta V}{T} R_a \end{bmatrix} \tag{1.8}$$

where T in [sec] represents the period—or time between beats—of the impulse train, Q(t). The period T can be related to the heart rate in $[\text{beats}\cdot\text{min}^{-1}]$ as T=60/HR. Eq. 1.8 thus provides closed form expressions of $P_s$, $P_d$, and $P_m$. Next, a relationship is defined between parameters of the Windkessel model and the effect-site concentration, $c_e$, of PE and NI.

PE is a pure al adrenergic agonist of the sympathetic system. Because of this, PE induces peripheral arterial vasoconstriction and ultimately an increase in systemic vascular resistance.

NI is a dihydropyridine calcium channel antagonist. Because of this, NI induces coronary and cerebral vasodilation and, ultimately, a decrease in systemic vascular resistance.

As such, the resistance term from the Windkessel model, $R_a$, can be defined to be a function of the effect-site concentration of PE, $$c_e^{PE},$$

and the effect site concentration of NI, $$c_e^{NI}.$$

A simplifying assumption is made that the relationship between the effect-site concentration of PE, $$c_e^{PE},$$

and $R_a$ is linear. It is also assumed the relationship between the effect-site concentration of NI, $$c_e^{NI},$$

and $R_a$ is linear. Because these drugs affect different receptors, it is assumed their effects are additive, $$R_a = g(c_e^{PE}, c_e^{NI}) = \beta^{PE} c_e^{PE} + \beta^{NI} c_e^{NI} + \beta_0 \qquad (1.9)$$

where $\beta^{PE}$ is the slope associated with the PE input, $\beta^{NI}$ is the slope associated with NI input, and $\beta_0$ is a baseline estimate of $R_a$. By replacing $R_a$ in Eq. 1.8 with the form of $R_a$ in Eq. 1.9, the PD model is obtained.

In the final step, the PK and PD models are linked together. This is accomplished by assuming the plasma concentration, $c_1$, of each drug is equal to their effect-site concentration, $c_e$, as follows, $$p = \begin{bmatrix} \frac{\Delta V}{C_a} \frac{1}{1 - e^{-T/(\beta^{PE} c_1^{PE} + \beta^{NI} c_1^{NI} + \beta_0) C_a}} \\ P_s e^{-T/(\beta^{PE} c_1^{PE} + \beta^{NI} c_1^{NI} + \beta_0) C_a} \\ \frac{\Delta V}{T}(\beta^{PE} c_1^{PE} + \beta^{NI} c_1^{NI} + \beta_0) \end{bmatrix} \qquad (1.10)$$

With this assumption, a fully specified PK-PD model in state-space form is obtained where Eq. 1.6 is the state-space equation and Eq. 1.8, with substitution of the functional form of $R_a$ in Eq. 1.9, is the output equation (Eq. 1.10).

With this state-space form, the PK and PD components are linked. In subsequent sections, this system model is used in an MPC framework to demonstrate control feasibility in a simulation setting.

1.2 Control Framework

To validate control feasibility with this system model formulation, an MPC framework is implemented. MPC is a closed-loop optimal control technique. MPC is chosen as it allows for incorporation of desired control constraints like bounded drug input rates. In general, MPC is structured in the following way: 1) identify current state, 2) optimize a trajectory from said state, 3) apply first optimal input to system, 4) let the dynamics evolve, and 5) repeat. To relate this to the application, synonymous steps are as follows: 1) identify current compartmental concentrations of drugs, 2) optimize a drug infusion input rate trajectory given a cost function relevant to the application, 3) choose the first optimal infusion rate, 4) simulate the model system dynamics forward (or let the biological system dynamics evolve) with this chosen input for some amount of time, and 5) repeat.

To implement this framework, the system is first discretized. See Section 1.6.5 for the derivation of this discretization method. The continuous time model is discretized by the zero-order hold assumption, which assumes the control inputs are held constant for each discrete time step (of duration h in [sec]). This allows for perfect integration of the dynamics, as follows, $$c[n+1] = e^{Ah} c[n] + A^{-1}(e^{Ah} - I) Bu[n] \qquad (1.11)$$

where A and B refer to those in Eq. 1.1 and further specified in Eq. 1.6. It is preferable that h is sufficiently small so that the discretization error is small. With the discretized model, Algorithm 1 is implemented in Python 3 with the MPC framework implemented using the Drake library.

---
Algorithm 1 Model Predictive Control
---
```
Initialize n = 0, i = 0
Set p_target, N, M, numSteps, Q, R, w, u_max
while i < numSteps do
  Observe p[n = iM]
  Estimate c[n = iM]
  Trajectory optimization to get u*, Eq.(4.12)
  u[iM, iM + 1, . . . , (i + 1)M - 1] ← u*[0]
  Apply control action, advance to i = i + 1
end while
```
---

In Algorithm 1, c[n] is the estimated system state vector at a discrete time point n, p[n] is the observed output vector, $p_{target}$ is the desired output vector, M is the number of discrete time units after a previous input rate switch before another input rate switch is possible, numSteps is the number of times that the trajectory optimization is run (iterated by i), and u* represents the optimal infusion rate values for PE and NI produced from the trajectory optimization. Note that the estimate of c[n] comes directly from the PK state-space equation as this is a noise free simulation. N, Q, R, w, and $u_{max}$ are components of the trajectory optimization cost function formulation detailed in Eq. 1.12, as follows, $$u^* = \underset{u[\cdot]}{\text{argmin}} \sum_n^{n+N-1} \frac{c^T Q c + u^T R u +}{w(p[n] - p_{target})^2} \quad Q = Q^T \geq 0, R = R^T \geq 0 \qquad (1.12)$$

$$\text{subject to} \quad c[n+1] = Ac[n] + Bu[n], \quad \forall\, n \in [iM, iM+1, \dots, iM + N - 1]$$

$$u[n] \leq u_{max} \quad \forall\, n \in [iM, iM+1, \dots, iM + N - 1]$$

-continued $$u[n] \geq 0 \qquad \forall\, n \in [iM, iM+1, \ldots, iM+N-1]$$

$$\begin{aligned} u[(i+k)M] = \\ u[(i+k)M+1] = \ldots = \\ u[((i+k+1)M-1)] \end{aligned} \qquad \forall\, k \in [0, \ldots, N/M-1]$$

As seen in Eq. 1.12, a cost function is chosen, which penalizes the following: 1) differences in the measured output vector, p, from $p_{target}$, 2) input drug infusion rates, u, and 3) compartmental concentrations of both PE and NI, c. Two constraints are introduced: 1) the inputs cannot have negative infusion rates, and 2) the inputs cannot exceed a certain infusion rate to ensure patient safety. Limitations are also imposed on how often the infusion rate can change in the final constraint, as state-of-the-art infusion devices can only change their rate every 5-30 [sec], depending on the device.

In Eq. 1.12, $u_{max}$ is the vector of maximum rates that the drugs can have for safety reasons, w is a vector of weights that may be sparse if only one aspect of blood pressure is controlled, N is the horizon or number of discrete time points forward considered when doing trajectory optimization, and M is the discrete time unit switching constraint described previously. h·M is the switching constraint in [sec]. Q and R depict the weights of cost on the states and inputs respectively. Q≥0 indicates that Q is positive semi-definite. With this, the MPC control framework is fully specified.

1.3 Control Simulation

In this section, a simulation experiment is presented, which implements MPC with the proposed PK-PD system model. For this experiment, the following is performed: 1) initialization, 2) Windkessel simulation until steady-state p, and 3) MPC control to regulate to the target blood pressure metric value.

Initialization To begin, a choice is made for the baseline parameters that comprise the Windkessel Model: T, $R_0$, $C_a$, and $\Delta V$. The parameters $C_a$, and $\Delta V$ are chosen to be constant physiologically plausible values. With these constant values, Eq. 1.8 is used to evaluate the desired $R_0$. $R_0$ indicates the initial value of $R_a$, as $R_a$ changes with the drug inputs. Next, a choice is made for the PD coefficients: $\beta^{PE}$, $\beta^{NI}$, $\beta_0$. A choice is also made for the value of h, which governs the discretization step. Following this, the linear state-space equation, Eq. 1.6, is assembled and discretized. Next, the parameters to run the MPC paradigm are initialized: M, N, $p_{target}$, $u_{max}$, Q, R, w, and numSteps.

Windkessel Simulation Following this, the Windkessel model is simulated until it reaches dynamics with which the $P_s$, $P_d$, and $P_m$ are stable. The continuous system simulation framework present in the Drake library is used.

MPC Control Following stabilization of the Windkessel dynamics, the MPC control framework is activated and the system begins to be regulated to the desired blood pressure metrics specified by $p_{target}$.

For this experiment, the baseline parameters of the Windkessel Model are chosen to be T=1 [sec], $C_a$=2.35 [ml·mmHg$^{-1}$], $R_0$=1.02 [mmHg·sec·ml$^{-1}$], and $\Delta V$=96 [ml]. These values approximately specify a simulated blood pressure waveform with $P_s$=120 [mmHg], $P_d$=80 [mmHg], and $P_m$=98.65 [mmHg]. Additionally, $\beta^{PE}$=0.2, $\beta^{NI}$=1.3, $\beta_0$=$R_0$, and h=1 [sec]. Additionally, M=5 [discretesteps], N=10·h·M [sec], $u_{max}$=[50,50]$^T$ [mcg·min$^{-1}$], Q=I, R=I, and numSteps=5 [optimizationruns]. See Section 1.6.7 for further details on the matrices Q, and R.

Figure 4:
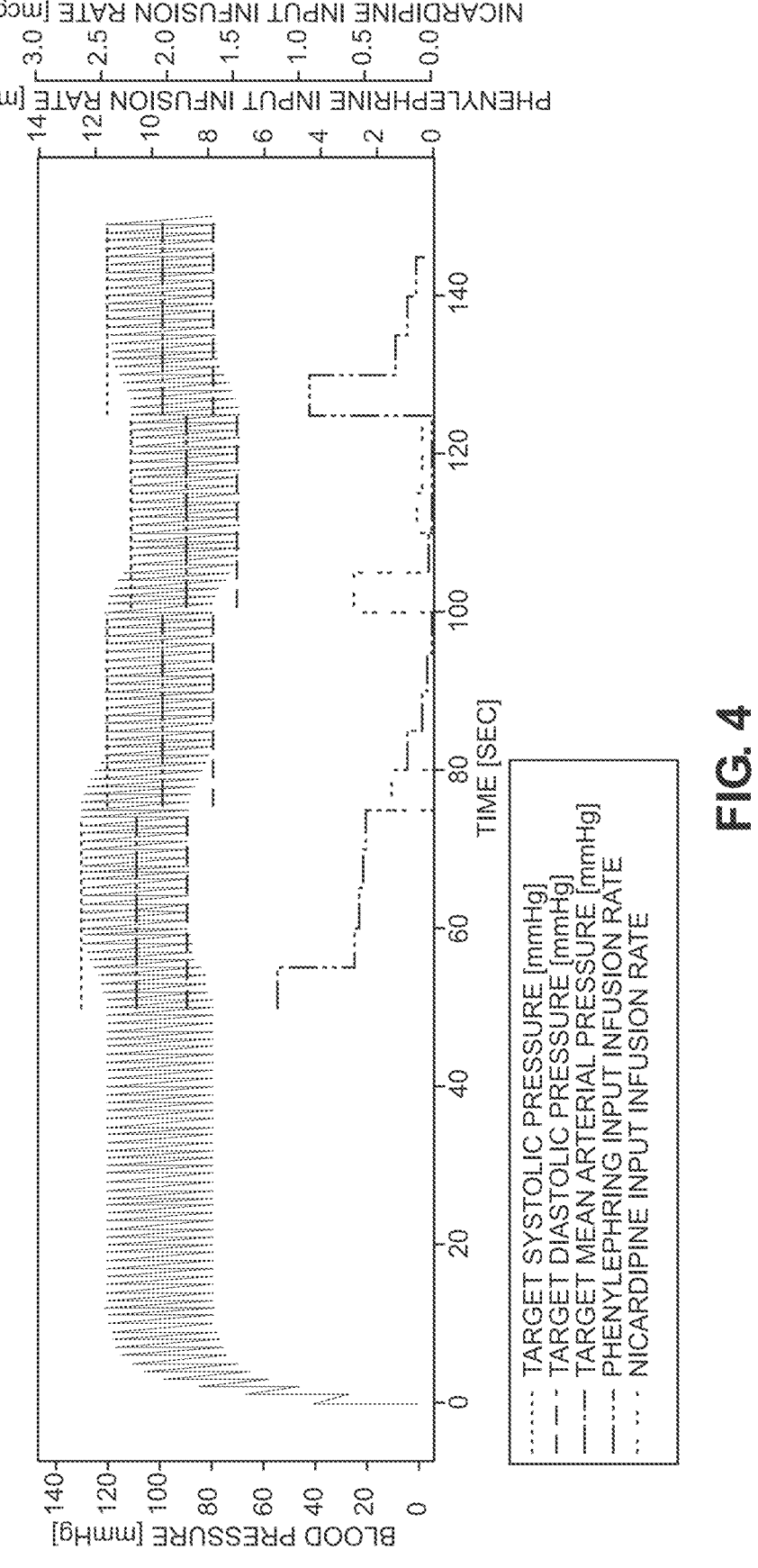

Next, the Windkessel model is simulated forward for 50 [sec]. Following this, the MPC controller is run four times. To start, c=0. Then, w is chosen to be w=[0,0,1]$^T$ meaning $P_m$ is fed back to the MPC controller with 25 [sec] epochs of target $P_m$ values 108.29, 98.16, 88.00, 98.16 [mmHg]. In other words, the waveform is controlled to be $P_m$=108.29 [mmHg] for 25 [sec], then to $P_m$=98.16 [mmHg] for 25 [sec], then towards the following values. FIG. 4 shows the simulation results for this experiment.

1.4 Discussion

In this example, a PK-PD model of the circulatory system's responses to vasoactive drugs, PE and NI, is presented. In this model, existing PK modeling techniques are linked with the two-element Windkessel model as a PD component. An MPC controller is implemented with this system model to show preliminary proof-of-concept control feasibility. This example provides a stable foundation which, with improvements discussed below, can be used in in vivo animal experiments. The use of mechanistic physiological models, specifically, can improve control efficacy beyond existing non-mechanistic approaches.

This example is distinguished over conventional approaches, in part, by the incorporation of mechanistic physiological models to describe the dynamics of the blood pressure waveform. First, the model includes two-compartment PK models of PE and NI. PK models use empirical observations of drug concentrations in the blood to provide principled descriptions of how a drug is processed in a biological system. These models can be used to better understand and predict the biological effects of the drugs used. Second, the use of the simple two-element Windkessel model is, likewise, beneficial as it captures much of the dynamics of the blood pressure waveform, while being simple enough to be compatible with computationally tractable optimal control techniques like MPC. Through use of the Windkessel model, personalization could be achieved by tuning the Windkessel model parameters, which have clear physiological interpretations and, thus, potential association with patient characteristics. These modeling choices lead to increased interpretability in the control framework.

The MPC control framework in this example also achieved desirable control results. The framework allowed for incorporation of pertinent safety constraints (such as strict limits of drug infusion rates), and mechanical constraints (such as limits on drug infusion switching rates). These constraints are desirable for this system to be viable in real-world applications.

Many additional control challenges accompany this problem class, which can be addressed with robust control, adaptive control, and system identification techniques. First, there is uncertainty in the model due to stochasticity in biological systems and modeling error. Second, the model parameters can vary for each patient and vary over time. Third, the current implementation of MPC is susceptible to steady-state error caused by sensitivity to mismatch between the system and the system model. Incorporating an integral term in the control design, however, can address this aspect. Finally, the current framework relies on the closed-form expressions for p found in Eq. 1.10. These expressions do not capture some transient behavior in the two-element Windkessel dynamics, as they were derived assuming all Windkessel parameters are time-invariant. Thus, in some implementations, the full two-element Windkessel dynamics can be incorporated in the MPC formulation, leading to a non-standard control problem.

Additionally, several modeling assumptions are made in this example. While the Windkessel model describes the general dynamics of the blood pressure waveform of large arteries like the aorta, it does not describe the intricacies of varied blood pressure waveform dynamics along the arterial tree. Next, the modeling assumption that PE and NI do not interact pharmacokinetically or pharmacodynamically is made. This may be untrue, especially if they share a metabolic pathway. In the simulation experiments, it is assumed that all parameters excluding $R_a$ are not time-varying. If this variability over time is not accounted for, variable system and model mismatch can occur. Thus, this assumption can be relaxed as warranted in animal experiments.

A PK-PD model of PE and NI effects on a blood pressure waveform modeled with the two-element Windkessel model is presented. A standard MPC controller is disclosed for this model and provides a basic simulation of control.

1.5 Supplemental Information for the Two-Element Windkessel Model

In the following, additional details on the two-element Windkessel Model are presented.

1.5.1 Derivation of Two-Element Windkessel Dynamical Equation

In the following, a derivation of the differential equation for the two-element Windkessel Model shown in Eq. 1.7 is presented. The relevant variables for this derivation are referenced in FIG. 3.

The derivation begins with Eq. 2.1. This equation states that the change in arterial blood volume, $\dot{V}_a$, in [ml·sec$^{-1}$], is equivalent to the difference between the volumetric inflow into the arteries, $Q(t)$ in [ml·sec$^{-1}$], and the flow out of the arteries, $Q_{out}(t)$ in [ml·sec$^{-1}$], into the microcirculation, as follows, $$\dot{V}_a(t) = Q(t) - Q_{out}(t) \tag{2.1}$$

$Q_{out}(t)$ is an analog to current. It is the current moving through the resistor branch. So, using Ohm's law, where voltage is equal to current times resistance, the current analog, $Q_{out}(t)$, is related to the voltage analog, $P(t)$, and the resistance, $R_a$, as follows, $$Q_{out}(t) = \frac{P(t)}{R_a} \tag{2.2}$$

In the two-element Windkessel model is a compliance term, which represents the ability of a vessel to distend and increase volume with an increase in the difference between inside versus outside pressure pressure. Compliance is an analog to capacitance in the equivalent circuit model. Compliance relates change in the arterial blood volume to arterial pressure difference. The circuit analog equation known as Ohm's Law for capacitors can be used to get the following equation, $$C_a\dot{P}(t) = \dot{V}_a(t) \tag{2.3}$$

Eqs. 2.2 and 2.3 can be substituted into Eq. 2.1 and then rearranged to get Eq. 2.4, as follows, $$C_a\dot{P}(t) = Q(t) - \frac{P(t)}{R_a} \tag{2.4}$$

To write this in standard form, Eq. 2.4 is rearranged to get Eq. 2.5, $$\dot{P} + \frac{1}{R_aC_a}P = \frac{Q}{C_a} \tag{2.5}$$

This equation is equivalent to Eq. 1.7.

1.5.2 Solving for a Homogeneous Solution of the Two-Element Windkessel Equation

A homogeneous solution to the differential equation in Eq. 2.5 (also Eq. 1.7) can be obtained by first assuming the forcing function, $Q(t)$, is zero, as follows, $$\frac{dP}{dt} + \frac{1}{R_aC_a}P = 0 \tag{2.6}$$

Now, the separable differential equation can be solved through traditional differential equation techniques. This equation is first separated into portions corresponding to the P and t components and then both sides are integrated, as follows, $$\int \frac{1}{P}dP = \int \frac{-1}{R_aC_a}dt \tag{2.7}$$

This integration gives the following, $$\ln(P) = \frac{-t}{R_aC_a} + c_0 \tag{2.8}$$

Each side is adjusted by using an exponential, as follows, $$P = \exp\left(\frac{-t}{R_aC_a} + c_0\right) \tag{2.9}$$

Next, using exponential properties, the function is simplified, as follows, $$P = c\exp\left(\frac{-t}{R_aC_a}\right) \tag{2.10}$$

If $\tau = R_aC_a$ and c as a constant (where c is specified by the initial condition of the system once it enters diastole), Eq. 2.10 becomes the following, $$P = ce^{-\frac{t}{\tau}} \tag{2.11}$$

The homogeneous solution represents the instance where there is no blood flow from the heart. This is diastole, i.e., when the heart is not pumping, but, instead, refilling with blood. c is specified by the initial condition of the system once it enters diastole.

1.6 Supplemental Information for Theoretical Development of a Closed-Loop System for Blood Pressure Control with Phenylephrine and Nicardipine In the following, additional details on the model for the closed-loop system for blood pressure control discussed in Sections 1.1-1.4 are presented.

1.6.1 Derivation of Pharmacokinetic Concentration Differential Equations with Mass Flow Rate Constants In the literature for PK modelling, the rate parameters, which are learned from experimental data, are mass flow rate constants. In the following, a derivation of the formulation for the differential equation is presented where compartmental concentrations, c, are the state variables and mass flow rate constants make up the state-space matrices.

The derivation begins by using traditional equations for compartmental drug mass dynamics with mass flow rate constants for a general drug, which is shown below as follows, $$\dot{x} = \begin{bmatrix} -k_{el} - k_{12} & k_{21} \\ k_{12} & -k_{21} \end{bmatrix} x + \begin{bmatrix} 1 \\ 0 \end{bmatrix} u \tag{3.1}$$

where $x_1$ in [mcg] is the drug mass in the central compartment, $x_2$ in [mcg] is the drug concentration in the peripheral compartment, and u in [mcg·min$^{-1}$] represents the input infusion rate of the drug into the system. Further, $x=[x_1,x_2]^T$.

The differential equations corresponding to Eq. 3.1 are as follows, $$\frac{dx_1}{dt} = -k_{12}x_1 - k_{el}x_1 + k_{21}x_2 + u \tag{3.2}$$

$$\frac{dx_2}{dt} = k_{12}x_1 - k_{21}x_2 \tag{3.3}$$

The mass flow rate constants in Eqs. 3.2 and 3.3 correspond to the rate at which mass flows in and out of drug compartments. For example, $k_{12}$ in [min$^{-1}$] describes the rate of flow of the drug mass out of compartment 1, the central compartment, and into compartment 2, the peripheral compartment, while $k_{el}$ in [min$^{-1}$] describes the rate of mass flow from the compartment 1 out of the body, also known as the elimination rate constant. $V_1$ in [L] is the volume of distribution for the drug in the central or first compartment.

In this derivation, the differential equations are defined in terms of compartmental concentration, c, rather than compartmental mass, x. It should be appreciated experimentally derived mass flow rate constants can be used to define these differential equations, but the intuition may be less clear. To avoid confusion, the mass flow rate constants are explicitly derived for the concentration differential equations below. First, Eq. 2.2 is divided by $V_1$, and Eq. 2.3 is divided by $V_2$ or the volume of distribution for the drug in the peripheral or second compartment, as follows, $$\frac{d\frac{x_1}{V_1}}{dt} = -k_{12}\frac{x_1}{V_1} - k_{el}\frac{x_1}{V_1} + \frac{k_{21}}{V_1}x_2 + \frac{u}{V_1} \tag{3.4}$$

$$\frac{d\frac{x_2}{V_2}}{dt} = \frac{k_{12}}{V_2}x_1 - k_{21}\frac{x_2}{V_2} \tag{3.5}$$

The following is defined, $$c_1 = \frac{x_1}{V_1} \tag{3.6}$$

-continued $$c_2 = \frac{x_2}{V_2} \tag{3.7}$$

By substituting Eqs. 3.6 and 3.7 into Eqs. 3.4 and 3.5, the following is obtained, $$\frac{dc_1}{dt} = -k_{12}c_1 - k_{el}c_1 + \frac{k_{21}}{V_1}x_2 + \frac{u}{V_1} \tag{3.8}$$

$$\frac{dc_2}{dt} = \frac{k_{12}}{V_2}x_1 - k_{21}c_2 \tag{3.9}$$

Eqs. 3.8 and 3.9 are then multiplied by terms equal to 1 (e.g., $V_1/V_1$, $V_2/V_2$), as follows, $$\frac{dc_1}{dt} = -k_{12}c_1 - k_{el}c_1 + \frac{k_{21}}{V_1}\frac{V_2}{V_2}x_2 + \frac{u}{V_1} \tag{3.10}$$

$$\frac{dc_2}{dt} = \frac{k_{12}}{V_2}\frac{V_1}{V_1}x_1 - k_{21}c_2 \tag{3.11}$$

Eqs. 3.10 and 3.11 can be simplified further given the following observations. When a system is at steady state, then following is true, $$\frac{x_1}{V_1} = \frac{x_2}{V_2} \tag{3.12}$$

and, $$k_{12}x_1 = k_{21}x_2 \tag{3.13}$$

Substituting Eq. 3.13 into Eq. 3.12 for $x_1$ yields the following, $$k_{12}\frac{x_2 V_1}{V_2} = k_{21}x_2 \tag{3.14}$$

Dividing by $x_2$ and rearranging, the following is obtained, $$k_{12}V_1 = k_{21}V_2 \tag{3.15}$$

Eq. 3.15 is substituted into Eqs. 3.10 and 3.11 to obtain the following, $$\frac{dc_1}{dt} = -k_{12}c_1 - k_{el}c_1 + \frac{\frac{k_{12}V_1}{V_2}}{V_1}\frac{V_2}{V_2}x_2 + \frac{u}{V_1} \tag{3.16}$$

$$\frac{dc_2}{dt} = \frac{\frac{k_{21}V_2}{V_1}}{V_2}\frac{V_1}{V_1}x_1 - k_{21}c_2 \tag{3.17}$$

Eqs. 3.16 and 3.17 can be further simplified as follows, $$\frac{dc_1}{dt} = -k_{12}c_1 - k_{el}c_1 + k_{12}\frac{x_2}{V_2} + \frac{u}{V_1} \tag{3.18}$$

$$\frac{dc_2}{dt} = k_{21}\frac{x_1}{V_1} - k_{21}c_2 \tag{3.19}$$

Upon substituting in $c_1$, and $c_2$, the following is obtained, $$\frac{dc_1}{dt} = -k_{12}c_1 - k_{el}c_1 + k_{12}c_2 + \frac{u}{V_1} \tag{3.20}$$

$$\frac{dc_2}{dt} = k_{21}c_1 - k_{21}c_2 \tag{3.21}$$

This leads to the formulation for compartment concentration dynamics, as follows, $$\dot{c} = \begin{bmatrix} -k_{el} & -k_{12} & k_{12} \\ k_{21} & & -k_{21} \end{bmatrix} c + \begin{bmatrix} \frac{1}{V_1} \\ 0 \end{bmatrix} u \tag{3.22}$$

where $c_1$ in [mcg·L$^{-1}$] is the drug mass in the central compartment, $c_2$ in [mcg·L$^{-1}$] is the drug concentration in the peripheral compartment, $c=[c_1, c_2]^T$ is a vector of the compartmental concentrations for compact notation, $V_1$ in [L] is the volume of distribution for the drug in the central or first compartment, and $u$ in [mcg·min$^{-1}$] represents the input infusion rate of the drug into the system. The only difference between the state-space matrices in this revised equation, Eq. 3.22, and the original mass differential equation, Eq. 3.1, is that the A matrix is transposed.

1.6.2 Explicit Pharmacokinetic Component

In this section, a more explicit description of the pharmacokinetic (PK) component in the model is presented. As discussed in Section 1.1, the PK components of the model are combined into a single state-space equation. To define the state-space equation, a two-compartment model for both phenylephrine (PE) and nicardipine (NI) is used as a starting point. First, the general form of the PE PK model is as follows, $$\dot{c}^{PE} = \begin{bmatrix} \square & \square \\ \square & \square \end{bmatrix}\begin{bmatrix} -k_{el}^{PE} & -k_{12}^{PE} & k_{12}^{PE} \\ k_{21}^{PE} & & -k_{21}^{PE} \end{bmatrix} c^{PE} + \begin{bmatrix} \frac{1}{V_1^{PE}} \\ 0 \end{bmatrix} u^{PE} = \tag{3.23}$$

$$A^{PE}c^{PE} + B^{PE}u^{PE}$$

where $$c_1^{PE}$$

in [mcg·L$^{-1}$] is the drug concentration of PE in the central compartment, $$c_2^{PE}$$

in [mcg·L$^{-1}$] is the drug concentration of PE in the peripheral compartment, $$V_1^{PE}$$

in [L] is the volume of distribution for PE of the central or first compartment, and $u^{PE}$ in [mcg·min$^{-1}$] represents the input infusion rate of PE into the system. The rate constants are mass flow rate constants. Please refer to section 1.6 for a description of how mass flow rate constants can be used in a concentration dynamic equation. Second, the general form of the NI PK model is as follows, $$\dot{c}^{NI} = \begin{bmatrix} -k_{el}^{NI} & -k_{12}^{NI} & k_{12}^{NI} \\ k_{21}^{NI} & & -k_{21}^{NI} \end{bmatrix} c^{NI} + \begin{bmatrix} \frac{1}{V_1^{NI}} \\ 0 \end{bmatrix} u^{NI} = A^{NI}c^{NI} + B^{NI}u^{NI} \tag{3.24}$$

where $$c_1^{NI}$$

in [mcg·L$^{-1}$] is the drug concentration of NI in the central compartment, $$c_2^{NI}$$

[mcg·L$^{-1}$] is the drug concentration of NI in the peripheral compartment, $$V_1^{NI}$$

in [L] is the volume of distribution for NI of the central or first compartment, and $u^{NI}$ [mcg·min$^{-1}$] represents the input infusion rate of NI into the system. Once again, the rate constants are mass flow rate constants. Please refer to Section 1.6 for a description of how mass flow rate constants can be used in a concentration dynamic equation.

The two PK models are now assembled into a single state-space equation. The vector c is defined, as in Section 1.1, to be, $$c = \begin{bmatrix} c_1^{PE}, c_2^{PE}, c_1^{NI}, c_2^{NI} \end{bmatrix}^T \tag{3.25}$$

and u to be, $$u = \begin{bmatrix} u^{PE}, u^{NI} \end{bmatrix}^T \tag{3.26}$$

So, the full state-space equation becomes, $$\dot{c} = \begin{bmatrix} -k_{el}^{PE} & -k_{12}^{PE} & k_{12}^{PE} & 0 & & 0 \\ k_{12}^{PE} & & -k_{12}^{PE} & 0 & & 0 \\ 0 & & 0 & -k_{el}^{NI} & -k_{12}^{NI} & k_{12}^{NI} \\ 0 & & 0 & & k_{12}^{NI} & -k_{12}^{NI} \end{bmatrix} c + \begin{bmatrix} \frac{1}{V_1^{PE}} & 0 \\ 0 & 0 \\ 0 & \frac{1}{V_1^{NI}} \\ 0 & 0 \end{bmatrix} u \qquad (3.27)$$

If 0 is defined to be a matrix of zeros with appropriate dimensions, this equation can be rewritten as follows, $$\dot{c} = \begin{bmatrix} A^{PE} & 0 \\ 0 & A^{NI} \end{bmatrix} c + \begin{bmatrix} B^{PE} & 0 \\ 0 & B^{NI} \end{bmatrix} u \qquad (3.28)$$

Eq. 3.28 represents the complete state-space model in a more compact form. This is equivalent to Eq. 1.6.

Figure 5:
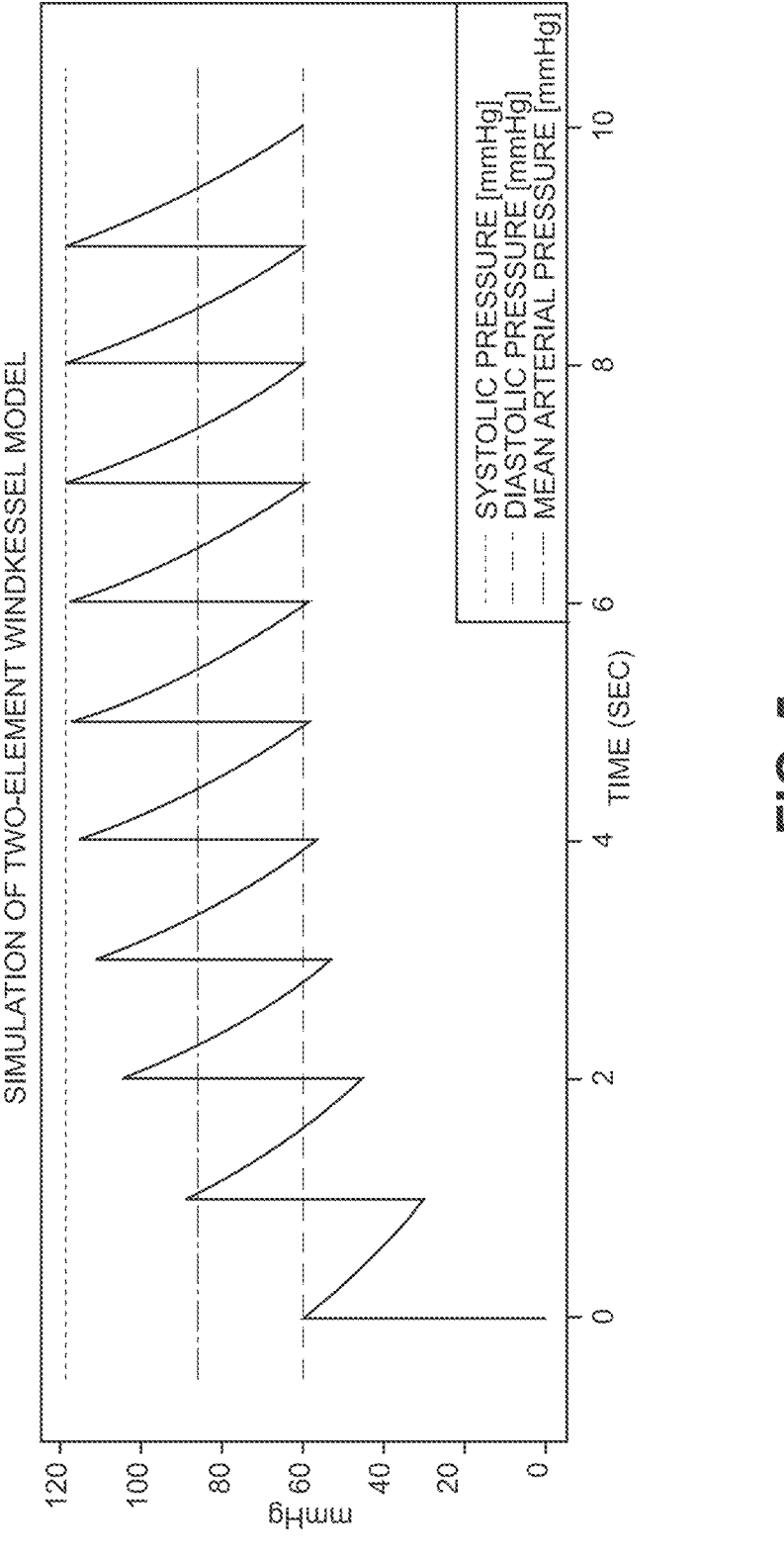

1.6.3 Derivation of Steady-State Systolic, Mean, and Diastolic Arterial Blood Pressure Assuming Stationary $R_a$ In this section, a derivation is presented of the steady-state systolic pressure, $P_s$, diastolic pressure, $P_d$, and mean arterial pressure, $P_m$. These steady-state pressures are defined to be the constant values that the Windkessel model arrives at after an appropriate settling time. These values are illustrated in FIG. 5. Recall the solution to the differential equation describing the dynamics of the two-element Windkessel model describes the blood pressure waveform in the aorta, or any large compliant artery in the peripheral circulation.

It is assumed at the beginning that there is no volume in the peripheral circulation at t=0. First, the heart will deposit its initial stroke volume, $\Delta V$, into the compliant system of major vessels. Analogous to electrical circuits, this is the moment of charging the capacitor, as shown in the following equation, $$\Delta V = \Delta P C_a \qquad (3.29)$$

The stroke volume is equal to the pressure difference times the compliance. In a circuit analogy, this is a traditional capacitor equation relating charge, voltage potential, and capacitance. It is assumed that the blood volume pumped from the heart into the systemic circulation takes the form of an impulse train. Given this, at time t=0, the pressure is increased to $\Delta V/C_a$. It is further assumed that each additional volume is transferred to the arterial compliance instantaneously; as such, at t=0$^+$, an exponential decay of the pressure in the aorta is observed from the decreasing volume in the arterial compliance. This behavior is specified by the homogeneous solution of Eq. 1.7. This general homogeneous solution derivation is specified in Section 1.6.

This blood volume then leaves through the peripheral resistance, $R_a$, of the microcirculation. Before the volume is depleted, the heart pumps another stroke volume impulse, $\Delta V$, into the system, which raises the pressure by $\Delta V/C_a$. After some time of this push and pull from impulses of stroke volume and subsequent releases of blood volume through the systemic circulation, the system will reach an equilibrium.

This equilibrium time is defined to occur when the amount of pressure depleted by the flow resistance, $R_a$, is equivalent to the amount of pressure, $\Delta V/C_a$, resulting from dumping a stroke volume of $\Delta V$ into the compliant aorta.

In reference to the homogeneous solution from Section 1.6, when the heart is not pumping any blood volume into the system, the system is in diastole, which is described by Eq. 2.11.

If the system is assumed to be at the steady-state, as described above, the initial condition for the exponential decay of pressure found in diastole is P(0)=$P_s$, where $P_s$ is the systolic pressure. Additionally, $\tau$ is defined as $\tau=R_a C_a$. Based on the initial condition and T being the time between each heart volume impulse, the following can be defined, $$P_d = P_S e^{-\frac{T}{\tau}} \qquad (3.30)$$

The pressure decrease from $P_s$ to $P_d$, which is equivalent to $\Delta V/C_a$ at steady-state, would be, $$\frac{\Delta V}{C_a} = P_S \left(1 - e^{-\frac{T}{\tau}}\right) \qquad (3.31)$$

From this, $P_s$ can be solved as follows, $$P_S = \frac{\Delta V}{C_a} \frac{1}{\left(1 - e^{-\frac{T}{\tau}}\right)} \qquad (3.32)$$

A closed-form expression for the pressure in the aorta over time can then be written during this equilibrium stage. The definition in Eq. 3.33 holds in the interval between $nT \le t < (n+1)T$, where n is indicating the beat that is referenced with the count starting at 0, $$P(t) = P_s e^{-\frac{t-nT}{\tau}} \qquad (3.33)$$

$P_s$ is then replaced with its explicit form, as follows, $$P(t) = \frac{\Delta V}{C_a} \frac{e^{-\frac{t-nT}{\tau}}}{\left(1 - e^{-\frac{T}{\tau}}\right)} \qquad (3.34)$$

A closed-form expression of the mean arterial pressure can also be defined as a product of $R_a$ and the average flow or cardiac output, $\Delta V/T$, as follows, $$P_a = \frac{\Delta V}{T} R_a \qquad (3.35)$$

It should be appreciated this derivation for the closed-form expressions for $P_s$, $P_d$, and $P_a$ is assuming that $R_a$ is not time-varying. In other implementations, the control framework can be implemented with solutions for these steady-state metrics where $R_a$ is time-varying.

1.6.4 More Explicit Derivation of Nicardipine Pharmacokinetic Parameters

As discussed in Section 1.1, the PK parameters for the two-compartment model of NI are derived with the following values:

$$k_{12}^{NI} \approx .0183\left[\text{min}^{-1}\right], \ k_{21}^{NI} \approx .0019\left[\text{min}^{-1}\right], \text{ and } k_{el}^{NI} \approx .0222\left[\text{min}^{-1}\right].$$

A more detailed derivation of these values is presented below.

It is assumed the mean values are, for the following parameters: $t_{1/2\alpha}=16.7\pm10.8$, the distribution half-life in [min], and $t_{1/2\beta}=11.49\pm5.76$, the elimination half-life in [hr], and Cl=0.428±0.119, clearance in [L/hr·kg], and $V_1=0.32\pm0.19$, the volume of distribution in the central compartment in [L/kg]. From these parameters, $k_{12}$, $k_{21}$, and $k_{el}$ can be derived using the following, $$\alpha = \frac{.693}{t_{1/2\alpha}} \tag{3.36}$$

$$\beta = \frac{.693}{t_{1/2\beta}} \tag{3.37}$$

$$k_{21} = \frac{\alpha\beta}{k_{el}} \tag{3.38}$$

$$k_{12} = \alpha + \beta - k_{el} - k_{21} \tag{3.39}$$

$$k_{el} = \frac{Cl}{V_1} \tag{3.40}$$

Eqs. 3.36-3.40 can be combined together to produce three equations and three unknowns. Thus, the desired parameters can be solved with the mean values of $t_{1/2\beta}$, resulting in $k_{12}\approx0.0183$ [min$^{-1}$], $k_{21}\approx0.0019$ [min$^{-1}$], and $k_{el}\approx0.0223$ [min$^{-1}$].

1.6.5 Discretization of Linear System Model Using Zero Order Hold Assumption In this section, additional details are presented regarding the discretization of a continuous time system given its state-space model representation, as follows, $$\dot{x} = Ax + Bu \tag{3.41}$$

For instance, a linear dynamic equation of the form shown in Eq. 3.41 is discretized by assuming that the control inputs, u, are held constant for each discrete time step. Based on the chosen discretization framework, the dynamics can be integrated perfectly regardless of discretization step. This is valid if the zero order hold assumption applies to the input being used. In the following, x is used rather than c for generalizability to systems outside of this present disclosure where state variables are traditionally referred to as x. Thus, $$x[n+1] = x[n] + \int_{kT}^{kT+T} [Ax(t) + Bu]dt \tag{3.42}$$

$$= e^{AT}x[n] + A^{-1}\left(e^{AT} - I\right)Bu[n] \tag{3.43}$$

where each input is assumed to be constant in between the interval kT≤t<T. T is the length of time in [sec] between each discrete step. In Section 1.1, h is used rather than T to describe this because T is already used to describe the time between heart beats in the PD model. With the newly discretized system, an optimization problem can be formulated as shown below. This applies to any system with a linear dynamical or state-space equation regardless of output equation.

$$x[n+1] = A_d x[n] + B_d u[n]. \tag{3.44}$$

where $A_d = e^{AT}$ and $B_d = A^{-1}(e^{AT}-1)B$.

1.6.6 Derivation

The discretization formulation above can be fully derived with the zero-order hold assumption. First, in reference to the original differential equation, it is noted the equation includes multi-dimensional state and input vectors, x and u respectively, as follows, $$\dot{x}(t) = Ax(t) + Bu(t) \tag{3.45}$$

It is assumed that u takes on a singular value for a set time, $$u(t) = u(kT), \text{ for } kT \le t < (k+1)T \tag{3.46}$$

Next, the continuous time differential equation is solved using the integrating factor, μ(t), method. First, the integrating factor is found to be, $$\mu(t) = \exp\left\{\int -A dt\right\} \tag{3.47}$$

$$= \exp\{-At\} \tag{3.48}$$

Next, both sides of the differential equation in standard form are multiplied by the integrating factor, $$\exp\{-At\}(\dot{x}(t) - Ax(t)) = \exp\{-At\}Bu \tag{3.49}$$

Next, by the product rule of differentiation, the left hand side is converted to (μ(t)x(t)'), $$(\exp\{-At\}x)' = \exp\{-At\}Bu \tag{3.50}$$

Next, both sides are integrated from kT to kT+T, $$\int_{kT}^{kT+T} (\exp\{-At\}x)'d\tau = \int_{kT}^{kT+T} \exp\{-At\}Bud\tau \tag{3.51}$$

The left hand side can be simplified as follows, $$\exp\{-A(kT+T)\}x(kT+T) - \exp\{-A(kT)\}x(kT) = \tag{3.52}$$
$$\int_{kT}^{kT+T} \exp\{-At\}Bud\tau$$

The equation can then be rearranged as follows, $$\exp\{-A(kT + T)\}x(kT + T) =$$ (3.53)

$$\exp\{-A(kT)\}x(kT) + \int_{kT}^{kT+T} \exp\{-At\}Bud\tau$$

Both sides of Eq. 3.53 are then divided by the exponential on the left hand side, as follows, $$x(kT + T) = \exp\{-A(T)\}x(kT) + \exp\{A(kT + T)\}\int_{kT}^{kT+T} \exp\{-At\}Bud\tau$$ (3.54)

Since B and u are not time-varying, they serve as constants in the definite integral. So, integration is as follows, $$x(kT + T) =$$ (3.55)

$$\exp\{-A(T)\}x(kT) + \exp\{A(kT + T)\}\left(-A^{-1}\exp\{-At\}Bu\,|_{kT}^{kT+T}\right)$$

Upon evaluating the integral, and multiplying the exponential through the second term, the following is obtained, $$x(kT + T) = \exp\{-A(T)\}x(kT) - A^{-1}\exp\{0\}Bu + A^{-1}\exp\{AT\}Bu$$ (3.56)

Eq. 3.56 can be simplified further, as follows, $$x(kT + T) = \exp\{-A(T)\}x(kT) - A^{-1}(\exp\{AT\} + I)Bu$$ (3.57)

If kT=n and kT+T=n+1, then the following is obtained, $$x[n + 1] = \exp\{-A(T)\}x[n] + A^{-1}(\exp\{AT\} - I)Bu[n]$$ (3.58)

Each input is assumed to be constant in between the interval $kT \le t < T$. Thus, $$x[n + 1] = A_d x[n] + B_d u[n].$$ (3.59)

where $A_d = e^{AT}$ and $B_d = A^{-1}(e^{AT} - 1)B$.

1.6.7 Changing the Cost Function

This section discloses additional details on the formulation of the cost function in Section 1.1. If a traditional quadratic cost formulation is built and evaluated, the particular weights that lead to penalizing certain terms can be identified. This can be used to penalize the states.

$$x^T Q x = \begin{bmatrix} c_1^{PE} & c_2^{PE} & c_1^{NI} & c_2^{NI} \end{bmatrix} \begin{bmatrix} Q_{11} & Q_{12} & Q_{13} & Q_{14} \\ Q_{21} & Q_{22} & Q_{23} & Q_{24} \\ Q_{31} & Q_{32} & Q_{33} & Q_{34} \\ Q_{41} & Q_{42} & Q_{43} & Q_{44} \end{bmatrix} \begin{bmatrix} c_1^{PE} \\ c_2^{PE} \\ c_1^{NI} \\ c_2^{NI} \end{bmatrix}$$ (3.60)

$$= Q_{11}c_1^{PE2} + Q_{21}c_2^{PE}c_1^{PE} + Q_{31}c_1^{NI}c_1^{PE} + Q_{41}c_2^{NI}c_1^{PE} +$$ (3.61)

$$Q_{12}c_1^{PE}c_2^{PE} + Q_{22}c_2^{PE2} + Q_{32}c_1^{NI}c_2^{PE} + Q_{42}c_2^{NI}c_2^{PE} +$$ (3.62)

-continued $$Q_{13}c_1^{PE}c_1^{NI} + Q_{23}c_2^{PE}c_1^{NI} + Q_{33}c_1^{NI2} + Q_{43}c_2^{NI}c_1^{NI} +$$ (3.63)

$$Q_{14}c_1^{PE}c_2^{NI} + Q_{24}c_2^{PE}c_2^{NI} + Q_{34}c_1^{NI}c_2^{NI} + Q_{44}c_2^{NI2}$$ (3.64)

The explicit notation of these terms provides a better understanding of the meaning behind adding weights to certain indices of the Q matrix. A similar approach can be applied to the inputs as well, as follows, $$u^T R u = \begin{bmatrix} u^{PE} & u^{NI} \end{bmatrix} \begin{bmatrix} R_{11} & R_{12} \\ R_{21} & R_{22} \end{bmatrix} \begin{bmatrix} u^{PE} \\ u^{NI} \end{bmatrix}$$ (3.65)

$$= \begin{bmatrix} R_{11}u^{PE} + R_{21}u^{NI} & R_{12}u^{PE} + R_{22}u^{NI} \end{bmatrix} \begin{bmatrix} u^{PE} \\ u^{NI} \end{bmatrix}$$ (3.66)

$$= R_{11}u^{PE2} + R_{21}u^{NI}u^{PE} + R_{12}u^{PE}u^{NI} + R_{22}u^{NI2}$$ (3.67)

When choosing the cost function, it is preferable to make a principled choice on what the algorithm penalizes. Traditionally, I is chosen for the Q and R matrices. However, in this context, it may be preferable to penalize combinations of drug inputs as well. Penalizing combinations of drug inputs will deter the system from inputting both drugs at once, for instance.

2. Example 2—State Space Estimation of Hemodynamic Parameters In Vivo with the Two-Element Windkessel Model This example is directed generally to a method for estimating the physiological parameters of the two-element Windkessel model from a peripheral blood pressure waveform since peripheral arterial lines are standard in operating rooms. Specifically, the method seeks to combine the benefits of long timescale estimation with that of beat-to-beat estimation with an estimation approach novel to this application. This can be accomplished by building a Kalman filter to estimate the time constant parameter, $\tau$ of the two-compartment Windkessel model. Then, the time constant and either the blood pressure waveform or a measurement of cardiac output can be used to infer three other parameters of the Windkessel model: 1) the stroke volume, $\Delta V$, 2) the systemic vascular resistance, R, and 3) the arterial compliance, C. Unlike conventional methods, the method disclosed in this section implements a Kalman filter for estimation of a two-element Windkessel model parameter from observations from a single peripheral arterial line.

2.1 Methods

In this section, the methods used to move from a raw blood pressure waveform to an estimate of a patient's cardiovascular state as defined by parameters of the Windkessel model is presented. For reference, $R_a = R$, and $C_a = C$.

2.1.1 Low Pass Filter

First, a low pass filter is designed for the blood pressure waveform. A finite impulse response (FIR) filter is chosen, which is symmetric. FIR filters with symmetry have linear phase and a resultant constant group delay meaning each frequency component is delayed in time by the same number of samples. By keeping track of the group delay, a signal can be filtered in real time, waveform features of the filtered signal can be detected, and the delay induced by the filter can be accounted for. Thus, detected features of the filtered waveform can be appropriately attributed to the raw signal.

As an example, the kaiser window is chosen. The parameters for this filter are the following: 1) discrete-time cutoff frequency: $\omega_c=(\Omega_c 2\pi)/\Omega_s$; 2) equivalent continuous-time cutoff frequency: $\Omega_c=18$ [Hz]; 3) discrete-time passband edge: $\omega_{pass}=(2\pi\Omega_{pass})/\Omega_s$; 4) discrete-time stopband edge: $\omega_{stop}=(2\pi\Omega_{stop})/\Omega_s$; 5) equivalent continuous-time passband edge: $\Omega_{pass}=16$ [Hz]; and 6) equivalent continuous-time stopband edge: $\Omega_{stop}=20$ [Hz].

2.1.2 Kalman Filter

A Kalman filter is used to estimate $\tau$, the time constant parameter in the two-element Windkessel model, from a peripheral arterial blood pressure waveform. For reference, Section 1.6 discloses the derivation of the Windkessel model differential equation, and of the homogenous solution to the Windkessel model, which explicitly defines the time-constant, $\tau$.

As described above, FIG. 3 is the circuit representation of the two-element Windkessel model. This is a representation, which describes one cardiovascular state of a patient for a given set of initial conditions and parameters $R_a$ and $C_a$. The derivation of a state space Kalman filter includes describing a state equation and an observation equation. These are defined in the following sections.

Observation Equation

This section presents the derivation of the observation equation. From the two-element Windkessel, the diastolic decay of the blood pressure waveform can be described in terms of the time constant $\tau[k]$ where, $$\tau[k] = R_a[k]C_a \qquad (4.1)$$

It is assumed that $C_a$ is not time-varying. It is further assumed that $R_a$ is time-varying between beats, but is stationary within a beat; hence, $R_a$ is indexed with k. Assuming there is no noise in the system, the observation equation becomes, $$y_i[k] = A[k]e^{-\frac{t_i[k]}{\tau[k]}} \qquad (4.2)$$

where $k\in\{0,1,\ldots,K-1\}$ indexes the K heart beats, $i\in\{0,1,\ldots,I[k]-1\}$ indexes the I[k] time points per beat. The number of observations per time point can vary for each beat; hence, I is also indexed by k.

For simplicity, Eq. 4.2 is log-transformed, as follows, $$\log(y_i[k]) = \log\left(A[k]e^{-\frac{t_i[k]}{\tau[k]}}\right) \qquad (4.3)$$

$$= \log(A[k]) + \log\left(e^{-\frac{t_i[k]}{\tau[k]}}\right) \qquad (4.4)$$

$$= \log(A[k]) - \frac{t_i[k]}{\tau[k]} \qquad (4.5)$$

$$= \log(A[k]) - \frac{1}{\tau[k]}t_i[k] \qquad (4.6)$$

$$= \alpha[k] = \beta[k]t_i[k] \qquad (4.7)$$

Now, with this transformed relationship, and setting log $(y_i[k])=\upsilon_i[k]$, the assumption of additive noise is made, $$\upsilon_i[k] = \beta[k]t_i[k] + \alpha[k] + \epsilon_i[k] \qquad (4.8)$$

This relationship states that the observations, $\upsilon_i[k]=\log$ $(y_i[k])$, are linearly related to $t_i[k]$ with slope, $\beta_k=-1/\tau[k]$ and intercept, $\alpha[k]=\log(A[k])$ with additive noise $\epsilon_i[k]$. Each $\epsilon_i[k]$ is independent. It is assumed $$\epsilon_i[k] \sim N(0, \sigma_\epsilon^2).$$

The observation equation can be expanded to be multidimensional, as follows, $$\begin{bmatrix} \upsilon_0[k] \\ \upsilon_1[k] \\ \vdots \\ \upsilon_{(I[k]-1)}[k] \end{bmatrix} = \begin{bmatrix} t_0[k] & 1 \\ t_1[k] & 1 \\ \vdots & \vdots \\ t_{(I[k]-1)}[k] & 1 \end{bmatrix} \begin{bmatrix} \beta[k] \\ \alpha[k] \end{bmatrix} + \begin{bmatrix} \epsilon_0[k] \\ \epsilon_1[k] \\ \vdots \\ \epsilon_{(I[k]-1)}[k] \end{bmatrix} \qquad (4.9)$$

The following definitions are further made, where bold variables represent matrices:

$$\upsilon[k] := [\upsilon_0[k] \quad \upsilon_1[k] \quad \ldots \quad \upsilon_{(I[k]-1)}[k]] \qquad (4.10)$$

$$\theta[k] := \begin{bmatrix} t_0[k] & t_1[k] & \ldots & t_{(I[k]-1)}[k] \\ 1 & 1 & \ldots & 1 \end{bmatrix}^T \qquad (4.11)$$

$$x[k] := [\beta[k] \quad \alpha[k]]^T \qquad (4.12)$$

$$\epsilon[k] := [\epsilon_0[k] \quad \epsilon_1[k] \quad \ldots \quad \epsilon_{(I[k]-1)}[k]]^T \qquad (4.13)$$

Eq. 4.9 can be represented in a more compact notation, which is the final observation equation:

$$\upsilon[k] = \theta[k]x[k] + \epsilon[k] \qquad (4.14)$$

where column vectors $\upsilon[k]\in \mathbb{R}^I$, $x[k]\in \mathbb{R}^I$, $\epsilon[k]\in \mathbb{R}^I$, and $\theta[k]\in \mathbb{R}^{I\times2}$.

$$y[k] = C[k]x[k] + \epsilon[k] \qquad (4.15)$$

State Space Equation

This section presents the derivation of the state space equation. For the state vector x[k], it is assumed that it follows a Gaussian random walk, as follows, $$x[k+1] = x[k] + \eta[k] \qquad (4.16)$$

where $\eta[k] \sim N(0, \Sigma_\eta)$ and, $$\Sigma_\eta[k] = \begin{bmatrix} \sigma_{\eta_1}^2 & 0 \\ 0 & \sigma_{\eta_2}^2 \end{bmatrix} \qquad (4.17)$$

and each $\eta[k]$ is independent. With this, the state space equation is specified.

Kalman Filter Equations

Given the MAP estimate of x[k−1] at time step [k−1], $x_{[k-1|k-1]}$, and he defined observation and state equations above have Gaussian additive noise, the state estimation framework can be fully specified using the traditional Kalman filter equations.

One-Step Prediction Density $$x_{[k|k-1]} = x_{[k-1|k-1]} \tag{4.18}$$

$$\sum\nolimits_{[k|k-1]} = \sum\nolimits_{[k-1|k-1]} + \sum\nolimits_{\eta} \tag{4.19}$$

Kalman Gain $$K[k] = \sum\nolimits_{[k|k-1]} \theta[k]^T \left( \theta[k] \sum\nolimits_{[k|k-1]} \theta[k]^T + \sum\nolimits_{\epsilon}[k] \right)^{-1} \tag{4.20}$$

where, given $I_{I[k] \times I[k]}$ is an identity matrix of dimension I[k]×I[k], $$\sum\nolimits_{\epsilon}[k] = \sigma_{\epsilon}^2 I_{I[k] \times I[k]} \tag{4.21}$$

Posterior Density $$x_{[k|k]} = x_{[k|k-1]} + K[k](v[k] - \theta[k]x_{[k|k-1]}) \tag{4.22}$$

$$\sum\nolimits_{[k|k]} = (I_{2\times2} - K[k]\theta[k]) \sum\nolimits_{k|k-1} (I_{2\times2} - K[k]\theta[k])^T + K[k] \sum\nolimits_{\epsilon}[k]) K[k]^T \tag{4.23}$$

Prior Density

In order to run the Kalman filter, an assumption is made of the initial state at k=0. This can be accomplished by doing a standard linear regression to estimate the slope and intercept contained in the state vector, as follows, $$v[0] = \theta[0]x[0] + \epsilon[0] \tag{4.24}$$

$$x_{[0|0]} = (\theta[0]^T \theta[0])^{-1} \theta[0]^T v[0] \tag{4.25}$$

$$\Sigma_{[0|0]} = (\theta[0]^T \theta[0])^{-1} \hat{\sigma}_{\epsilon}^2 \tag{4.26}$$

$$\hat{\sigma}_{\epsilon}^2 = \frac{(v[0] - \theta[0]x_{[0|0]})^T (v[0] - \theta[0]x_{[0|0]})}{1} \tag{4.27}$$

Following implementation of the Kalman filter, MAP estimates of x and Σ for each time point are obtained. The estimates of x can be transformed back into variables with physiological interpretation, $$x[k] = \begin{bmatrix} \beta[k] \\ \alpha[k] \end{bmatrix} = \begin{bmatrix} -\dfrac{1}{\tau[k]} \\ \log(A[k]) \end{bmatrix} \tag{4.28}$$

In order to take the MAP estimates, and transform them back into A[k] and τ[k], the following is done, $$\hat{A}[k] = e^{\alpha[k]} = e^{x[k,1]} \tag{4.29}$$

-continued $$\hat{\tau}[k] = -\frac{1}{\beta[k]} = -\frac{1}{x[k, 0]} \tag{4.30}$$

Once the Kalman filter estimates are transformed back to [k] and τ[k], the cardiac output is estimated, as follows, $$CO[k] \propto \frac{\dfrac{1}{N} \sum_{k=0}^{I[k]} y_i[k]}{\tau[k]} \tag{4.31}$$

The cardiac output, CO, is estimated at time k to be proportional to the mean arterial blood pressure of beat k. Once this proportional value is found, the estimated proportional CO estimates are scaled to have the same mean value. The estimated CO values were scaled to match the actual CO values.

2.2 Solving for ΔV, $R_a$, and $C_a$

From this framework, an estimate of τ can be obtained. Estimates of $R_a$ and $C_a$ can then be derived individually, assuming a measurement of CO, or ΔV over a single beat is available. The following assumptions are made: 1) peripheral circulation can be approximated by the Windkessel model, 2) the volume injection from the heart into peripheral circulation is an impulse train, 3) $C_a$ is unchanging (since it is assumed in the framework that the system remains in a normal physiological range).

An estimate for $\tau_i$ is derived at every ith beat from the state space model above. Based on the above assumptions made of the system, three equations can be obtained, as follows, $$P_a = \frac{\Delta V}{T} R_a \tag{4.32}$$

$$\tau = R_a C_a \tag{4.33}$$

$$C_a = \frac{\Delta V}{\Delta P} \tag{4.34}$$

Eq. 4.32 is Ohm's law. Eq. 4.33 describes the time-constant of the exponential decay of the model in terms of $R_a$ and $C_a$. Eq. 4.34 comes from the definition of capacitance or compliance.

Eqs. 4.32-4.34 provides a set of equations, and, assuming a measurement of CO is obtained, there are two unknowns: 1) $R_a$, and 2) $C_a$. Thus, with observations of T, and estimates of τ for each ith beat, each of the unknowns can be solved at each ith beat.

2.3 Results and Discussion

Figure 6:
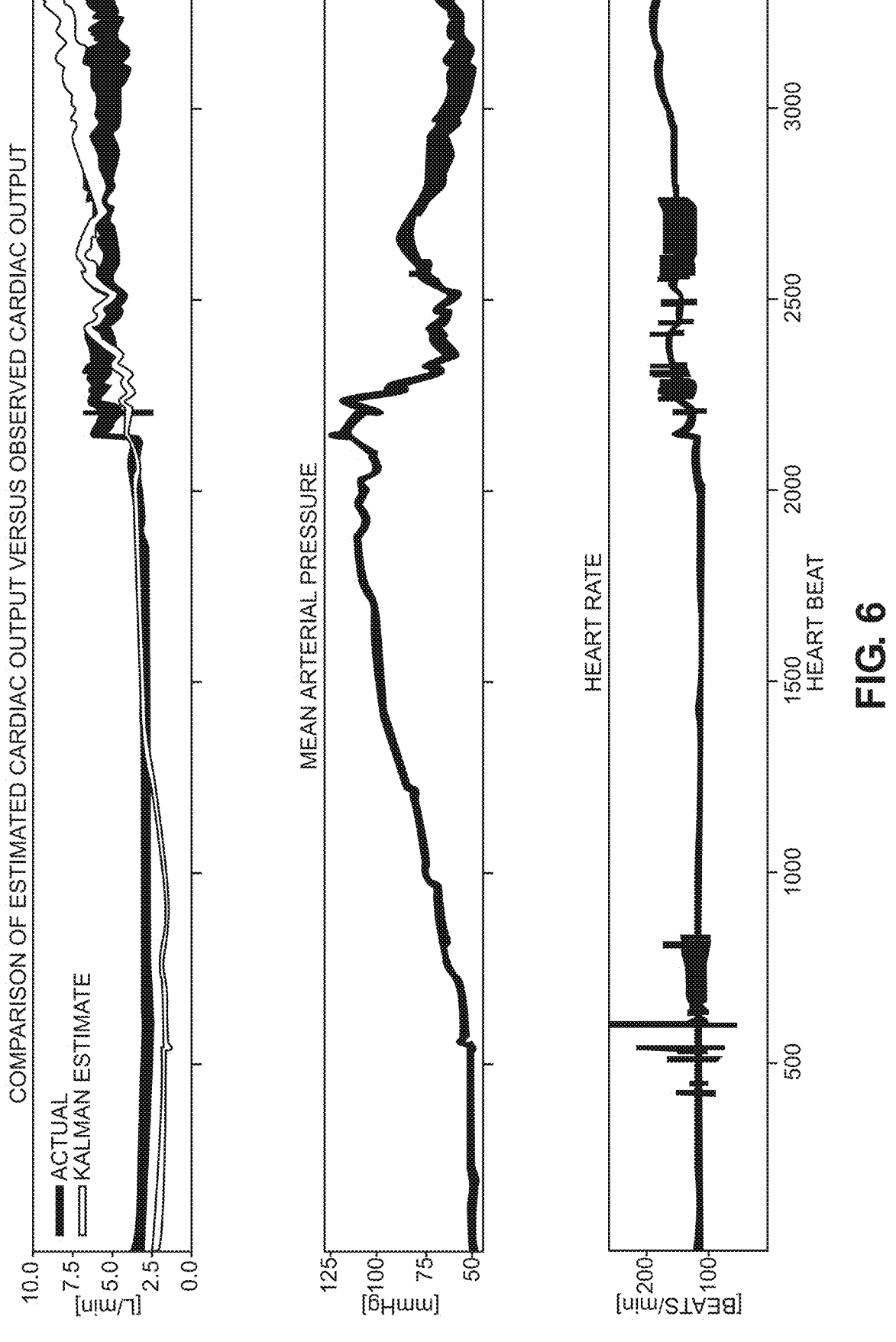

A preliminary validation of the model described in the preceding sections is performed using previously collected swine data from previous work. The results on the data are shown in FIG. 6 corresponding to Yorkshire swine. As shown, the results show the feasibility of using this framework to estimate a cardiovascular state of a patient, with a mean absolute percent error of about 24%. Future work warrants comparison of this method with state of the art methods for estimation of cardiovascular state as defined by parameters of the Windkessel model.

3. Example 3

This example is generally directed to a refined closed-loop system for blood pressure control (CLBPC). The CLBPC disclosed herein addresses, at least in part, the wide variability in response of patients to vasoactive drugs, which has led to difficulties in achieving robust performance in conventional CLBPC's. Specifically, the CLBPC emphasizes incorporation of mechanistic cardiovascular models. The robustness of this system is further assessed with respect to the mismatch in internal model parameters that are expected to vary widely within a patient population. An updated pharmacokinetic-pharmacodynamic (PK-PD) model relating drugs, phenylephrine and nicardipine, to impacts on the blood pressure waveform is provided; a state space model is then formulated which incorporates the full dynamics of the blood pressure waveform. Model predictive control (MPC) is then implemented with this state space model to simulate regulation of blood pressure, and explore the robustness of this framework to model parameter mismatch. It is shown that parameter mismatch does impact performance of the CLBPC in regulation of a simulated patient waveform to a target blood pressure waveform, and the parameters that are pivotal to estimate in clinical scenarios are further elucidated. This performance impact is greatly lessened when the infusion rates can be updated more rapidly. For example, a control simulation with 15 [sec] drug infusion rate updates led to an overshoot of 65 [mmHg], ~60 [mmHg] more than the same simulation with 2 [sec] drug infusion rate updates. The robustness testing provides support for estimation of PK and PD parameters in CLBPC systems, and emphasizes the importance of improving programmable infusion pumps to allow for rapid updates of infusion rates.

3.1 Introduction

Management of blood pressure in the operating room is important for post-operative outcomes; as such, closed-loop systems for blood pressure control are desirable. Development of robust CLBPCs is challenging because of 1) wide variability of vasoactive drug sensitivity in patient populations, and 2) limits on the frequency with which drug infusion rates can be updated while retaining flow accuracy.

Previous work on development of CLBPCs explored robustness of designed controllers, and have designed controllers with robustness in mind. These previous works took valid steps to address robust control, but did not incorporate current knowledge and models of the physiology governing blood pressure dynamics. Additionally, no study has explored the impact of the restriction of update frequency of infusion rates on robustness of control to model mismatch, to the author's knowledge. Because high infusion rate updates for state of the art programmable infusion pumps lead to poor flow accuracy, pumps must update infusion rates at 15-30 [sec] intervals. As such, clinical applicability of systems depend on the impact on control performance of this rate update restriction.

In Section 1, a pharmacokinetic-pharmacodynamic (PK-PD) model describing how blood pressure responds to vasoactive drugs is discussed, emphasizing the incorporation of the two-element Windkessel model, a mechanistic model of the cardiovascular system. In Section 1, a standard model predictive control (MPC) framework is also presented incorporating this system model.

In Section 3, this framework is extended in several ways. First, the dynamic model of the blood pressure waveform is incorporated into the MPC framework. Second, the assumption that the flow waveform of blood volume into the peripheral circulation is an impulse train is relaxed. This improved framework is then used to explore robustness of the system model to parameter mismatch, and the dependence of this robustness on the frequency with which drug infusion rates can be updated.

3.2 Model

In this section, a framework is presented, which relates drug inputs to effects on the cardiovascular system with a goal of controlling blood pressure dynamics. In this framework, the two-element Windkessel model is used as the foundation of the model of the cardiovascular system. Traditional pharmacokinetic modeling is used to describe the dynamics of drugs moving throughout the body. A simple relationship between drug concentrations and impact on the cardiovascular system is used to link these two components.

3.2.1 Pharmacokinetic Model

First, drug infusions are related to resultant concentrations throughout the body with chosen drugs, phenylephrine (PE) and nicardipine (NI). PE is a pure $\alpha 1$ adrenergic agonist of the sympathetic system. Because of this, PE induces peripheral arterial vasoconstriction and ultimately an increase in systemic vascular resistance, $R_a$. NI is a dihydropyridine calcium channel antagonist. Because of this, NI induces coronary and cerebral vasodilation and, ultimately, a decrease in $R_a$. PE provides positive control action (increases blood pressure), and NI provides positive control action (decreases blood pressure).

PE and NI movement through the body are modeled as traditional compartmental PK models, where drugs injected into the body move between a first tissue compartment, with near instantaneous drug distribution, and a second tissue compartment, with slower drug distribution. The PK model is as follows, $$d[n+1] = Ad[n] + Bv[n] \tag{5.1}$$

where n is a discrete time index. Also, $$d[n] = \left[ d_1^{PE}[n], d_2^{PE}[n], d_1^{NI}[n], d_2^{NI}[n] \right]^T,$$

where $$d_1^{drug}$$

in $[\mu g \cdot L^{-1}]$ represents the first compartmental concentration of a drug, and $$d_2^{drug}$$

in $[\mu g \cdot L^{-1}]$ represents the second compartmental concentration of a drug. Further, $v[n] = [v^{PE}[n], v^{NI}[n]]^T$, where $v^{drug}[n]$ in $[\mu g \cdot min^{-1}]$ represents the input of that drug into its respective first compartment. A is defined to be, $$A = \begin{bmatrix} A^{PE} & 0 \\ 0 & A^{NI} \end{bmatrix} \tag{5.2}$$

where 0 is defined as a matrix of zeros (of appropriate size) and $A^{drug}$ is a unitless matrix of rate constants that describe the movement of that drug through the two compartments. B is defined to be, $$B = \begin{bmatrix} B^{PE} & 0 \\ 0 & B^{NI} \end{bmatrix} \tag{5.3}$$

where $B^{drug}$ in $[\text{min}\cdot\text{L}^{-1}]$ provides unit conversion constants from $[\mu g \cdot \text{min}^{-1}]$ to $[\mu g \cdot \text{L}^{-1}]$. Additionally, A and B are block-diagonal to reflect the assumption of non-interaction of PE and NI drug pharmacokinetics.

3.2.2 Pharmacodynamic Model

Next, a mechanistic cardiovascular model is defined, which is used to relate drug infusions to impact on the blood pressure waveform. This begins with the Windkessel model, which is a simple biophysical model of blood pressure dynamics in the aorta, the main artery of the body. The Windkessel model represents these dynamics through the interplay of a compliant system of major vessels and a terminal vascular resistance from the microcirculation (arterioles, capillaries, and venules) while considering the venous system's resistive contributions as negligible. The original two-element Windkessel Model is used, as shown in FIG. 3.

From this circuit model, the differential equation in Eq. 5.4 can be derived, $$\dot{p}(t) + \frac{1}{R_a C_a}p(t) = \frac{f(t)}{C_a} \tag{5.4}$$

where $f(t)$ in $[\text{mL}\cdot\text{sec}^{-1}]$ represents the volumetric inflow into the blood vessels from the heart, $p(t)$ in $[\text{mmHg}]$ represents the blood pressure in the aorta, $C_a$ in $[\text{mL}\cdot\text{mmHg}^{-1}]$ is the compliance of the body's major vessels, and $R_a$ in $[\text{mmHg}\cdot\text{sec}\cdot\text{mL}^{-1}]$ is the systemic vascular resistance to blood flow from the arterial microcirculation. The solution of this equation is a model of the blood pressure waveform.

From the Windkessel model, an approximate difference equation can be derived, as follows, $$p[n+1] = p[n] + \frac{T_s}{C_a}f[n] - \frac{T_s}{\tau[n]}p[n] \tag{5.5}$$

where $p[n]$ is a discrete blood pressure waveform in $[\text{mmHg}]$, $$T_s = f_s^{-1} \tag{}$$

in $[\text{sec}]$ is the time between samples of the discrete waveform, and $\tau[n]=R_a[n]C_a$ in $[\text{sec}]$ is the time-constant of the two-element Windkessel model with the additional assumption that $R_a$ varies over time. It is assumed that $f[n]$, the flow of blood volume into the peripheral circulation in $[\text{mL}\cdot\text{sec}^{-1}]$, takes on a pulse train form, as follows, $$f[n] = \begin{cases} \dfrac{\Delta V}{T_f}, & n \in \{kf_sT_p, kf_sT_p + f_sT_f\} \quad \text{(systole)} \\ 0, & n \in \{kf_sT_p + f_sT_f, (k+1)f_sT_p\} \quad \text{(diastole)} \end{cases} \tag{5.6}$$

where $\Delta V$ is the stroke volume in $[\text{ml}]$, $T_p$ describes the duration of the blood pressure pulse in $[\text{sec}]$, $T_f$ describes the duration of the flow pulse in $[\text{sec}]$, and $k$ indexes heart beats.

3.2.3 Pharmacokinetic-Pharmacodynamic Link

Finally, a simple relationship between $d[n]$ and $\tau[n]=Ra[n]Ca$ can be defined, as follows, $$\tau[n] = [E^{PE} \quad 0 \quad E^{NI} \quad 0]d[n] + \tau_{base} \tag{5.7}$$

where $E^{drug}$ in $[\text{sec}\cdot\text{L}\cdot\mu g^{-1}]$ converts change in drug concentration to impact on the time constant from the two-element Windkessel Model, and $\tau_{base}$ is the baseline $\tau$ of the patient prior to initiating control. This equation simply states that an increase in drug impacts the time constant of the two-element Windkessel model linearly through modulation of $R_a$. As described in Section 3.2.1, PE increases $R_a$, so $E^{PE}>0$, and NI decreases $R_a$, so $E^{NI}<0$.

3.3 Model Predictive Control Formulation

Next, a model predictive control (MPC) framework is formulated. To implement this framework, first, a state space model is assembled from the specified mechanistic physiological model, and then an MPC controller is built around this state space model.

3.3.1 State Space Formulation

A state space model of the system is first assembled with states including the drug concentrations throughout the body, blood pressure, and the time constant of the two-element Windkessel model, $$x[n] = [d[n] \quad d[n-1] \quad p[n-1] \quad \tau[n-1]]^T \tag{5.8}$$

Next the state space input vector is defined as input drug infusions into the patient, $$u[n] = [v[n] \quad v[n-1]]^T \tag{5.9}$$

This particular formulation provides a valid state space dynamic equation, which combines the PK, PD and PK-PD linking models. The state space dynamic equations are defined as follows, $$\begin{bmatrix} d[n+1] \\ d[n] \\ p[n] \\ \tau[n] \end{bmatrix} = \begin{bmatrix} Ad[n] + Bv[n] \\ Ad[n-1] + Bv[n-1] \\ p[n-1] + \dfrac{T_s}{C_a}f[n-1] - \dfrac{T_s}{\tau[n]}p[n-1] \\ Ed[n] + \tau_{base} \end{bmatrix} \tag{5.10}$$

where $f[n]$ is defined in Eq. 5.6. This model includes the parameters: $\theta=\{A,B,E,C_a,\Delta V,T_f,T_p\}$.

3.3.2 Model Predictive Control Algorithm

An MPC framework around this state space model is formulated, written in pseudocode in Algorithm 2 below. At each time where the drug infusion rates can be updated, the following occurs: 1) observe the current blood pressure waveform segment, 2) estimate current states from the patient, 3) specify a target blood pressure waveform given current state, 4) choose a trajectory of PE and NI infusion rates with the trajectory optimization specified in Eq. 5.11, 5) infuse the initial set of drug into the patient, and 6) repeat steps 1)-5).

---

```
Algorithm 2 Control of Blood Pressure with MPC
```

```
Observe p_base from patient
Estimate x[0], τ_base
Initialize n = 0, i = 0
Choose N, M, numSteps
while i < numSteps do
  Choose p_target
  Trajectory optimization to get u*, Eq.(11)
  u(iM, iM + 1, . . . , (i + 1)M − 1] ← u*[0]
  Apply u*[0] to patient for M samples
  Observe p_patient[iM : (i + 1)M]
  Estimate x[iM]
end while
```

---

In Algorithm 2, $p_{base}$ in [mmHg] refers to the blood pressure waveform that can be observed before control begins, x[0] is the initial state vector, $\tau_{base}$ is the baseline estimate of $\tau$ in [sec], n indexes the samples of the patient blood pressure waveform, i indexes the iterations of MPC, N in [samples] is the horizon of the trajectory optimization, M specifies the time required to pass before a new switch of the infusion rates is possible, numSteps specifies how many iterations of MPC that will run, $p_{target}$ in [mmHg] is an N samples long blood pressure waveform simulated from the two-element Windkessel model, u* is the set of drug infusion rates resulting from the trajectory optimization in Eq. 5.11, and u*[0] is the first set of drug infusion rates. The trajectory optimization is defined as follows, $$u^* = \operatorname*{argmin}_{u[\cdot]} \sum_{m=0}^{N} \frac{u[m]^T Q u[m]}{2} + \frac{(p_{internal}[m] - p_{target}[m])^2}{2} \quad (5.11)$$

sub. to $x[m + 1] := $ Eq. 10 with $\theta = \theta_{internal}$ $\forall$ m $u[m] \le u_{max} \forall$ m $u[m] \ge 0$ $\forall$ m $\tau[m] > 0$ $\forall$ m $p[m] > 0$ $\forall$ m $u = u[m + 1] \forall$ m $\in \{hM - 1\}$ $e_2 u[m + 1] = e_1 u[m]$ $\forall$ m $e_2 x[m + 1] = e_1 x[m]$ $\forall$ m where m is the time index for the current trajectory optimization, $Q=Q^T \ge 0$ specifies the weights of cost on the input drug infusion rates, $u_{max}$ in [μg·min$^{-1}$] are the bounds of safe drug infusion rates allowed, h is the set of non-negative integers, $e_k$ is the vector all of whose entries are zero except the k-th entry which is unity.

In the trajectory optimization described in Eq. 5.11, the u that minimizes the cost function, u*, is picked. In the cost function, the input infusion rates, and the error between $p_{target}$ and $p_{internal}$ are penalized. The trajectory optimization is constrained to follow the discrete time dynamics defined in Eq. 5.10, limiting the values u, p, and $\tau$ to physiologically plausible and clinically safe ranges. Additionally, a switching constraint is enforced limiting the frequency at which the input drug infusion rates can be updated (every M samples) to include the current limitations of state of the art programmable infusion pumps.

3.4 Simulation Experiment Design

Simulation experiments are designed to assess robustness of the control framework to model mismatch and, and its dependence on the switching constraint. The experiments focus on the clinically relevant context of regulating the blood pressure waveform of a patient in hypotension back to a normal operating range with a mean pressure around 100 [mmHg]. In these simulations, no state estimation was performed. Instead, states from the patient model were directly observed.

For a single simulation, a patient model—Eq. 5.10 with parameter set $\theta_{patient}$—is defined and an internal model—Eq. 5.10 with parameter set θinternal is used for control. The patient models were initialized such that $p_{base}$ was oscillating between 60 [mmHg] systolic and 40 [mmHg] diastolic. $\theta_{internal}$ is defined to be mean estimates of the corresponding parameters from previous experimental studies, or values which produced expected physiological responses if no experimental study was present. Then, $\theta_{patient}$ is chosen to be equivalent to $\theta_{internal}$, with the exception of a single parameter which was adjusted to some percentage ranging from 50%-150% of its mean value. Within every control run, equivalent values were maintained for the following: the sampling rate of each discrete signal, $f_s$=10 [Hz], the horizon of each trajectory optimization, N=50 [sec]; the total duration of each control run, M·numSteps=120 [sec]; the bounds of the drug infusion rates, $u_{max}$=[100, 85, 100, 85]T [μg·min$^{-1}$]; the weighted cost of the drug infusion rates, Q=I with $Q_{2,3}=Q_{3,2}$=1000 to ensure that only one drug is being infused at a time; the baseline patient blood pressure waveform, $p_{base}$ as 200 [sec] of a simulated two-element Windkessel model with $\theta=\theta_{patient}$ and $\tau_{base}$=1 [sec].

Model mismatch was explored with $A^{PE}$, $B^{PE}$, and $E^{PE}$. $A^{PE}$ is a matrix of rate parameters, so, all rate parameters which compose the matrix are modulated the same amount between 50-150% of the mean value. This subset of 0 are difficult to experimentally observe, and are most likely to vary between patients. Additionally, parameters of PE are emphasized since the simulated patient is initially hypotensive.

Multiple control runs were performed with model mismatch for $A^{PE}$, $B^{PE}$, and $E^{PE}$, and generated control performance metrics for each run. These runs were performed with M=15 [sec], and then the same pipeline was run with M=2 [sec]. Results can be found in Section 3.5.

3.4.1 Control Performance Metrics

The following metrics are chosen when assessing control performance for each control run. First, MAE in [mmHg] is calculated from the patient's blood pressure waveform to the desired blood pressure waveform, $$MAE = \frac{\sum |p_{patient}[n] - p_{target}[n]|}{M \cdot numSteps} \quad (5.12)$$

where $p_{patient}$ is the controlled patient waveform in [mmHg]. Second, the overshoot, O in [mmHg] is calculated. O is defined as, $$O = \max(p_{patient}[n] - p_{target}) \quad (5.13)$$

Finally, the settling time, $t_{s,b}$ in [sec], is calculated, which is defined as the time after which every $|p_{patient}[n]=p_{target}[n]|<\pm$b [mmHg]. This is a clinically relevant definition of settling time.

3.5 Results

Figures 7A, 7B:
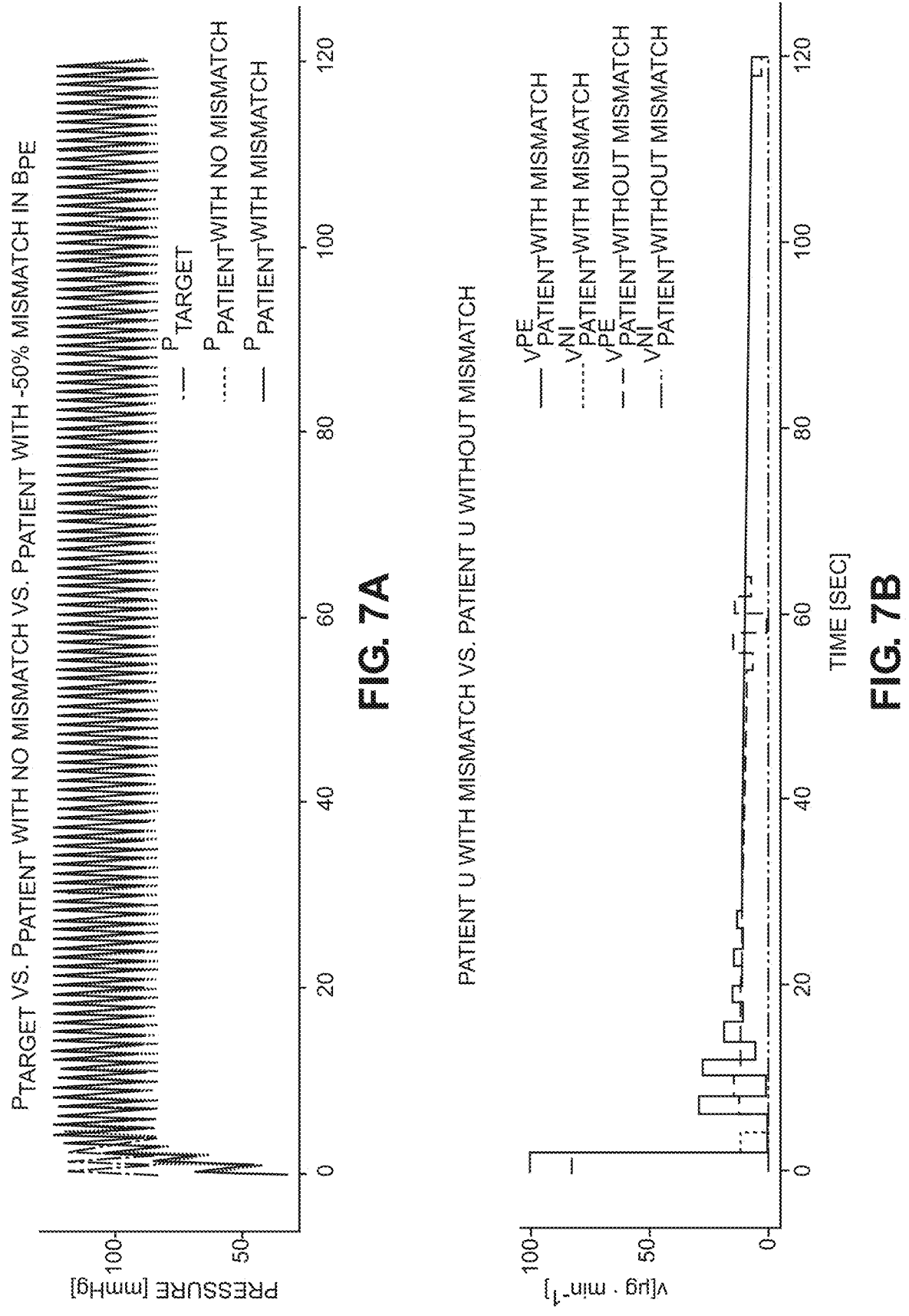
FIG. 7A shows the $p_{target}$, the resultant $p_{patient}$ from running control with mismatch, and the resultant $p_{patient}$ from running control without mismatch corresponding to a control simulation of blood pressure with model mismatch and fast updates. Specifically, $B^{PE}$ in $\theta_{patient}$ was modulated to be −50% of its mean value, and M was 2 [sec].
FIG. 7B shows the chosen drug infusion rates from MPC used to generate $p_{patient}$ with mismatch, and the chosen drug infusion rates from MPC used to generate $p_{patient}$ without mismatch for the simulation of FIG. 7A.

Two illustrative simulations of control with the described framework are first presented in FIGS. 7A-8B. In FIGS. 7A and 7B, the drug infusion rates could be updated every 2 [sec], a rate which currently leads to poor flow accuracy with state of the art programmable infusion pumps. In this case, control performance is mildly impacted, e.g., overshoot is clinically acceptable, avoiding hypertension, at $O \approx 6.4$ [mmHg], patient blood pressure reaches within 10 [mmHg] of the target rapidly after $t_{s,10} \approx 2.5$ [sec], and MAE to the target waveform is nearly equivalent to that when there is no mismatch with MAE≈4.4 [mmHg].

Figures 8A, 8B:
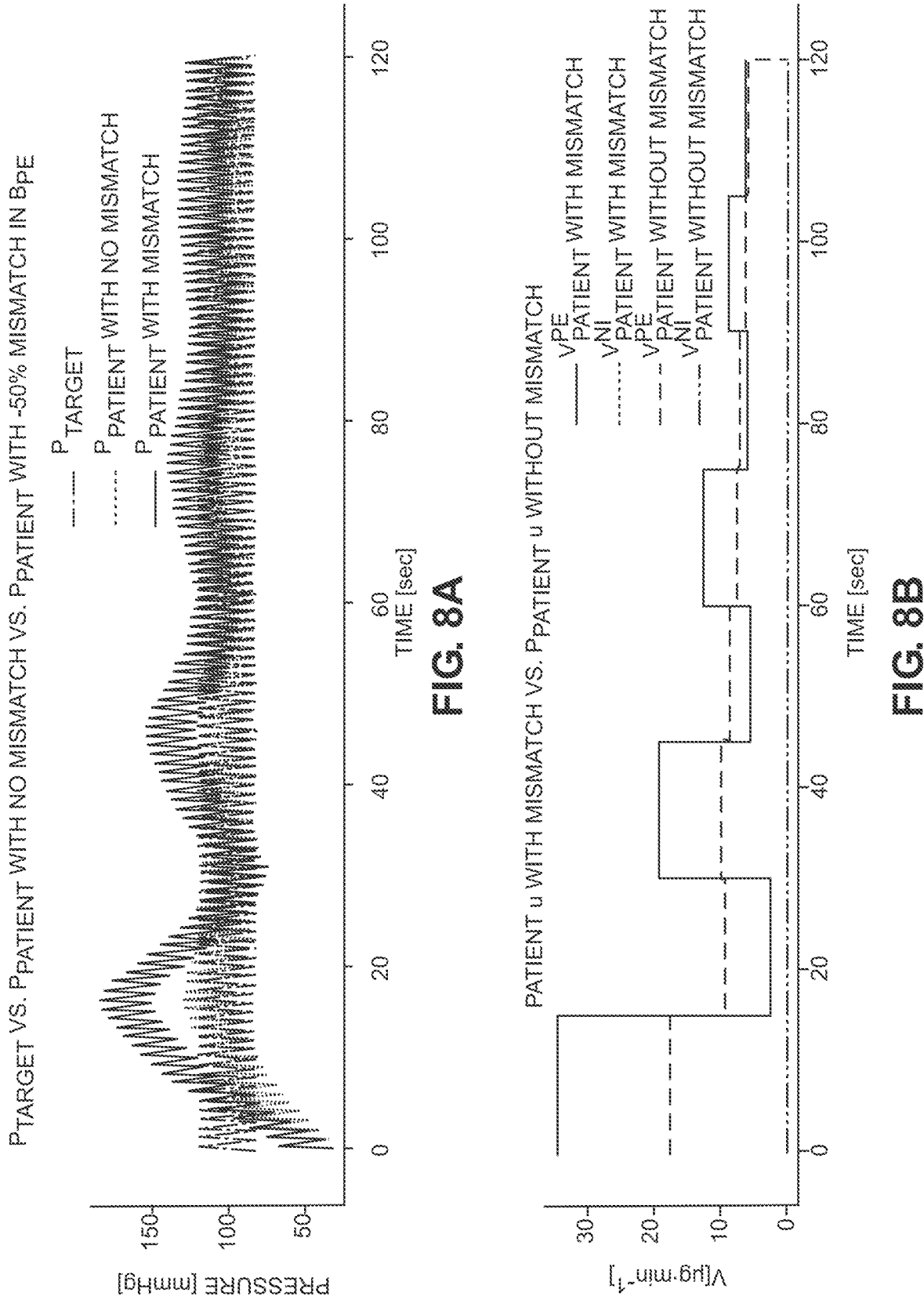
FIG. 8A shows the $p_{target}$, the resultant $p_{patient}$ from running control with mismatch, and the resultant $p_{patient}$ from running control without mismatch corresponding to a control simulation of blood pressure with model mismatch and slow updates. Specifically, $B^{PE}$ in $\theta_{patient}$ was modulated to be −50% of its mean value, and M was 15 [sec].
FIG. 8B shows the chosen drug infusion rates from MPC used to generate $p_{patient}$ with mismatch, and the chosen drug infusion rates from MPC used to generate $p_{patient}$ without mismatch for the simulation of FIG. 8A.

This was followed with a control simulation in FIGS. 8A and 8B where drug infusion rates could only be updated every 15 [sec], a rate which has improved flow rate accuracy in state of the art infusion pumps. The control simulations were otherwise identical. In this case, control performance was greatly impacted, e.g., overshoot is not clinically appropriate, reaching hypertension, at $O \approx 64.9$ [mmHg], patient blood pressure reaches within 10 [mmHg] of the target after $t_{s,10} \approx 113.3$ [sec], and MAE to the target waveform is about 5.5 times greater than the case with no mismatch at MAE≈18.2 [mmHg].

3.5.1 Robustness to Model Mismatch Analysis

Next, three summary figures are presented which analyze: 1) the effect of model mismatch of specific parameters on control performance metrics, and 2) the impact of M on robustness of the control framework to model mismatch of specific parameters.

Figure 9A:
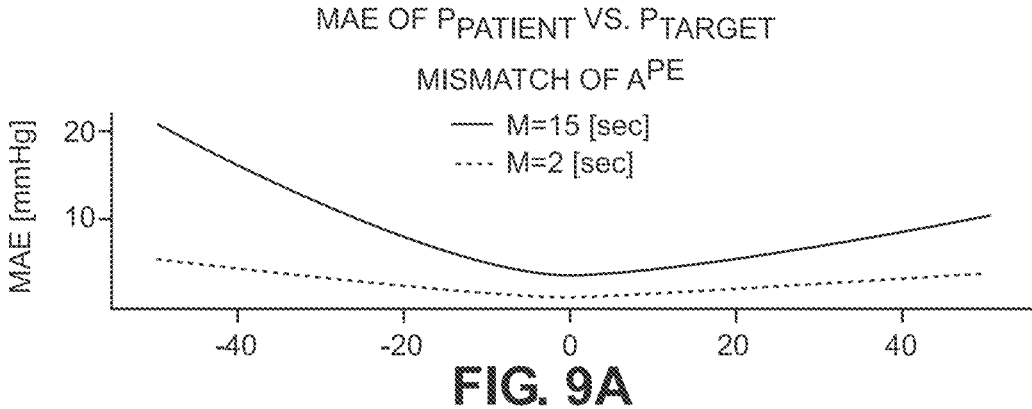
FIG. 9A shows the relationship between MAE and mismatch of $A^{PE}$ depending on M from simulations to illustrate the impact of model mismatch on MAE with varied switching constraints. The shaded regions show steady-state offset above 10 [mmHg] when M=2 [sec] and M=15 [sec].
Figure 9B:
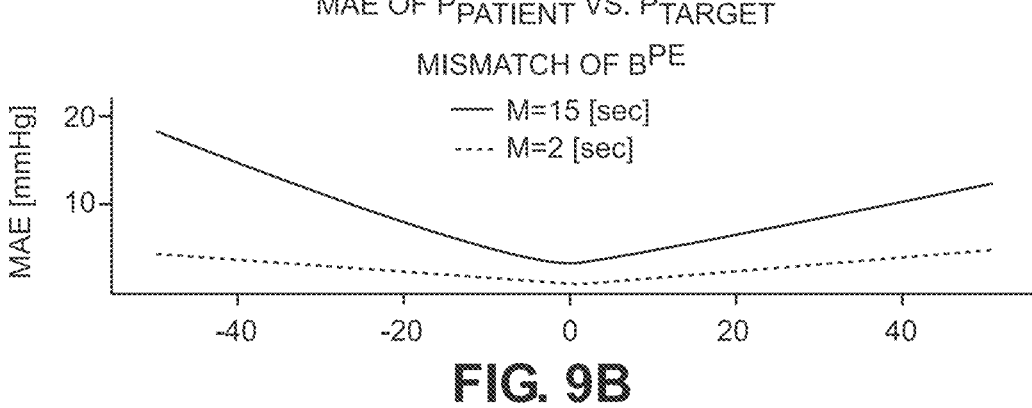
FIG. 9B shows the relationship between MAE and mismatch of $B^{PE}$ depending on M from simulations for the model mismatch of FIG. 9A. The shaded regions are interpreted in the same manner as FIG. 9A.
Figure 9C:
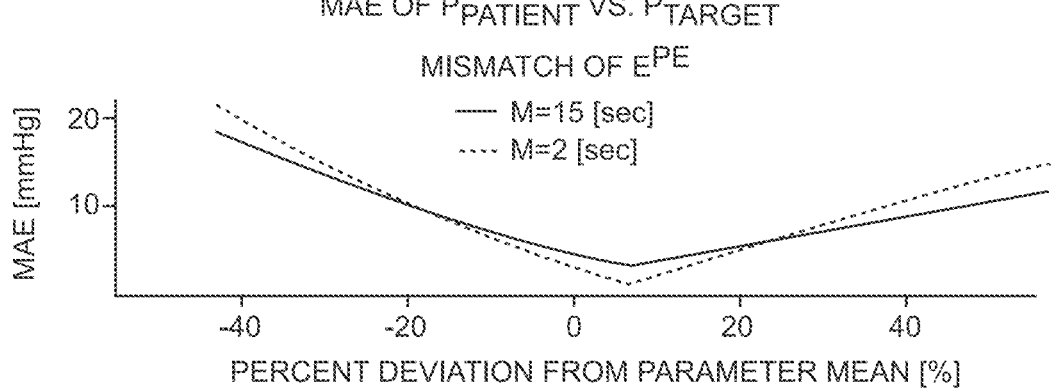
FIG. 9C shows the relationship between MAE and mismatch of $E^{PE}$ depending on M from simulations for the model mismatch of FIG. 9A. The shaded regions are interpreted in the same manner as FIG. 9A.

In FIGS. 9A-9C, the effect of varied model mismatch on MAE from $p_{patient}$ to $p_{target}$ is presented. When $A^{PE}$ or $B^{PE}$ were the parameters with mismatch and M=2 [sec], MAE variation due to model mismatch was relatively flat. In other words, MAE from model mismatch was similar to MAE with no mismatch. When M=15 [sec], the slope increased by about 4 times from the M=2 [sec] case for mismatch with $A^{PE}$ or $B^{PE}$. Impact on MAE from mismatch with $E^{PE}$ was similar with M=15 [sec] or M=2 [sec]. To promote lower MAE values in clinical studies, FIGS. 9A-9C results provide support for accurate estimation of $E^{PE}$ regardless of the frequency of infusion rate updates, and for accurate estimation of $A^{PE}$ and $B^{PE}$ with low frequency infusion rate updates.

In FIGS. 10A-10C, the effect of varied model mismatch on settling time, $t_{s,10}$, with a pressure bound of ±10 [mmHg] is presented. When $A^{PE}$, or $B^{PE}$ were the parameters with mismatch and M=2 [sec], $t_{s,10}$ variation due to model mismatch was relatively flat. In other words, $t_{s,10}$ from model mismatch was similar to $t_{s,10}$ with no mismatch. When M=15 [sec], $t_{s,10}$ increases as $A^{PE}$ and $B^{PE}$ are increased, and in some cases led to $p_{patient}$ with a steady-state offset greater than or equal to 10 [mmHg]. As $A^{PE}$ or $B^{PE}$ were increased, there was a period of time where $t_{s,10}$ decreased. After this, $t_{s,10}$ increased. Impact on $t_{s,10}$ from mismatch with $E^{PE}$ was similar with M=15 [sec] or M=2 [sec]. After a certain positive or negative modulation of $E^{PE}$, the resultant $p_{patient}$ waveform would have a steady-state offset greater than or equal to 10 [mmHg]. To avoid steady-state offsets, FIGS. 10A-10C results provide support for estimation of $E^{PE}$ regardless of the frequency of infusion rate updates, and for accurate estimation of $A^{PE}$ and $B^{PE}$ with low frequency infusion rate updates.

In FIGS. 11A-11C, the effect of varied model mismatch on overshoot, O, of $p_{patient}$ over $p_{target}$ is presented. When $A^{PE}$, $B^{PE}$ or $E^{PE}$ were the parameters with mismatch and M=2 [sec], O variation due to model mismatch was relatively flat. In other words, O from model mismatch was similar to O with no mismatch. When M=15 [sec], O monotonically increased as $A^{PE}$ or $B^{PE}$ were decreased, leading to hypertensive patient values. Modulation of $E^{PE}$ did lead to undershoot from the desired $p_{target}$ when M=2 [sec], which is less of a clinical concern, but is still undesirable given the control goal. To promote non-hypertensive overshoot responses in clinical studies, FIGS. 11A-11C results provide support for accurate estimation of $A^{PE}$ and $B^{PE}$ with low frequency infusion rate updates. To decrease frequency of undershoot in clinical studies, FIGS. 11A-11C results provide support for accurate estimation $E^{PE}$, especially with more rapid infusion rate updates.

3.6 Summary

The above sections present an improved model relating drug infusions of PE and NI to impacts on the cardiovascular system, and an improved MPC framework built around this model. A robustness study was also presented, which explored the impact of model mismatch on control performance. Based on the foregoing, guidance is provided for clinical studies on which parameters are critical to estimate accurately to promote certain control performance metrics to be met. These results further suggest that programmable infusion pump companies should increase the frequency at which drug infusion rates can be updated with high flow accuracy—specifically every 1-2 [sec] for the application of closed-loop blood pressure control.

FIGS. 7A and 7B show a control simulation with significant model mismatch and a switching constraint of 2 [sec] where performance is mildly impacted, whereas the same control simulation excluding a change in switching constraint to 15 [sec] leads to hindered control performance, as shown in FIGS. 8A and 8B.

The summarized results in FIGS. 9A-10C provide a more thorough assessment of impact of model mismatch on clinically relevant control performance metrics. They provide support for: 1) accurate estimation $E^{PE}$ in general, the parameter relating drug concentrations to impact on cardiovascular state, and 2) accurate estimation of $A^{PE}$ and $B^{PE}$, PK-model parameters, when the constraint on drug infusion updates is long in duration.

These combined results provide evidence that, clinical applicability of control systems should preferably include a combination of high fidelity estimates of model parameters and high frequency infusion rate updates from state of the art programmable infusion pumps. The longer one must wait to update infusion rates, the higher fidelity estimates one must have for sufficient control performance.

The model proposed in the foregoing sections provided theoretical improvements over previous formulations. First, the modeling assumption that the input flow to the peripheral circulation component of the Windkessel Model as an impulse train was relaxed. It is now modeled as a pulse train. Second, the MPC framework considered the full dynamics of the blood pressure waveform specified by the Windkessel Model with a time-varying τ when making infusion rate choices. These improvements provide more informed control decisions.

It should be appreciated further improvements may be made to the model. First, $d^{drug}$ and are not directly observable. For clinical control, it is desirable to estimate these states. Second, the PK model assumes that the first compartment of the PK model is also the effect site of each drug. This does not incorporate the delays observed between infusion of drug from an infusion pump to effect of said drug on a patient. Exploring the impact of this delay on robustness may also be incorporated into the model.

4. Example 4

This example is generally directed to a state-space method to estimate a time constant capturing the interplay of arterial resistance and compliance at a particular location in the arterial tree. In particular, this example is directed to providing real time estimation of the cardiovascular state of a patient for general patient care and for use in areas of technological innovation such as physiological closed loop control of the cardiovascular system. The approach builds on the two-element Windkessel model and estimates the time constant through Kalman filtering by relying solely on an arterial blood pressure waveform (ABP) as the observations, for implementation in a clinical setting. The method is validated on cardiovascular data collected in swine experiments. It is observed that the estimates match a ground truth time constant derived using ABP with aortic flow. The method improves upon existing techniques by providing estimates at a beat-by-beat time resolution while incorporating prior history of the waveform to achieve reduced noise. The method of estimating the ground-truth data also improves upon previous techniques by incorporating the dynamic equations of the Windkessel model. Overall, the method provides a principled framework to extract a relevant cardiovascular state, which can be useful in the study of the cardiovascular pharmacodynamics, and physiological closed loop control of the cardiovascular system.

4.1 Introduction

Estimation of real-time cardiovascular states of patients is desirable. These states can be directly observable, like mean blood pressure or heart rate, or can be difficult to observe, like cardiac output or systemic vascular resistance. Because the effects of cardiovascular drugs are complex, there may be benefits to estimating hidden states, which are physiologically interpretable for studying drug pharmacodynamics and building closed-loop systems for control of the cardiovascular system.

For clinical relevance, these cardiovascular state estimation techniques should preferably be non-invasive and reliable. A common approach is to estimate these physiologically interpretable hidden cardiovascular states from arterial blood pressure (ABP) waveforms using assumptions from simple circuit models of the cardiovascular system.

One such state is the time constant of the two-element Windkessel model which captures the interplay of arterial resistance and compliance of the arterial tree. Previous work produced estimates of the time constant that fall short through trade-offs in time resolution, invasiveness, and accuracy. Some perform estimation on a beat-by-beat time resolution or higher, but lack accuracy. Others seek to incorporate a longer segment of the blood pressure waveform into a single estimate to reduce the impact of wave reflections, which are the major artifact reducing the applicability of the Windkessel model in peripheral waveforms. These low time resolutions can be problematic in relevant applications like control.

In this section, a technique is disclosed, which produces beat-by-beat estimates of this time constant while also incorporating the history of the blood pressure waveform outside of the current beat. A state-space model of the time constant is constructed, with the time constant as the state, and diastolic component of the ABP waveform as the observations. With this model, a Kalman filter is implemented to provide noise reduction as well as a smooth resultant trajectory of estimates. To validate the results, insights from the two-element Windkessel model dynamic equation are used to derive an estimate of this time constant using both an aortic flow (AF) waveform and an ABP waveform, which is an improvement upon previous methods. With a swine cardiovascular data set, it is shown that estimates from the Kalman method using a single ABP waveform align with the validation estimates using an ABP waveform and an AF waveform. As such, an improved method is provided to estimate a physiologically interpretable hidden cardiovascular state from a single ABP waveform with qualities that qualify it for use in pharmacodynamic studies or as a control signal for a closed-loop system for cardiovascular control.

4.2 Methods 4.2.1 Physiological Model

The Windkessel model, a simple biophysical model of blood pressure dynamics in the aorta, provides a simple relationship between a blood pressure waveform and aggregate cardiovascular states. The physiological parallels in humans are shown in FIGS. 12A and 12B. The Windkessel model represents these dynamics through the interplay of a compliant system of major arteries and a terminal vascular resistance from the microcirculation (arterioles, capillaries, and venules) while considering the venous system's resistive contributions as negligible.

This example again refers to FIG. 3, which shows the circuit representation of the two-element Windkessel model. This is a representation which describes one cardiovascular state of a patient for a given set of initial conditions and parameters R and C. From this circuit model, one can derive the differential equation found in Eq. 6.1. The solution to this differential equation is a model of the blood pressure waveform.

$$\dot{p}(t) + \frac{1}{RC}p(t) = \frac{1}{C}f(t) \tag{6.1}$$

where f(t) in [L·min$^{-1}$] represents the volumetric inflow into the blood vessels from the heart, p(t) in [mmHg] represents the blood pressure waveform in the aorta, C in [L·mmHg$^{-1}$] is the compliance of the body's major vessels, and R in [mmHg·min·L$^{-1}$] is the terminal vascular resistance to blood flow.

In order to leverage the dynamics described by the two-element Windkessel model for estimation of a cardiovascular state, the following two additional assumptions are made. First, it is assumed that C and R are time-varying in that there is a single resistance value $R_k$ and a single capacitance value $C_k$ at beat k, but the value may change in between beats. Second, it is assumed f(t), the input flow rate from the heart to the twoelement model, is an impulse train. Each impulse has an area equivalent to the stroke volume represented as $\Delta V_k$ in [L]. The stroke volume is the amount of blood volume pumped by the heart per beat.

The time constant of the Windkessel Model at beat k, $\tau_k = R_k C_k$, governs the rate of decay of the diastolic portion of the simulated waveform for beat k. In other words, τ provides a link between an underlying state of the cardiovascular system and the observable ABP waveform. In FIG. 12C, this relationship is shown with simulations of the two-element Windkessel model and the additional assumptions. In FIGS. 12C-12E, two instances of in vivo swine data are shown which resemble the simulated data, further emphasizing this relationship between τ and changes observable in p. The estimation framework capitalizes on this relationship to learn $\tau_k$ from a blood pressure waveform.

4.2.2 Validation Framework: Estimating τ from AF and ABP

This section presents a method to estimate τ by separately estimating R and C to get τ=RC. This serves as a more informed estimate, though invasive, with which a comparison can be made to the less invasive estimation approach.

To estimate $\tau$ using this information, Eq. 6.1 is first discretized. A first-order backwards difference approximation to the first derivative of pressure, $\dot{p}(t)$, is defined as follows, $$p_d[n] := \frac{p(nT_s) - p(nT_s - 1)}{T_s} \tag{6.2}$$

where $$T_s = 60 f_s^{-1}$$

is the sampling period of p[n] and f[n] in [min]. Substituting this into Eq. 6.1, with the assumption that R and C vary between beats leads to, $$f[n] = \frac{1}{R_k} p[n] + C_k p_d[n] \text{ for } t \text{ within beat } k \tag{6.3}$$

A simple numerical integration is then performed using the rectangular rule to both sides over integration period $t_0$ to $t_1$, $$\sum_{t_0}^{t_1} f[n] T_s = \frac{1}{R_a[k]} \sum_{t_0}^{t_1} p[n] T_s + C_a[k] \sum_{t_0}^{t_1} p_d[n] T_s \tag{6.4}$$

If two unique integration periods are chosen, the result is two equations and two unknowns. Thus, an estimate of $\hat{R}_k$ and $\hat{C}_k$ can be solved separately, yielding an estimate of $\tau$.

This method of estimating $\tau$ with flow information improves upon previous techniques which consider the R and C components as separate, meaning they both receive the full flow from the aorta. This does not follow the structure of the Windkessel model and is also not physiologically possible.

4.2.3 Estimation Framework: Estimating $\tau$ from ABP Only

Reducing invasiveness is desirable for a clinically relevant cardiovascular state estimation framework. Here, a method is disclosed, which estimates $\tau$ with a single ABP waveform. An abstract illustration of the framework is presented in FIGS. 13A-13H.

This section discloses a state-space model of $\tau_k$, the time constant parameter in the two-element Windkessel model at beat k, where the state equation is a Gaussian random walk and the observation equation relates samples of the diastolic portion of an ABP pulse to the slowly varying $\tau_k$. With this state-space model, an estimate of $\tau_k$ can be obtained using a Kalman Filter.

Observation Equation

This section presents the derivation of the observation equation. From the two-element Windkessel, the diastolic decay of the blood pressure waveform can be described in terms of the time constant $\tau_k$. The ABP waveform follows an exponential decay from the end of the systolic period following the inflow of $\Delta V_k$ blood volume into the system. So, for a particular beat, the following relationship between $\tau_k$ and a single sample of the blood pressure waveform, $v_{k,i}$, can be specified, as follows, $$v_{k,i} = a_k \exp\left(-\frac{t_{k,i}}{\tau_k}\right) \tag{6.5}$$

where k indexes the heart beats, i indexes the $I_k$ observations per beat taken at a sampling rate $f_s$ in [Hz]. The number of observations per time point can vary for each beat; hence, I is also indexed by k. Additionally, $t_{k,i}$ corresponds to the time value in [sec] elapsed from the first blood pressure observation, $y_{k,0}$, and $a_k$ is the intercept of the exponential function at $t_{k,0}$. It is assumed $a_k$ is the initial observation of the diastolic period, $v_{k,i}$. For simplicity, Eq. 6.5 is log-transformed, as follows, $$\log(v_{k,i}) = \log\left(a_k e^{-\frac{t_{k,i}}{\tau_k}}\right) \tag{6.6}$$

$$= \log(a_k) - \frac{1}{\tau_k} t_{k,i} \tag{6.7}$$

The equation is rearranged to get $\tau_k$ on one side.

$$\log(v_{k,i}) - \log(a_k) = -\frac{1}{\tau_k} t_{k,i} \tag{6.8}$$

Next, the following is defined:

$$y_{k,i} = -(\log(v_{k,i}) - \log(a_k)) \tag{6.9}$$

Then, a solution for an equation with which T can be the state variable is obtained, and there are no inverses of either the observations or time vector:

$$t_{k,i} = y_{k,i} \tau_k \tag{6.10}$$

Now, with this transformed relationship, the assumption of additive noise is made:

$$t_{k,i} = y_{k,i} \tau_k + \epsilon_{k,i} \tag{6.11}$$

The observation equation can be represented in a more compact notation by expanding over the i index. This is the final observation equation, $$\begin{bmatrix} t_{k,0} \\ t_{k,1} \\ \vdots \\ t_{k,I_k-1} \end{bmatrix} = \begin{bmatrix} y_{k,0} \\ y_{k,1} \\ \vdots \\ y_{k,I_k-1} \end{bmatrix} \tau_k + \begin{bmatrix} \epsilon_{k,0} \\ \epsilon_{k,1} \\ \vdots \\ \epsilon_{k,I_k-1} \end{bmatrix} \tag{6.12}$$

which can then be represented in the following way, $$t_k = y_k \tau_k + \epsilon_k \tag{6.13}$$

where the column vectors $y_k \in \mathbb{R}^{I_k}$, $\tau_k \in \mathbb{R}$, $\epsilon_k \in \mathbb{R}^{I_k}$, $t_k \in \mathbb{R}^{I_k}$. The covariance matrix of the defined noise vector at beat k is $$\sum_{\epsilon,k} = \sigma_\epsilon^2 I_{I_k},$$

given $I_{I_k}$ is an identity matrix of dimension $I_k \times I_k$.

State Space Equation

This section presents the derivation of the state space equation. As described above, a linear observation equation is derived, which relates the desired parameter to be estimated, $\tau_k$, with what can be observed, $v_{k,i}$. A state-space equation is now specified, which simply constrains the state values to vary smoothly over time, since the cardiovascular state, $\tau_k$, is not expected to change rapidly. As such, it is assumed the state, $\tau_k$, follows a Gaussian random walk, $$\tau_{k+1} = \tau_k + \eta_k \tag{6.14}$$

where $$\eta_k \sim N(0, \sigma_{\eta,1}^2)$$

and each $\eta_k$ is independent. The choice of $$\sigma_\eta^2$$

impacts the performance of the following estimation. With this, the state-space equation is fully specified.

Kalman Filter Equations

The following sections present the Kalman Filter equations given the above state-space model. Since a maximum a posteriori (MAP) estimate, $\tau_{[k-1|k-1]}$, of $\tau_{k-1}$ at beat k−1 is obtained and the defined observation and state equations above have Gaussian additive noise, the state estimation framework can be specified using the traditional Kalman filter equations.

One-Step Prediction Density

First, a one-step prediction density is defined. This Gaussian distribution is specified with the one-step state prediction of $\tau_k$ for beat k given observations up to beat k−1, $$\tau_{[k|k-1]} = \tau_{[k-1|k-1]} \tag{6.15}$$

and the following one-step prediction variance is, $$\sigma_{[k|k-1]}^2 = \sigma_{[k-1|k-1]}^2 + \sigma_\eta^2 \tag{6.16}$$

Kalman Gain

Next, the Kalman gain term is defined, as follows, $$K_k = \sigma_{[k|k-1]}^2 y_k^T \left( y_k \sigma_{[k|k-1]}^2 y_k^T + \sum_{\epsilon,k} \right)^{-1} \tag{6.17}$$

Posterior Density

The posterior density, additionally a Gaussian distribution, can be fully specified with the MAP estimate at beat k given observations including beat k as, $$\tau_{[k|k]} = \tau_{[k|k-1]} + K_k \left( t_k - y_k \tau_{[k|k-1]} \right) \tag{6.18}$$

and the posterior density variance as, $$\sigma_{[k|k]}^2 = (1 - K_k y_k) \sigma_{k|k-1}^2 (1 - K_k y_k)^T \tag{6.19}$$

$$+ K_k \sum_{\epsilon k} K_k^T \tag{6.20}$$

Prior Density

In order to run this Kalman filter, an assumption is made on the distribution of the initial state, $\tau_0$. The following observation equation corresponds to this beat, $$t_0 = y_0 \tau_0 + \epsilon_0 \tag{6.21}$$

The MAP estimate, $\tau_{[0|0]}$, is defined with a standard linear regression which defines the MAP estimate as, $$\tau_{[0|0]} = \left( y_0^T y_0 \right)^{-1} y_0^T t_0 \tag{6.22}$$

with variance, $$\sigma_{[0|0]}^2 = \left( y_0^T y_0 \right)^{-1} \hat{\sigma}_\epsilon^2 \tag{6.23}$$

and as further specified, $$\hat{\sigma}_\epsilon^2 = \frac{\left( t_0 - y_0 \tau_{[0|0]} \right)^T \left( t_0 - y_0 \tau_{[0|0]} \right)}{I_0} \tag{6.24}$$

where $I_0$ is the number of observations from the initial beat. With this specified Kalman filter, a MAP estimate, τ[k|k], can be obtained for every beat.

This method of estimating τ with a single ABP waveform improves upon previous techniques by providing accurate beat-by-beat estimates with a smooth estimate trajectory (as shown in Section 4.3). With this formulation, the 95% credibility interval can be calculated, which is the analog to a confidence interval in Bayesian statistics, for each $$\tau_k \sim N\left( \tau_{[k|k]}, \sigma_{[k|k]}^2 \right)$$

by generating the cumulative distribution function of $\tau_k$ and finding the 2.5th and 97.5th percentiles.

4.2.4 Experimental Data

A swine data set is used to generate estimates from both the clinically relevant single ABP approach, and the validation ABP and AF approach. The data used for the estimation framework validation is from previous work. In this data set, six young Yorkshire swine (30-34 kg) were monitored over a wide array of interventions to manipulate cardiac state including the following: infusions of volume, phenylephrine, dobutamine, isoproterenol, esmolol, nitroglycerine, and progressive hemorrhage. In each experiment, recordings were made of peripheral ABP (femoral, and radial), central ABP, and AF. An external pressure transducer (TSD104A, Biopac Systems, Santa Barbara, CA) was used for femoral ABP, $p^{femoral}[n]$, in [mmHg], a 23- or 25-gauge angiocatheter was in the brachial artery for radial ABP, $p^{radial}[n]$, in [mmHg], and a micro-manometer-tipped catheter (SPC 350, Millar Instruments, Houston, TX) was fed retrograde to the thoracic aorta for central ABP, $p^{central}[n]$, in [mmHg]. AF, f[n], was recorded from an ultrasonic flow probe (T206 with A-series probes, Transonic Systems, Ithaca, NY) placed around the aortic root. From these probes, flow is determined by the transit-time technique. This protocol yielded discrete ABP, p[n], and AF waveforms, f[n], both sampled at 250 [Hz].

4.2.5 Arterial Blood Pressure Signal Processing

This section describes the ABP signal processing used to run the estimation and validation frameworks. For the Kalman framework, the onset of each ABP pulse is extracted first followed by the diastolic observations. For the validation framework, the onset of each ABP pulse is extracted first followed by identifying a feature of the ABP pulse to align it with each corresponding AF pulse.

To process each ABP waveform, the waveform is first filtered using a Kaiser window low pass filter with a pass band at 10 [Hz] and a stop band at 12 [Hz]. Next, initial detection of the ABP pulse onsets is achieved using the slope sum technique. With insight from the Windkessel model, the onset of an ABP pulse begins when the derivative of p starts to increase after the diastolic decay. As such, the onsets are corrected to be the first minimum of $p_d[n]$ looking backwards from the detected onset using the slope sum technique. Following the onset detection, the systolic peak is found with a simple maximum of p[n] between onset of beat k and k+1.

For the Kalman framework, the ABP observations, $v_{k,i}$, are then extracted. For each beat, the diastolic decay of the blood pressure pulse is extracted after the aortic valve closes. To extract this diastolic component, the first-order backwards difference of p[n], $p_d[n]$ is assessed within the time window between the systolic peak for beat k and the onset of beat k+1. The first $p_d[n]$ minimum is found following the systolic peak. This point is chosen because, following an aortic flow pulse, there is a period of backflow as the aortic valve closes. This is visible at t≈0.22 in FIG. 13F. This backflow leads to a maximum rate of decay of the blood pressure waveform that is detectable in central and peripheral waveforms. The observations begin at this first negative minimum of $p_d[n]$ following the systolic peak. The following onset at beat k+1 is then used as the final observation for the diastolic decay. Also, p[n] is extracted between the detected beginning of diastole and the following onset. From these observations, the estimation framework specified in Section 4.2.3 is run to get $\tau_{[k|k]}$.

For the validation framework, a feature is extracted to align the ABP and AF pulse. Once again, the first negative $p_d[n]$ minimum following the systolic peak for each pulse is used, as this corresponds to the easily detectible backflow minimum in each AF pulse. In FIG. 13G, the ABP systolic peak is at t≈0.2, and the following negative minimum of $p_d[n]$ is at t≈0.23, as shown in FIG. 13H.

With these detected onsets and ABP features indicating diastole or the point of AF backflow, both Kalman and validation τ estimation frameworks can be run.

4.2.6 Aortic Flow Signal Processing

This section describes the AF signal processing used to run the validation framework. Now that an ABP pulse feature is obtained, which can be related to the AF pulse, each pulse is aligned. First, all samples of p[n] and f[n] are extracted between onsets k and k+1 detected from the ABP waveform using the slope sum technique with the onset correction described in Section 4.2.5.

Next, the extracted kth f[n] and p[n] pulses are aligned. Correct kth pulse alignment corresponds to the point of greatest backflow of f[n] (the minimum of f[n]) that matches with the first negative minimum in $p_d[n]$ following the systolic peak for beat k. This approach uses similar logic to the approach for identification of the diastolic portion of an ABP pulse. In some peripheral blood pressure waveforms, the waveform morphology can lead to a minimum in p[n] which does not correspond to the greatest backflow in f[n]. This can be corrected by ensuring calculated shift does not move the ABP pulse backwards in time.

With the aligned f[n] and p[n] pulses, the procedure in Section 4.2.2 can be run.

4.3 Results 4.3.1 Kalman Estimates are Beat by Beat and Reduce Noise

The Kalman estimation framework produces a smooth trajectory of beat-by-beat estimates of τ from a single ABP waveform, where each beat estimate has an explicit confidence interval. The algorithm takes an ABP waveform segment as input (FIG. 14A, top) and provides an estimated time constant trajectory (FIG. 14A, bottom). This trajectory tracks time constant estimates obtained separately and independently at each beat (FIGS. 14A-D, bottom, in red) by fitting an exponential curve to the diastolic portion of each blood pressure pulse. It is found that the Kalman estimates are responsive to quick changes in τ (FIG. 14C). It is also found that by incorporating history dependence, the algorithm filters out noise artifacts, particularly related to breathing (observe the oscillations in the red trajectory), or erroneous measurements, leading to a smooth state estimate (FIGS. 14A-D).

4.3.2 Kalman Estimates Track Validation Estimates

The time constant, τ=RC, can be directly derived using ABP and AF by separately computing R and C from the Windkessel model dynamics, as described in Section 4.2.2. The state-space method, described in 4.2.3, provides a way to estimate τ in a non-invasive manner, bypassing the use of AF. It then remains to check whether the estimated τ coincides with the one derived with the more invasive approach using ABP and AF. As such, time constants are derived using both frameworks, and a comparison then made between the resultant estimates. Estimates are produced using three locations of blood pressure measurements: central, femoral and radial. The Kalman estimates are shown to indeed track the estimate derived using the flow in central (FIG. 15A), femoral (FIG. 15B) and radial (FIG. 15C) locations for all experiments. The full estimation results of every experiment are shown in FIGS. 16A-20D.

These experiments only measured central aortic flow, not flow into the location of catheterization. To use this information in the peripheral—femoral and radial—locations, the two-element Windkessel model is extended to incorporate different vascularization. By assuming that the majority of capacitance comes from the aorta, the arterial bed is modeled as a combination of resistive components such that there is no leakage of flow from various vessels into other arterial branches. For a constant aortic flow f the flow into the location of catheterization is f=αf for some fixed scaling factor α, which is a function of the resistances. With this relationship of AF to flow into a peripheral artery, the estimation framework is justified and the use of AF does not affect the estimated time constant from the periphery. Although there is leakage and backflow of blood volume in the peripheral circulation, this assumption is appropriate given the proposed application in physiological closed loop control.

4.3.3 Kalman Estimates from Central and Peripheral ABP Align in Multiple Experiments For clinical relevance, it is desirable to estimate cardiovascular parameters peripherally to reduce invasiveness. The Kalman $\tau$ estimates derived from the radial and femoral locations are evaluated to assess whether they agree with the central estimates to determine whether it is possible to peripherally learn central cardiovascular parameters.

In Experiment 1, not only does the Kalman estimate track the validation estimate within each ABP recording location, but there is also agreement between estimates from each recording location, as shown in FIG. 15D. In FIGS. 16A-20D, the following is further shown: in two out of the six experiments, estimates from radial, femoral, and central align for the entire experiment; in two of the remaining experiments, estimates from radial, femoral, and central align for the about 75% of the experiment; in the final two experiments, there is more prominent deviation of estimates from different recording locations.

Previous research findings have argued that cardiovascular state estimates differ substantially when learned centrally or peripherally. Some such work focused on estimating resistance R, capacitance C. These quantities are separately affected by changes in blood pressure and flow. The present disclosure focuses on the time constant that combines R and C, and reflects flow clearance during the diastolic period, which can be global cardiovascular state. Previous studies focused on estimation of cardiac output from a peripheral waveform rather than $\tau$ itself. These results show a match among multiple locations is promising for the use of this cardiovascular state in pharmacodynamic studies and control. While some differences are observed in Experiments 2 and 4, these observed differences could be due to measurement acquisition methods and measurement artifacts. For instance, air bubbles can be a common occurrence. If the recording device (fluid-filled catheter) is modeled as an RC circuit, the bubble is expected to alter its compliance which can then affect the ABP measurement, and therefore the estimate of $\tau$. Further elaboration is provided on the subject of whether one can use peripheral measurements to estimate central parameters in the discussion section.

4.4 Discussion

In the above sections, a method is disclosed for estimating a physiologically interpretable cardiovascular state, the time constant of the two-element Windkessel model, from a single ABP waveform. A state-space model of $\tau$ is constructed, with $\tau$ as the state, and the diastolic component of each ABP pulse as the observations. Then, $\tau$ is estimated with a Kalman filter. A comparison is then made between the resultant estimates from the disclosed method and validation estimates derived from both an AF waveform and an ABP waveform using a swine cardiovascular data set. In every experiment, and for every recording location—radial, femoral or central—the Kalman estimates using a single ABP waveform tracked using both an AF and ABP waveform. Within an experiment, estimates from one recording location often tracked estimates from different ABP recording locations.

In the context of estimating $\tau$ from a single peripheral blood pressure waveform, the disclosed technique has many benefits. First, the method yields estimates of $\tau$ on a beat-by-beat time resolution. Second, given the incorporation of ABP history outside of the current beat k into the estimate, noise of the resultant trajectories is reduced. With the use of a Kalman filter for estimation, noise reduction for the estimate trajectory is achieved given the constraints of the model description. Third, the use of a state-space model to model the dynamics of $\tau_k$ constrains the state estimate to move smoothly over time, modulated by selection of state and observation noise parameters, $$\sigma_\eta^2 \text{ and } \sigma_\epsilon^2.$$

This is appropriate as physiological systems over short time scales move smoothly. The state, $\tau$, describes aspects of the vasculature like vessel muscle constriction, something which does not change instantaneously. For these reasons, the estimates greatly improve upon previous single ABP methods, which produce beat-by-beat estimates with significant noise or estimates with reduced noise at over a minute time resolution.

Because of the three benefits of the disclosed method— time resolution, noise reduction, and smooth dynamics of the estimates—this cardiovascular state estimate has the potential to function as a control signal (a signal that is regulated in a closed loop control system). As such, estimates from the framework could provide improvements towards viable physiological closed loop control systems tasked at regulating cardiovascular state in real time. Additionally, because the state is physiologically interpretable, studies of the pharmacodynamics of vasoactive drugs for this state would be informative.

Additionally, the validation technique considered the full dynamic equation of the two-element Windkessel model and took full advantage of the AF waveform. Previous approaches relied on a poor physiological assumption, namely that the R and C branches of the two-element Windkessel model both received the full aortic flow input. Variation of the validation estimates within a certain ABP location may have stemmed from varied alignment of f[n] and p[n] between pulses. Given the reliability and clinical relevance of the Kalman estimates, however, improvements to this variability may not appreciably impact performance.

Although R and C cannot be differentiated using a single peripheral waveform, a directly related cardiovascular state, $\tau$, can be computed, which contains interpretable mechanistic information about the cardiovascular system. Through matching estimates from across the arterial tree, it has been shown that this parameter is also likely shared along the vasculature. For these reasons, and the additional benefits mentioned above, it is likely that $\tau$, estimated with the framework, can serve as a control signal in closed loop control of the cardiovascular system.

5. Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of"

"Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system for controlling blood pressure in a subject, comprising:

a sensor configured to be coupled to the subject and configured to measure a blood pressure waveform of the subject;

a pump configured to be coupled to the subject and configured to a) inject a first substance including a vasopressor into the subject, and b) a second substance including a vasodilator into the subject; and a processor communicatively coupled to the sensor and the pump, the processor configured to:

receive an indication of a target blood pressure waveform of the subject;

receive, from the sensor, an indication of the measured blood pressure waveform of the subject;

calculate an estimated blood pressure waveform of the subject based on a circuit model of blood circulation in one or more blood vessels of the subject by:

setting an input blood flow parameter of the circuit model to be an impulse train or a pulse train;

setting an arterial compliance parameter of the circuit model to be time invariant;

setting a microcirculation resistance parameter of the circuit model to be time invariant during a heartbeat and time variant between each heartbeat; and calculating the estimated blood pressure waveform by solving the dynamics of the circuit model based on the input blood flow parameter, the arterial compliance parameter, the microcirculation resistance parameter, and the measured blood pressure waveform;

calculate, based on the estimated blood pressure waveform and the target blood pressure waveform, one or more infusion rates for the first substance, for the second substance, or both; and transmit an indication of the one or more calculated infusion rates to the pump, wherein the pump is further configured to modify an infusion rate of the first substance, of the second substance, or both, based on the one or more calculated infusion rates.

2. The system of claim 1, wherein the processor is further configured to:

estimate a time constant parameter of the circuit model, for each heartbeat of the subject, by applying a Kalman filter to the measured blood pressure waveform; and estimate the arterial compliance parameter, the microcirculation resistance parameter, and the input blood flow parameter of the circuit model based on the time constant parameter for each heartbeat of the subject, wherein the processor is further configured to calculate the estimated blood pressure waveform by solving the circuit model based on the input blood flow parameter, the arterial compliance parameter, and the microcirculation resistance parameter.

3. The system of claim 1, wherein the processor is further configured to remove high frequency noise from the measured blood pressure waveform with a low pass filter prior to calculating the estimated blood pressure waveform.

4. The system of claim 3, wherein the low pass filter is a symmetric or anti-symmetric, finite impulse response (FIR) filter.

5. The system of claim 1, wherein the circuit model is a first model, and wherein the processor is further configured to:

define a second model of substance metabolization as a combination of a first two-compartment pharmacokinetic model for the first substance and a second two-compartment pharmacokinetic model for the second substance;

define a state space model based on the first model and the second model; and calculate the one or more infusion rates based on the state space model.

6. The system of claim 1, wherein the processor is further configured to calculate the one or more infusion rates based on a model predictive control (MPC) framework and one or more constraints applied to the MPC framework.

7. The system of claim 6, wherein the one or more constraints include one or more of:

an indication that a negative infusion rate is not permitted;

a maximum infusion rate for the first substance, for the second substance, or both; or a maximum frequency of change of an infusion rate for the first substance, the second substance, or both.

8. The system of claim 1, wherein the vasopressor is selected from the group consisting of: epinephrine, norepinephrine, phenylephrine, ephedrine, droxidopa, isoproterenol, angiotensin II, and dobutamine.

9. The system of claim 8, wherein the vasopressor is phenylephrine.

10. The system of claim 1, wherein the vasodilator is selected from the group consisting of: alprostadil, nitroglycerin, nicardipine, hydralazine, riociguat, vericiguat, nitroprusside, nesiritide, and minoxidil.

11. The system of claim 10, wherein the vasodilator is nicardipine.

12. A method for controlling blood pressure in a subject, comprising:

measuring a blood pressure waveform of the subject;

injecting a first substance including a vasopressor into the subject, and second substance including a vasodilator into the subject;

receiving an indication of a target blood pressure waveform of the subject;

calculating an estimated blood pressure waveform of the subject based on a circuit model of blood circulation in one or more blood vessels of the subject by:

setting an input blood flow parameter of the circuit model to be an impulse train or a pulse train;

setting an arterial compliance parameter of the circuit model to be time invariant;

setting a microcirculation resistance parameter of the circuit model to be time invariant during a heartbeat and time variant between each heartbeat; and calculating the estimated blood pressure waveform by solving the circuit model based on the input blood flow parameter, the arterial compliance parameter, the microcirculation resistance parameter, and the measured blood pressure waveform;

calculating, based on the estimated blood pressure waveform and the target blood pressure waveform, one or more infusion rates for the first substance, for the second substance, or both; and modifying an infusion rate of the first substance, of the second substance, or both, based on the one or more calculated infusion rates.

13. The method of claim 12, further comprising:

estimating a time constant parameter of the circuit model, for each heartbeat of the subject, by applying a Kalman filter to the measured blood pressure waveform; and estimating the arterial compliance parameter, the microcirculation resistance parameter, and the input blood parameter of the circuit model based on the time constant parameter for each heartbeat of the subject, the calculating the estimated blood pressure waveform further including solving the circuit model based on the input blood flow parameter, the arterial compliance parameter, and the microcirculation resistance parameter.

14. The method of claim 12, further comprising removing high frequency noise the measured blood pressure waveform with a low pass filter prior to calculating the estimated blood pressure waveform.

15. The method of claim 14, wherein the low pass filter is a symmetric or anti-symmetric, finite impulse response (FIR) filter.

16. The method of claim 12, wherein the circuit model is a first model, the method further comprising:

defining a second model of substance metabolization as a combination of a first two-compartment pharmacokinetic model for the first substance and a second two-compartment pharmacokinetic model for the second substance;

defining a state space model based on the first model and the second model; and calculating the one or more infusion rates based on the state space model.

17. The method of claim 12, further comprising calculating the one or more infusion rates based on a model predictive control (MPC) framework and one or more constraints applied to the MPC framework.

18. The method of claim 17, wherein the one or more constraints include one or more of:

an indication that a negative infusion rate is not permitted;

a maximum infusion rate for the first substance, for the second substance, or both; or a maximum frequency of change of an infusion rate for the first substance, the second substance, or both.

19. The method of claim 12, wherein the vasopressor is selected from the group consisting of: epinephrine, norepinephrine, phenylephrine, ephedrine, droxidopa, isoproterenol, angiotensin II, and dobutamine.

20. The method of claim 12, wherein the vasodilator is selected from the group consisting of: alprostadil, nitroglycerin, nicardipine, hydralazine, riociguat, vericiguat, nitroprusside, nesiritide, and minoxidil.

\* \* \* \* \*